United States Patent
Lustigman et al.

(10) Patent No.: US 12,251,432 B2
(45) Date of Patent: Mar. 18, 2025

(54) BIOMARKERS AND IMMUNOGENIC COMPOSITIONS FOR FILARIAL PARASITES

(71) Applicants: New York Blood Center, Inc., New York, NY (US); The United States of America, as Represented by the Secretary, Department of Health and Human Services, Rockville, MD (US)

(72) Inventors: Sara Lustigman, New York, NY (US); Thomas B. Nutman, Bethesda, MD (US); Sasisekhar Bennuru, Bethesda, MD (US)

(73) Assignees: New York Blood Center, Inc., New York, NY (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/076,616

(22) Filed: Oct. 21, 2020

(65) Prior Publication Data

US 2021/0046170 A1 Feb. 18, 2021

Related U.S. Application Data

(62) Division of application No. 16/090,013, filed as application No. PCT/US2017/025554 on Mar. 31, 2017, now abandoned.

(60) Provisional application No. 62/317,243, filed on Apr. 1, 2016.

(51) Int. Cl.
| | |
|---|---|
| *A61K 39/00* | (2006.01) |
| *A61P 33/10* | (2006.01) |
| *C07K 14/435* | (2006.01) |
| *C07K 16/18* | (2006.01) |
| *G01N 33/53* | (2006.01) |

(52) U.S. Cl.
CPC .......... *A61K 39/0003* (2013.01); *A61P 33/10* (2018.01); *C07K 14/4354* (2013.01); *C07K 16/18* (2013.01); *G01N 33/5308* (2013.01); *A61K 2039/552* (2013.01); *A61K 2039/55505* (2013.01); *A61K 2039/6031* (2013.01); *A61K 2039/70* (2013.01)

(58) Field of Classification Search
CPC .......... A61K 39/0003; A61K 2039/552; A61K 2039/55505; A61K 2039/6031; A61K 39/70; A61P 33/10; C07K 14/4354; C07K 16/18; G01N 33/5308
See application file for complete search history.

(56) References Cited

U.S. PATENT DOCUMENTS

| | | |
|---|---|---|
| 5,021,342 A | 6/1991 | Greene et al. |
| 2006/0039921 A1 | 2/2006 | MacDonald et al. |

FOREIGN PATENT DOCUMENTS

WO 2015/121646 A1 8/2015

OTHER PUBLICATIONS

Tamashiro et al. (American Journal of Tropical Medicine and Hygiene vol. 404 No. 4, pp. 368-376).*
Bennuru et al. "Stage-specific transcriptome and proteome analyses of the filarial parasite Onchocerca volvulus and its Wolbachia endosymbiont," mBio 7:1-11, 2016.
Cotton et al. "The genome of Onchocerca volvulus, agent of river blindness," Nature Microbiology 2:1-12, 2016.
Taylor et al. "Protective immunity induced by vaccination with Onchocerca volvulus tropomysin in rodents," Parasite Immunology 18:219,225, 1996.
Arumugam et al. "Vaccination with recombinant Brugia malayi cystatin proteins alters worm migration, homing and final niche selection following a subcutaneous challenge of Mongolian gerbils (Meriones unguiculatus) with B. malayi infective larvae," Parasites & Vectors 7:43-49, 2014.
Arumugam et al. "Vaccination with genetically modified Brugia malayi cysteine protease inhibitor 2 reduces adult parasite numbers and affects the fertility of female worms following a subcutaneous challenge of Mongolian gerbils (Meriones unguiculatus) with B. malayi infective larvae," Int J Parasitology 44:675-679, 2014.
Hess et al. "Vaccines to combat river blindness: expression, selection and formulation of vaccines against infection with Onchocerca volvulus in mouse model," 44"637-646, 2014.
Hess et al. The immunomodulatory role of adjuvants in vaccines formulated with the recombinant antigens Ov-103 and Ov-RAL-2 against Onchocerca volvulus in mice. PLoS Negl Trop Dis 10(7):e0004797, 2016.
Arumugam et al. "Vaccination of gerbils with Bm-103 and Bm-RAL-2 concurrently or as a fusion protein confers consistent and improved protection against Brugia malayi infection." PLoS Negl Trop Dis 4(10):e0004586, 2016.
Bennuru S et al. "Metabolite profiling of infection-associated metabolic markers of onchocerciasis" Mol Biochem Parasitol 215:58-69, 2017.
Bennuru S "Understanding hidden antigens and targeting parasitic nematodes" EBioMedicine 2:1010-1011, 2015.
Bennuru S et al. "Mining filarial genomes for diagnostic and therapeutic targets" Trends Parasitol 34:80-90, 2018.
Patton JB et al. "Development of Onchocerca volvulus in humanized NSG mice and detection of parasite biomarkers in urine and serum" PLoS Negl Trop Dis 12:e0006977, 2018.
Skolnick, J et al. "From genes to protein structure and function: novel applications of computational approaches in the genomic era" TIBTECH 18:34-39, 2000.
International Search Report and Written Opinion PCT/US2017/025554 issued Jul. 5, 2017.

(Continued)

Primary Examiner — Robert A Zeman
(74) Attorney, Agent, or Firm — Fish & Richardson P.C.

(57) ABSTRACT

Disclosed herein are immunogenic compositions for preventing or treating infection with filarial parasites and biomarkers for diagnosing infection with filarial parasites.

10 Claims, 18 Drawing Sheets

Specification includes a Sequence Listing.

(56) References Cited

OTHER PUBLICATIONS

Boslego JW et al. "Gonorrhea vaccines" Vaccines and Immunotherapy, Chapter 17, 1991.

Ellis. Vaccines, W.b. Saunders Company, Chapter 29, pp. 568-574, 1988.

George PV et al. "Antibody responses against the vaccine antigens Ov-103 and Ov-RAL-2 are associated with protective immunity to Onchocerca volvulus infection in both mice and humans." PLoS Negl Trop Dis 13(9):e0007730. https://doi.org/10.1371/journal.pntd.0007730, 2019.

Limberger RJ and McReynolds LA "Filarial paramyosin: cDNA sequences from Dirofilaria immitis and Onchocerca volvulus." Mol Biochem Parasitol 38:271-280, 1990.

Cafarelli C et al. "De novo genome sequencing and comparative stage-specific transcriptomic analysis of Dirofilaria repens." Int J Parasitol 49:911-919, 2019.

Mejia JS et al. "Expression of an Onchocerca volvulus Ov33 homolog in Dirofilaria immitis: potential in diagnosis of heartworm infection." Parasite Immunol 16:297-303, 1994.

Boto WMO et al. "Homologous and distinctive antigens of Onchocerca volvulus and Dirofilaria immitis: detection by an enzyme-linked immuno-inhibition assay." J Immunol 133:981-987, 1984.

Boatin et al., "Control of onchocerciasis," Advances in parasitology, Jan. 2006, 61:349-94.

International Preliminary Report on Patentability in International Appln. No. PCT/US2017/025554, mailed on Oct. 11, 2018, 6 pages.

Needleman et al., "A general method applicable to the search for similarities in the amino acid sequence of two proteins," Journal of molecular biology, Mar. 28, 1970, 48(3):443-53.

UniProt Accession No. UP000024404, "Genome sequencing of Onchocerca volvulus," dated Oct. 1, 2023, 1 page.

\* cited by examiner

BIOMARKERS AND IMMUNOGENIC COMPOSITIONS FOR FILARIAL PARASITES

CROSS REFERENCE TO RELATED APPLICATIONS

The present application is a division of U.S. patent application Ser. No. 16/090,013 filed Sep. 28, 2018, which is a 35 U.S.C. § 371 national phase entry of PCT/US2017/025554, filed Mar. 31, 2017, which claims the benefit of U.S. Provisional Patent Application 62/317,243 filed Apr. 1, 2016, the entire contents of all of which are incorporated by reference herein.

STATEMENT REGARDING FEDERALLY SPONSORED RESEARCH

This invention was made in part with government support under Grant/Contract Number AI42328 awarded by the Division of Microbiology and Infectious Diseases, National Institute of Allergy and Infectious Diseases, National Institutes of Health; the Division of Intramural Research (DIR) of the National Institute of Allergy and Infectious Diseases, National Institutes of Health. The government has certain rights in the invention.

BACKGROUND

Onchocerciasis (river blindness) is a neglected tropical disease, caused by infection with *Onchocerca volvulus*, that has been targeted for control and elimination through mass drug administration (MDA) of ivermectin that ultimately interrupts transmission. The ultimate success of MDA for onchocerciasis will largely depend on additional tools (macrofilaricidal drugs, vaccines, sensitive diagnostic biomarkers) that in turn rely on a comprehensive understanding of the biology of *O. volvulus* and the *O. volvulus*-human host interaction.

Because of the genetic similarity between *O. volvulus* and *Dirofilaria immitis*, the causative agent of heartworm in dogs, it is expected that the *D. immitis* orthologs of protective *O. volvulus* proteins will provide protection in dogs against infection with *D. immitis* as well. Vaccination of 'at risk' dogs is an increasingly important activity as dogs are becoming resistant to ivermectin, the current prophylactic drug for canine heartworm.

SUMMARY

The present disclosure relates to immunogenic compositions for preventing or treating infection with filarial parasites and biomarkers for diagnosing infection with filarial parasites.

Thus, disclosed herein are immunogenic compositions for preventing or treating infection with a filarial parasite, wherein the filarial parasite is *Onchocerca volvulus*, and wherein the immunogenic composition comprises at least one filarial parasite protein having at least 85%, 90%, 95%, or 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), or OVOC8227 (SEQ ID NO:30).

Also disclosed herein are immunogenic compositions for preventing infection with a filarial parasite, wherein the filarial parasite is *Dirofilaria immitis*, and wherein the immunogenic composition comprises at least one filarial parasite mature protein having at least 85%, 90%, 95%, or 98% sequence identity to the full length of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), or OVOC4230 (SEQ ID NO:32), or an ortholog thereof. In some embodiments, the ortholog comprises a filarial parasite protein having at least 85%, 90%, 95%, or 98% sequence identity to the full length of one of SEQ ID NOs:33-49.

In some embodiments, an immunogenic composition further comprises an adjuvant. In certain embodiments, the immunogenic composition comprises at least two, at least three, at least four, at least five, at least six, at least seven, at least eight, at least nine, or at least ten filarial parasite proteins. In some embodiments, the at least two filarial parasite proteins are present in the immunogenic composition in a mixture. In certain embodiments, the at least two filarial parasite proteins are present in the immunogenic composition as a fusion protein comprising the amino acid sequences of the at least two filarial parasite proteins. In some embodiments, the fusion protein optionally further comprises at least one linker sequence separating the at least two filarial parasite amino acid sequences.

Also disclosed herein are methods of preventing infection with, or transmission of, *O. volvulus*, the method comprising administering an immunogenic composition disclosed herein to a subject in need thereof, wherein the immunogenic composition prevents the infection or prevents transmission of the infection to another subject. In some embodiments, the immunogenic composition further includes an adjuvant.

In some embodiments, the immunogenic composition is administered to a subject at risk of *O. volvulus* infection, and the administration prevents infection with *O. volvulus* and/or prevents transmission of *O. volvulus*. In some embodiments, the subject is a human.

Also disclosed herein are methods of preventing an infection with *D. immitis*, the method comprising administering an immunogenic composition disclosed herein to a canine subject in need thereof, wherein the immunogenic composition prevents the infection.

In some embodiments, the immunogenic composition is administered to a subject at risk of *D. immitis* infection, and the administration prevents infection with *D. immitis*.

Also disclosed herein are methods of detecting infection with *O. volvulus*, comprising identifying in a specimen from a subject at least one filarial full length mature protein having at least 85%, 90%, 95%, or 98% sequence identity to OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395

(SEQ ID NO:15), or OVOC10384 (SEQ ID NO:13) or an immunoreactive fragment thereof.

Also disclosed herein are methods of detecting infection with *O. volvulus*, comprising identifying in the blood of a subject, antibodies to at least one filarial protein having at least 85%, 90%, 95%, or 98% sequence identity to the full length mature protein of OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC10384 (SEQ ID NO:13), OVOC8422 (SEQ ID NO:14), OVOC9988 (SEQ ID NO:31), or OVOC6395 (SEQ ID NO:15), or an immunoreactive fragment thereof.

In certain embodiments, the immunoreactive fragment is OVOC10469_Pep2 (SEQ ID NO:51), OVOC3261_Pep1 (SEQ ID NO:52), OVOC3261_Pep3 (SEQ ID NO:53), OVOC10469_Pep1 (SEQ ID NO:54), OVOC10469_Pep3 (SEQ ID NO:55), OVOC3261_Pep2 (SEQ ID NO:56), OVOC5127_Pep1 (SEQ ID NO:57), OVOC5127_Pep2 (SEQ ID NO:58), OVOC5127_Pep4, (SEQ ID NO:59), OVOC5127_Pep5 (SEQ ID NO:60), or OVOC5127_PepX (SEQ ID NO:61).

In certain embodiments, the specimen comprises blood, a skin biopsy, or urine.

In some embodiments, the method comprises at least two, at least three, at least four, at least five, at least six, at least seven, at least eight, at least nine, or at least ten filarial parasite proteins. In some embodiments, the at least two filarial parasite proteins comprise Ov16 and OVOC3261. In some embodiments, the at least four filarial parasite proteins comprise Ov16, OVOC3261, OVOC10469, and OVOC5127.

In some embodiments, the filarial protein or antibody to the filarial protein are detected by a method selected from the group consisting of ELISA, dipstick tests, lateral flow, microfluidic devices, luciferase immunoprecipitation systems, luminex, multiplex-formats, polymerase chain reaction, and microarrays.

BRIEF DESCRIPTION OF THE DRAWINGS

FIG. 1A depicts the number of *O. volvulus*-specific genes (light gray) and proteins (dark bars) identified across the stages by transcriptomic and proteomic analyses. ND denotes samples that were not analyzed. FIG. 1B depicts the number of *Wolbachia* (wOv) proteins identified across the *O. volvulus* stages.

FIG. 2A depicts a scatter plot of representative proteins with significant IgG4 reactivity in infected individuals, plotted as normalized intensity. FIG. 2B depicts scatter plots of representative proteins with significant IgG1, IgG3 and IgE responses in putatively immune individuals, plotted as ratios to normal sera. The four columns of data for each protein are, from left to right: Putatively Immune; Normal; Infected individuals; Endemic Normal. P values are represented by * (p≤0.05),  (p≤0.01), * (p≤0.001), **** (p≤0.001).

FIG. 3A: Ov16; FIG. 3B: OVOC10469; FIG. 3C: OVOC3261, FIG. 3D: OVOC5127; FIG. 3E: Ov16; FIG. 3F: Ov16+OVOC10469; FIG. 3G: Ov16+OVOC10469+OVOC3261. FIG. 3H depicts the positivity (in black) for each protein based on ROC (receiver operating curves) values. The false negatives for Ov16 (gray, boxed) can be picked up using combination of the proteins (OVOC10469, OVOC3261 and OVOC5127). The white denotes samples not assayed for that protein.

FIG. 4A: Ov-103; FIG. 4B: Ov-RAL-2; FIG. 4C: Ov-CPI-2M. Each dot represents larval recovery from an individual animal. Data presented are mean±S.D. Asterisk represents statistical difference in larval recoveries; P 0.05.

FIG. 5A depicts Ov-RAL-2/103 fusion protein expressed in *E. coli* and *P. pastoris* expressed protein. FIG. 5B depicts Ov-RAL-2/CPI-2M expressed in *E. coli*. Each dot represents larval recovery from an individual animal. Data presented are mean±S.D. Asterisk represents statistical difference in larval recoveries; P 0.05.

DETAILED DESCRIPTION

Figure 1A:
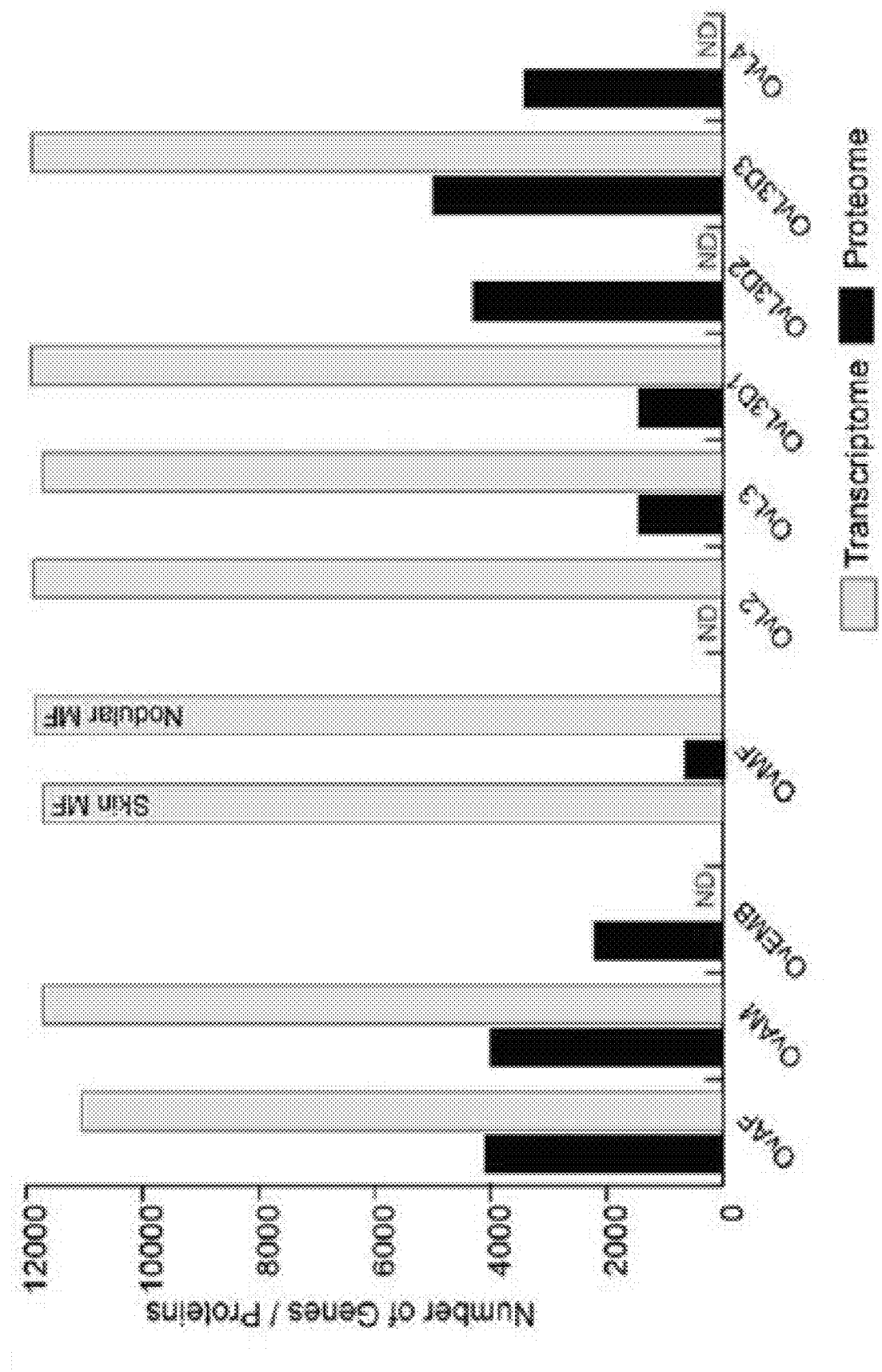
FIG. 1A-B depicts an overview of transcriptome and proteome of *Onchocerca volvulus*.

Onchocerciasis, or river blindness, caused by infection with *Onchocerca volvulus*, is a neglected tropical disease (NTD) that is associated with significant morbidity and disability in the 17 million people estimated to be infected. Infection leads to severe and disfiguring skin disease, lymphadenopathy and visual impairment (including blindness). Onchocerciasis was the first NTD targeted for control in 1974 by the World Health Organization (WHO) and is now one of the six NTDs targeted for elimination. Elimination efforts for *O. volvulus* are presently aimed by controlling transmission through ivermectin-based mass drug administration (MDA) programs, that have largely eliminated onchocerciasis in the Americas and that have made significant progress toward that goal in some regions of Africa. However, according to a new WHO evaluation, elimination would require an estimated 1.30 billion ivermectin treatments, lasting until 2045, and a recent report has suggested that onchocerciasis cannot solely be eliminated through MDA with ivermectin. Moreover, ivermectin is contraindicated in areas of marked co-endemicity with *Loa loa*, where the risk of severe adverse events is associated with high levels of circulating *Loa loa* microfilariae (mf). Furthermore, the potential for ivermectin resistance, the lack of macrofilaricidal activity by ivermectin, and the long timeline (>20 years) for transmission interruption has prompted research into the development of new tools (macrofilaricidal drugs, diagnostics, vaccines, etc.), the basis of which relies on a fundamental understanding of the parasite biology.

Humans are the only definitive host for *O. volvulus*. Because there are no existing small animal models for propagating the life cycle of *O. volvulus*, approaches that require sufficient amounts of stage-specific parasite material have been difficult, as the adult parasites must be obtained surgically from subcutaneous nodules and microfilariae from human skin. Moreover, the larval stages must be obtained from the infected blackflies—a process that to date requires feeding of newly hatched naïve black flies on infected microfiladermic humans. Nevertheless, using parasite material from most of the life cycle stages, a comprehensive profile of the stage-specific transcriptomes and proteomes of O. volvulus has been developed. Systematic comparisons across the parasite stages and across related nematodes and "immunomics" has enabled the identification of novel vaccine and diagnostic candidates.

Systems biology aims at understanding biological processes by integrating various omic's data. Compared to transcriptomic data, attaining complete coverage at the protein level is fraught with technological limitations as well as the dynamic nature of any proteome. Although a difference in transcript (RNA) and protein recovery from the various stages is expected, normalization (RPKM and spectral abundance) provides provisional evidence for relative abundance of any particular gene/protein in a given stage. Using a combination of transcriptomic and proteomic analyses comprehensive stage-specific analyses of O. volvulus was undertaken. This dataset provides an in-depth resource for understanding and analyzing the biological pathways that are critical for the development of the various stages of the parasite in the vector and human hosts, host-O. volvulus interaction, and for the identification of novel biomarkers and targets for interventions.

Natural immunity against O. volvulus can be acquired in a few individuals within affected populations; these individuals are known as putatively immune and exhibit protective immune response against L3 larvae, suggesting that E/S products released by molting larvae and/or surface proteins of L3 larvae are an important source of protective antigens. The identification of proteins that are highly expressed by the mf and that are specifically recognized by sera from protected individuals who never developed a clinically relevant infection also suggests other suitable vaccine candidates. The identification of O. volvulus-unique proteins that are adult and/or mf stage-specific identified by infected individuals, provided additional novel biomarkers needed for better mapping the prevalence of infection and for post-control surveillance.

As used herein the term "transcriptome" refers to the full range of messenger RNA, or mRNA, molecules expressed by an organism at a certain time.

As used herein, the term "proteome" refers to the entire set of proteins expressed by a genome, cell, tissue, or organism at a certain time.

The life cycle of O. volvulus includes the following stages: nodular microfilariae (NodMF), skin microfilariae (SknMF), embryos (OvEMB), larva L1 (OvL1), larva L2 (OvL2), larva L3 (OvL3), molting L3s (L3 Day 1 and L3 Day 3), larva L4 (OvL4), adult male (OvAM), and adult female (OvAF).

Analyses of transcript levels or protein abundance for each of the stages identified 363 proteins that were found as core elements by having been present across all somatic stages. Functionally, proteins involved in metabolism, cytoskeletal processes and protein modification comprised more than 50% of these core genes. Proteins shared between OvEMB and OvAF are likely to play a role in embryogenesis. Similarly, proteins identified exclusively during the L3 to L4 transition highlight the machinery required during the developmental molt, and possibly adaptation to the human host environment. Based on C. elegans RNAi data, O. volvulus homologs of C. elegans that exhibit phenotypes of embryonic lethality (EMB), larval arrest (LVA), larval lethal (LVL), molting defective (MLT), or lethal (LET) were observed to be clustered not only in embryos, microfilariae (and thereby adult females), and L3 larval stages but also in adult males. This could either be due to C. elegans being primarily a hermaphroditic organism or to differences between gene families of parasitic and free-living nematodes.

Similarly, the O. volvulus genome encodes orthologues of the most critical genes essential for molting (based on C. elegans), orthologues that appear to be highly expressed during the in vitro molting process of the L3 larvae. However, it also highlights other proteins, some of which have already been shown to be essential for molting and/or other developmental processes of filarial parasites. For example, embryogenesis and molting in filarial parasites is dependent on the activity of cathepsin L-like cysteine proteases (CPLs).

Establishment of infection in humans depends on the successful molt from L3 to L4 larvae and subsequent development into adults. During molting, CPLs are stored in the glandular esophagus and their release during molting helps breakdown the old cuticle and drives synthesis of a new cuticle by processing the pro-proteins. Comparative analyses suggest an expansion of CPL-like enzymes in the O. volvulus genome. Significant transcriptional regulation of CPL and CPZ molecules was observed in L2 and L3 larvae compared to other stages. Inferring from Brugia malayi, a related filiarial parasite, these enzymes are probably needed for the L2 to L3 molt in the black fly. Interestingly, the GO gene categories of nucleotide binding (GO:0000166), molecular function (GO:0003674), and phosphoprotein phosphatase activity (GO:0004721), were the most represented categories of differentially expressed genes during L2/L3 and L3/L4 molting. Gene set enrichment analysis (GSEA) identified immunologically important classes of molecules as enriched in L3 larval stages, and a set of extracellular matrix-related genes distinct from the ones overexpressed in adult female worms. The collagens making up the cuticle are regulated by a number of factors, one of which is prolyl-4 hydroxylase, a family that is expanded in the O. volvulus genome, and that is expressed in a stage-specific manner.

In contrast to those gene families upregulated during development, nuclear hormone receptors (NHR), known to play an important role in other nematode developmental processes, are comparatively less expanded in O. volvulus but still appear to play a role in molting and embryogenesis, as seen in B. malayi. Indeed the O. volvulus ecdysone receptor (EcR, Accession No. OVOC9104) and NHR RXR (Accession No. OVOC2435) are upregulated during the L3 to L4 developmental molt. Furthermore GSEA indicate enrichment of OVOC351 and OVOC353 (other potential NHRs) in adult female worms (p-value<0.0001, FDR<1%). Similarly, the orthologues of the C. elegans NHRs—nhr-6 (OVOC8200), nhr-23 (OVOC464), nhr-25 (OVOC2839), nhr-41 (OVOC4741) and nhr-85 (OVOC827)—known to be involved in molting and metamorphosis, are present in the O. volvulus genome and detected as transcripts or proteins during the in vitro molting of L3 to L4. In addition, NHRs implicated in neural differentiation (OVOC635, OVOC3708) and sex determination (OVOC5276) were upregulated in the molting stages reflecting their probable role in molting, growth, and sex determination.

Protein OVOC2265 has a rather unique expression profile in the nodular microfilariae (mf) that corresponded with the proteome of embryonic stages. Among the embryo-enriched transcripts and proteins, OVOC11613 (immunodominant antigen or major antigen), and OVOC9384 (Oveg1) have been shown to be related to embryogenesis as well.

The *O. volvulus* sequences disclosed here correspond to the WS245 release of the genome by WormBase. The *D. immitis* sequences disclosed herein correspond to the WPBS1 release of the genome by WormBase. Subsequent genome releases by WormBase may have nucleotide or amino acid revisions.

I. Biomarkers

Thus provided herein are biomarkers for infection with a filarial parasite. In certain embodiments, the filarial parasite is *O. volvulus*.

In certain embodiments, if the filarial parasite is *O. volvulus*, the biomarker is a protein having at least 85%, at least 90%, at least 95%, or at least 98% sequence identity to the full length mature protein of OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC10384 (SEQ ID NO:13), OVOC8422 (SEQ ID NO:14), or OVOC6395 (SEQ ID NO:15).

In addition, the biomarker can also include proteins and peptides sharing a sequence identity or substantial sequence identity to the biomarker proteins provided herein.

As used herein, "sequence identity" or "identity" in the context of two protein or peptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art.

The term "substantial identity" in the context of a protein or peptide indicates that a protein or peptide comprises a sequence with at least 85%, 86%, 87%, 88%, 89%, 90%, 91%, 92%, 93%, or 94%, or even 95%, 96%, 97%, 98%, or 99% sequence identity to the reference sequence over a specified comparison window. In certain embodiments, optimal alignment is conducted using the homology alignment algorithm of Needleman and Wunsch (Needleman and Wunsch, JMB, 48:443, 1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, also provided herein are proteins and peptides that are substantially identical to the proteins and peptides presented herein.

In certain embodiments, the term "sequence identity" refers to identity across the entire amino acid sequence of one of SEQ ID NOs:1-66 but can include proteins or peptides which have additional amino acids at the C-terminus or N-terminus of the protein or peptide and which have at least 85%, at least 90%, at least 95%, or at least 98% sequence identity to the portion of the sequence which is the same length as the disclosed sequences.

Accordingly, some embodiments disclosed herein comprise a method of diagnosing an infection with a filarial parasite comprising: (a) providing a blood sample from at least one subject suspected of having a filarial parasite infection; and (b) contacting the sample with at least one protein selected from OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395 (SEQ ID NO:15) or OVOC10384 (SEQ ID NO:13); wherein if the sample contains specific antibodies which bind to the at least one protein, the subject has an active filarial parasite infection. In certain embodiments, the method includes contacting the sample with at least two, at least three, at least four, at least five, at least six, at least seven, at least eight, at least nine, or at least ten filarial parasite proteins.

Additionally, some embodiments disclosed herein comprise a method of diagnosing an infection with a filarial parasite comprising: (a) providing a tissue or fluid sample from at least one subject suspected of having an filarial parasite infection; (b) providing a binding agent which binds to at least one filarial parasite-associated protein selected from OVOC10469 (SEQ ID NO:1), OVOC11950 (SEQ ID NO:2), OVOC10602 (SEQ ID NO:3), OVOC3261 (SEQ ID NO:4), OVOC5127 (SEQ ID NO:5), OVOC8491 (SEQ ID NO:6), OVOC6759 (SEQ ID NO:7), OVOC451 (SEQ ID NO:8), OVOC12329 (SEQ ID NO:9), OVOC3337 (SEQ ID NO:10), OVOC10264 (SEQ ID NO:11), OVOC4230 (SEQ ID NO:12), OVOC8422 (SEQ ID NO:14), OVOC6395 (SEQ ID NO:15) OVOC10384 (SEQ ID NO:13); and (c) detecting the proteins, individually and/or in combination, associated with the filarial parasite infection in the subject and contained in the sample; wherein if the sample contains at least one filarial parasite-associated protein, the subject has an active filarial parasite infection. In certain embodiments, the fluid sample is urine, blood, serum, plasma, or a skin biopsy. In some embodiments, the method includes detecting at least two, at least three, at least four, at least five, at least six, at least seven, at least eight, at least nine, or at least ten filarial parasite proteins.

Also disclosed herein are immunoreactive fragments of filarial parasite proteins which can be used in the methods disclosed herein. The immunoreactive fragments include, but are not limited to, OVOC10469_Pep2 (SEQ ID NO:51), OVOC3261_Pep1 (SEQ ID NO:52), OVOC3261_Pep3 (SEQ ID NO:53), OVOC10469_Pep1 (SEQ ID NO:54), OVOC10469_Pep3 (SEQ ID NO:55), OVOC3261_Pep2 (SEQ ID NO:56), OVOC5127_Pep1 (SEQ ID NO:57), OVOC5127_Pep2 (SEQ ID NO:58), OVOC5127_Pep4, (SEQ ID NO:59), OVOC5127_Pep5 (SEQ ID NO:60), and OVOC5127_PepX (SEQ ID NO:61).

Ideally, several methods, including ELISA, dipstick tests, lateral flow, microfluidic devices, luciferase immunoprecipitation systems (LIPS), and microarrays can be used to detect filarial parasite-associated biomarkers in patients with filarial parasite infections.

ELISA is a widely used method for the detection of specific antibodies and proteins in a biological sample. It involves the immobilization of an antibody (primary antibody), or an antigen, to a solid support, such as plastic microplates, and detecting binding of components of a patient sample to the immobilized antibody or antigen, followed by the addition of secondary antibody or antibodies, the latter usually being conjugated to a detectable moiety in order to facilitate measurement.

Hence, according to some embodiments, the immune affinity procedure may be an ELISA immunoassay selected from the group consisting of direct enzyme-linked immunosorbent assays, indirect enzyme-linked immunosorbent assays, direct sandwich enzyme-linked immunosorbent assays, indirect sandwich enzyme-linked immunosorbent assays, and competitive enzyme-linked immunosorbent assays.

In one embodiment, detection is effected through capture ELISA. Capture ELISA (also known as "sandwich" ELISA) is a sensitive assay to quantify picogram to microgram quantities of substances such as hormones, cell signaling chemicals, infectious disease antigens and cytokines. This type of ELISA is particularly sought after when the substance to be analyzed may be too dilute to bind to the microtiter plate (such as a protein in a cell culture supernatant) or does not bind well to plastics (such as a small organic molecule). Optimal dilutions for the capture antibody, samples, controls, and detecting antibodies as well as incubation times are determined empirically and may require extensive titration. Ideally, one would use an enzyme-labeled detection antibody. However, if the detection antibody is unlabeled, the secondary antibody should not cross-react with either the coating antibody or the sample. Optimally, the appropriate negative and positive controls should also be included.

Detection of the biomarkers, or of any fragment or derivative thereof, may be performed using antibodies specific to said biomarkers. These antibodies may be labeled directly or indirectly by a detectable moiety.

As used herein in the specification, the term "detectable moiety" refers to any element, molecule, or a portion thereof, the presence, absence or level of which may be monitored directly or indirectly. One example includes radioactive isotopes. Other examples include enzymes which can catalyze color or light emitting (luminescence) reactions, fluorophores, and gold or magnetic labels. The detection of the detectable moiety can be direct provided that the detectable moiety is itself detectable (i.e. can be directly visualized or measured), such as, for example, in the case of fluorophores. Alternatively, the detection of the detectable moiety can be indirect. In the latter case, a second moiety that reacts with the detectable moiety, itself being directly detectable is preferably employed. The detectable moiety may be inherent to the antibody. For example, the constant region of an antibody can serve as an indirect detectable moiety to which a secondary antibody having a direct detectable moiety can specifically bind.

Thus, secondary antibodies are particular suitable means for the detection of the anti-biomarker antibody. This secondary antibody may be itself conjugated to a detectable moiety. One of the ways in which an antibody can be detectably labeled is by linking the same to an enzyme. The enzyme, in turn, when exposed to an appropriate substrate, will react with the substrate in such a manner as to allow its detection, for example, by producing a chemical moiety, which can be detected, for example, by spectrophotometric, fluorometric, or by visual means. Enzymes which may be used to label the antibody include, but are not limited to, horseradish peroxidase, alkaline phosphatase, malate dehydrogenase, staphylococcal nuclease, δ-5-steroid isomerase, yeast alcohol dehydrogenase, α-glycerophosphate dehydrogenase, triose phosphate isomerase, asparaginase, glucose oxidase, beta-galactosidase, ribonuclease, urease, catalase, glucose-6-phosphate dehydrogenase, glucoamylase and acetylcholinesterase, or any other enzyme which can be conjugated to an antibody and its reaction with a substrate, measured or detected.

The detection may be accomplished by colorimetric methods, which employ a chromogenic substrate for the enzyme. Detection may also be accomplished by visual comparison of the extent of enzymatic reaction of a substrate in comparison with similarly prepared standards.

The solid support to which the first antibody is bound may be any water-insoluble, water-insuspensible, solid support. Examples of suitable solid support include, but are not limited to, large beads (e.g., of polystyrene), filter paper, slides, chips, test tubes, and microtiter plates. The first antibody may be bound to the solid support by covalent bonds or by adsorption. The advantage in using a solid support is that no centrifugation step is needed for the separation of the solid and liquid phase.

The solid support mentioned above may include polymers, such as polystyrene, agarose, SEPHAROSE®, cellulose, glass beads and magnetizable particles of cellulose or other polymers. The solid-support can be in the form of large or small beads or particles, tubes, plates, slides, chips or other forms.

As a solid support, a test tube, the inner walls of a test tube or a microtiter plate are coated with a first antibody, e.g., antibodies specific to a peptide or protein disclosed herein, or of any fragment or derivative thereof.

In a further embodiment, dipstick assays may be used to detect filarial parasite biomarkers. Dipstick assays use the lateral flow format, wherein capture antibodies are striped or banded onto nitrocellulose membrane and a wicking pad draws the sample up through the dipstick, whereby the filarial parasite biomarkers interact with a filarial parasite biomarker antibody, or combination of antibodies. Other antibodies specific to filarial parasites, or other proteins of interest may be included. Subsequent analysis of enzyme activity and protein quantity may be done using standard methods known to a person skilled in the art, or as discussed above regarding ELISAs.

In another preferred embodiment, microfluidic devices, which may also be referred to as "lab-on-a-chip" systems, biomedical micro-electro-mechanical systems (bioMEMs), or multicomponent integrated systems, may be used for detecting filarial parasite biomarkers. Such systems miniaturize and compartmentalize processes that allow for detection of filarial parasite biomarkers, and other processes.

Array-based assays and bead-based assays may be used with microfluidic device. For example, a binding agent can be coupled to beads and the binding reaction between the beads and filarial parasite biomarker can be performed in a microfluidic device. Multiplexing, or detecting more than one filarial parasite biomarker at once, can also be performed using a microfluidic device. Different compartments can comprise different binding agents for different populations of filarial parasite biomarkers, where each population has a different bio-signature.

In another embodiment, microarrays are used to detect filarial parasite biomarkers. Microarrays are typically small, high throughput chips generally made of a solid support structure, typically glass slides, nitrocellulose, or microtiter plates. Generally, antibodies to specific biomarker are bound to the solid support; however, other molecules, such as, but not limited to other proteins, aptamers, DNA, RNA, sugars or lipids can be bound to the solid surface as well. Detection of the captured biomarker can also be accomplished as discussed above for ELISA detection.

In another further embodiment, recognition of filarial parasite specific biomarker is achieved through an immune affinity procedure such as Western blot, immuno-precipitation, FACS, biochip array, lateral flow, time resolved fluorometry, ECL procedures, luminex, LIPS, multiplex-immunoassay formats or any procedure based on immune recognition known to one of ordinary skill in the art.

II. Immunogenic Compositions

Also provided herein are immunogenic compositions for preventing infection with, or preventing transmission of, a filarial parasite. In certain embodiments, the filarial parasite is O. volvulus. In other embodiments, the filarial parasite is D. immitis. As used herein, "preventing transmission of" refers to the inability of an infected subject, who has been immunized with an immunogenic disclosed herein, to transmit infectious parasites to another subject via an intermediate vector.

In certain embodiments, the filarial parasite is O. volvulus, and the immunogenic composition comprises as least one protein having at least 85%, at least 90%, at least 95%, or at least 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), OVOC4230 (SEQ ID NO:32), or an immunogenic fragment thereof, or a nucleic acid encoding the protein. In certain embodiments, the filarial parasite immunogenic composition for preventing infection with, or preventing transmission of, O. volvulus is not OVOC9988 (Ov-RAL-2), OVOC4230 (Ov-103), or OVOC7453 related (Ov-CPI-2M). In some embodiments, the immunogenic composition includes at least two, at least three, at least four, at least five, at least six, at least seven, at least eight, at least nine, or at least ten filarial parasite proteins. The immunogenic composition can comprise the filarial parasite proteins in a mixture or as fusion proteins which include sequences from two or more filarial parasite proteins assembled in a single polypeptide sequence. If multiple filarial proteins are assembled into a fusion protein, one or more linker sequences can be included.

In other embodiments, the filarial parasite is D. immitis, and the immunogenic composition comprises at least one protein having at least 85%, at least 90%, at least 95%, or at least 98% sequence identity to the full length mature protein of OVOC8619 (SEQ ID NO:16), OVOC7083 (SEQ ID NO:17), OVOC4111 (SEQ ID NO:18), OVOC1808 (SEQ ID NO:19), OVOC11598 (SEQ ID NO:20), OVOC3901 (SEQ ID NO:21), OVOC10819 (SEQ ID NO:22), OVOC5395 (SEQ ID NO:23), OVOC12235 (SEQ ID NO:24), OVOC7908 (SEQ ID NO:25), OVOC7430 (SEQ ID NO:26), OVOC8936 (SEQ ID NO:27), OVOC5806 (SEQ ID NO:28), OVOC4665 (SEQ ID NO:29), OVOC8227 (SEQ ID NO:30), OVOC9988 (SEQ ID NO:31), or OVOC4230 (SEQ ID NO:32), an ortholog thereof, or a nucleic acid encoding the protein or ortholog. In some embodiments, the ortholog comprises one of the proteins of Table 6, or an immunogenic fragment thereof. In some embodiments, the immunogenic composition includes at least two, at least three, at least four, at least five, at least six, at least seven, at least eight, at least nine, or at least ten filarial parasite proteins. The immunogenic composition can comprise the filarial parasite proteins in a mixture or as fusion proteins which include sequences from two or more filarial parasite proteins assembled in a single polypeptide sequence.

As used herein, the term "immunogenic composition" refers to a substance which induces a specific immune response against an immunogen (protein) in an individual who is in need of an immune response to the immunogen. As used herein the term "immunogen" refers to any substrate that elicits an immune response in a host. Thus, the disclosed immunogenic compositions comprising filarial parasite proteins are useful for inducing an immune response against a filarial parasite. In certain embodiments, the immune response is a protective immune response. In other embodiments, the immune response is a therapeutic immune response. A non-limiting example of an immunogenic composition is a vaccine.

In certain embodiments, the immunogenic composition comprises a protein disclosed herein along with additional sequences to enhance immunogenicity.

In certain embodiments, the immunogenic composition is a fusion protein which includes several filarial parasite proteins. In some embodiments, the immunogenic composition is a mixture of one or more filarial parasite proteins. In some embodiments, the immunogenic composition includes at least two, at least three, at least four, at least five, at least six, at least seven, at least eight, at least nine, or at least ten filarial parasite proteins.

Certain amino acid sequences disclosed herein may include a signal sequence. As is understood by a person of skill in the art, expressed filarial proteins useful as immunogenic composition or biomarkers disclosed herein will not include a signal sequence. Thus, in certain embodiments, the amino acid sequences are referred to as "mature" proteins, which are proteins without a signal sequence. In some embodiments, the protein sequence will be recited as less than the entire amino acid sequence disclosed herein to reflect the absence of the signal sequence.

The disclosed filarial parasite immunogenic compositions and proteins include conservative variants of the proteins and fusion proteins. A conservative variant refers to a peptide or protein that has at least one amino acid substituted by another amino acid, or an amino acid analog, that has at least one property similar to that of the original amino acid from an exemplary reference peptide. Examples of properties include, without limitation, similar size, topography, charge, hydrophobicity, hydrophilicity, lipophilicity, covalent-bonding capacity, hydrogen-bonding capacity, physicochemical property, or the like, or any combination thereof. A conservative substitution can be assessed by a variety of factors, such as, e.g., the physical properties of the amino acid being substituted (Table 1) or how the original amino acid would tolerate a substitution (Table 2). The selections of which amino acid can be substituted for another amino acid in a peptide disclosed herein are known to a person of ordinary skill in the art. A conservative variant can function in substantially the same manner as the exemplary reference peptide, and can be substituted for the exemplary reference peptide in any aspect of the present specification.

TABLE 1

Amino Acid Properties

| Property | Amino Acids |
|---|---|
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

A filarial parasite immunogenic composition can also comprise conservative variants to the disclosed proteins or fusion proteins. In aspects of this embodiment, a conservative variant of a filarial parasite protein or fusion protein can be, for example, an amino acid sequence having at least 75%, at least 80%, at least 85%, at least 90%, at least 95%, at least 97%, at least 98%, or at least 99% amino acid sequence identity to the filarial parasite protein or fusion protein. In other aspects of this embodiment, a conservative variant of a filarial parasite protein or fusion protein can be, for example, an amino acid sequence having at most 75%, at most 80%, at most 85%, at most 90%, at most 95%, at most 97%, at most 98%, or at most 99% amino acid sequence identity to the filarial parasite protein or fusion protein.

In other embodiments, a conservative variant of a filarial parasite protein or fusion protein amino acid sequence can have, for example, 1, 2, 3, 4, 5, 6, 7, 8, 9, 10, 11, 12, 13, 14, 15, or more conservative substitutions, to the amino acid sequence of the filarial parasite protein or fusion protein. In other embodiments, a conservative variant of a filarial parasite protein or fusion protein amino acid sequence can be, for example, an amino acid sequence having at least 1, at least 2, at least 3, at least 4, at least 5, at least 6, at least 7, at least 8, at least 9, at least 10, at least 11, at least 12, at least 13, at least 14, or at least 15 conservative substitutions to the amino acid sequence of the filarial parasite protein or fusion protein. In yet other embodiments, a conservative variant of a filarial parasite protein or fusion protein amino acid sequence can be, for example, an amino acid sequence having at most 1, at most 2, at most 3, at most 4, at most 5, at most 6, at most 7, at most 8, at most 9, at most 10, at most 11, at most 12, at most 13, at most 14, or at most 15 conservative substitutions to the amino acid sequence of the filarial parasite protein or fusion protein. In further embodiments, a conservative variant of a filarial parasite protein or fusion protein amino acid sequence can be, for example, an amino acid sequence having from 1 to 15, 2 to 15, 3 to 15, 4 to 15, 5 to 15, 6 to 15, 7 to 15, 1 to 12, 2 to 12, 3 to 12, 4 to 12, 5 to 12, 6 to 12, 7 to 12, 1 to 10, 2 to 10, 3 to 10, 4 to 10, 5 to 10, 6 to 10, 7 to 10, 1 to 8, 2 to 8, 3 to 8, 4 to 8, 5 to 8, 6 to 8, 1 to 6, 2 to 6, 3 to 6, 4 to 6, 1 to 4, 2 to 4, or 1 to 3 conservative substitutions to the amino acid sequence of the filarial parasite protein or fusion protein.

In certain embodiments, the immunogenic compositions further comprise or are administered with an adjuvant. Adjuvants suitable for use in animals include, but are not limited to, Freund's complete or incomplete adjuvants, Sigma Adjuvant System (SAS), and Ribi adjuvants. Adjuvants suitable for use in humans include, but are not limited to, MF59® (an oil-in-water emulsion adjuvant, Novartis AG); MONTANIDE® ISA 51 or 720 (a mineral oil-based or metabolizable oil-based adjuvant, SEPPIC); aluminum hydroxide, -phosphate, or -oxide; HAVLOGEN® (an acrylic acid polymer-based adjuvant, Intervet Inc.); polyacrylic acids; oil-in-water or water-in-oil emulsion based on, for example a mineral oil, such as BAYOL™ or MARCOL™ (Esso Imperial Oil Limited), or a vegetable oil such as vitamin E acetate; a saponin; CpG oligodeoxynucleotide adjuvants; or a glucagon-like peptide (GLP) adjuvant. However, components with adjuvant activity are widely known and, generally, any adjuvant may be utilized that does not adversely interfere with the efficacy or safety of the immunogenic composition.

Immunogenic compositions according to the various embodiments disclosed herein can be prepared and/or marketed in the form of a liquid, frozen suspension, or in a lyophilized form. Typically, vaccines and/or immunogenic compositions contain a pharmaceutically acceptable carrier or diluent customarily used for such compositions. Carriers include, but are not limited to, stabilizers, preservatives, and buffers. Suitable stabilizers are, for example SPGA, TWEEN® compositions (such as are available from A.G.

Scientific, Inc.), carbohydrates (such as sorbitol, mannitol, starch, sucrose, dextran, glutamate, or glucose), proteins (such as dried milk serum, albumin, or casein), or degradation products thereof. Examples of suitable buffers include alkali metal phosphates. Suitable preservatives include thimerosal, merthiolate, and gentamicin. Diluents include water, aqueous buffer (such as buffered saline), alcohols, and polyols (such as glycerol).

Also disclosed herein are methods for inducing an immune response to a filarial parasite using the disclosed proteins. Generally, the vaccine and/or immunogenic composition may be administered subcutaneously, intradermally, submucosally, intranasally, or intramuscularly in an effective amount to prevent infection from the filarial parasite and/or treat an infection from the filarial parasite. An effective amount to prevent infection is an amount of immunizing protein that will induce immunity in the immunized animals against challenge by infective stage larvae or microfilariae such that infection is prevented or the severity is reduced. Immunity is defined herein as the induction of a significant higher level of protection in a subject after immunization compared to an unimmunized group. An effective amount to treat an infection is an amount of immunizing protein that induces an appropriate immune response against filarial parasite such that severity of the infection is reduced.

Protective immune responses can include humoral immune responses and cellular immune responses. Protection against filarial parasite is believed to be conferred through serum antibodies (humoral immune response) directed to the surface proteins and/or proteins secreted during the early development in the human host, probably through antibody-dependent cellular cytotoxicity (ADCC) and cell-mediated immune responses. Cellular immune responses are useful in protection against filarial parasite infection with CD4+ T cell responses of the Th1, Th2 and/or Th17 type being particularly important. Additionally, the disclosed proteins and/or immunogenic compositions can be administered using immunization schemes known by persons of ordinary skill in the art to induce protective immune responses. These include a single immunization or multiple immunizations in a prime-boost strategy. A boosting immunization can be administered at a time after the initial, prime, immunization that is days, weeks, months, or even years after the prime immunization. In certain embodiments, a boost immunization is administered 2 weeks, 1 month, 2 months, 3 months, 4 months, 5 months, or 6 months or more after the initial prime immunization. Additional multiple boost immunizations can be administered such as weekly, every other week, monthly, every other month, every third month, or more. In other embodiments, the boost immunization can be administered every 3 weeks, every 4 weeks, every 5 weeks, every 6 weeks, every 7 weeks, every 8 weeks, every 9 weeks, every 10 weeks, every 11 weeks, or every 12 weeks. In certain embodiments, boosting immunizations can continue until a protective anti-filarial parasite antibody titer is seen in the subject's serum. In certain embodiments, a subject is given one boost immunization, two boost immunizations, three boost immunizations, or four or more boost immunizations, as needed to obtain a protective antibody titer. In other embodiments, the adjuvant in the initial prime immunization and the adjuvant in the boost immunizations are different.

Further, in various formulations of the proteins and/or immunogenic compositions, suitable excipients, stabilizers, and the like may be added as are known by persons of ordinary skill in the art.

The disclosed proteins, immunogenic compositions, and methods may be used to prevent filarial parasite infection in a subject susceptible thereto such as, but not limited to, a human, or a domesticated animal.

EXAMPLES

Example 1. Transcriptome and Proteome of *Onchocerca volvulus*

Parasite and Serum Samples. Parasite materials used for RNAseq and proteomic analyses were collected at the research facility at the Tropical Research Station, Kumba, Cameroon, and in Ecuador and Guatemala. Written informed consent was obtained. In cases of illiteracy, the participant made a thumbprint and a literate witness signed. Institutional Review Board (IRB) approvals were obtained from the National Institutes of Health, the New York Blood Center and the Tropical Research Station, Kumba. The individuals who consented to participate in the study were born, or had resided for more than 10 years, in endemic areas, and were confirmed to have, or not, microfilaria in their skin snips as well as any other clinical symptoms of disease, such as dermatitis, nodules and/or ocular lesions. In order to identify the putatively immune individuals, biopsies of the mf—individuals were also tested for the presence of the 150-mer DNA repeats specific for *O. volvulus* using PCR and Southern blot. Samples were collected before the introduction of ivermectin or from subjects that had not received ivermectin treatment prior to the studies. Adult worm samples were obtained from nodules excised during nodulectomies. Briefly, individual and cleaned freshly obtained nodules were immersed in 0.5% collagenase (Sigma Aldrich, grade IV) in RPMI-1640 containing 10% FCS supplemented with 200 units of penicillin and 200 µg/mL streptomycin. The flat tubes containing the nodule were then placed in a rocking water bath and incubated at 35° C. until the tissue was digested completely. Alternatively, frozen nodules were thawed, cleaned and digested with LIBERASE® TL (Roche) in Hanks Balanced Salt Solution (HBSS) supplemented with 3 mM $CaCl_2$. When digested, the liberated adult worms were unraveled from residual tissue with mounted needles under a dissecting scope, and then washed in several changes of RPMI-1640 or HBSS. The cleaned adult worms were stored at −80° C. until use.

L3 larvae were produced at the Tropical Medicine Research Station, Kumba, Cameroon. They were obtained from *Simulium damnosum* flies 7-8 days after infection with skin microfilariae. After dissection and washing, the larvae were cryopreserved and shipped to the USA. Fresh L3 larvae were also cultured in vitro in groups of 10 larvae in 96-well plates containing a 1:1 mixture of Iscove's modified Dulbecco medium and NCTC-135, 20% FCS and antibiotic-antimycotic (Life Technologies, Gaithersburg, MD) for 3-days at 37° C. Larvae were collected after 1, 2 or 3 days in culture, washed with Tris-EDTA and snap frozen in liquid nitrogen.

Nodular and skin microfilariae were also purified. Embryonic stages were purified from mf and eggs that were extruded into the medium during the cleaning process. The medium was collected and centrifuged at 1000 rpm for 10 min at room temperature. The pellet containing the mix of microfilariae and embryonic stages was resuspended and layered on LSM (MP Biomedicals, CA) and centrifuged at 500 rpm for 15 min with the brake off. The purified embryonic stages that formed the pellet were washed and stored at −80° C. until use.

Transcriptome Sequencing, Assembly and Analyses. High-throughput transcriptome data were generated from the RNA of *O. volvulus* stages: nodular microfilariae (NodMF), skin microfilariae (SknMF), L2 (OvL2), L3 (OvL3), L3 day 1 (OvL3D1), L3 day 3 (OvL3D3), adult male (OvAM), and adult female worms (OvAF). For all larval stages and adult worms, RNA was prepared using TRIzol® and lysing matrix D (1.4-mm ceramic spheres) and a FASTPREP24® (MP Biomedicals). RNA-seq libraries were prepared following the RNAseq protocols of the Illumina mRNA-Seq Sample Prep kit and the Illumina TRUSEQ® kit. Transcriptome libraries were sequenced on Illumina HiSeq 2000 machines. De novo assembly was done and is reproduced here with slight modifications. Reads were trimmed of low quality regions (<13), and only those with an average quality of 20 or more were used. Illumina primers were removed from the sequences following a parallel BLASTN of the reads against HiSeq TrueSeq adapters. Resulting reads were assembled with the ABySS software (Genome Sciences Centre) using various kmer (k) values (every fifth from 21 to 91). Because the ABySS assembler tends to miss highly expressed transcripts, the SOAPdenovo-Trans assembler was also used, again with odd kmers from 21-91. The resulting assemblies were joined by an iterative BLAST and cap3 assembler. Coding sequences (CDS) were extracted using an automated pipeline based on similarities to known proteins or by obtaining CDS containing a signal peptide. CDS and their protein sequences were mapped into a hyperlinked Excel spreadsheet. Signal peptide, transmembrane domains, furin cleavage sites, and mucin-type glycosylation were determined with software from the Center for Biological Sequence Analysis (Technical University of Denmark). Reads were mapped into the contigs using BLASTN with a word size of 25, masking homonucleotide decamers and allowing mapping up to three different CDS if the BLAST results had the same score values. Genes that had blast scores <30% of max possible score (self blast) in other nematodes with an e-value greater than 1E-05 were considered as 'unique'. To be *O. volvulus* unique, the genes were compared with the genomes of *O. flexuosa* and *O. ochengi*. Automated annotation of proteins was based on a vocabulary of nearly 290 words found in matches to various databases, including Swissprot, Gene Ontology, KOG, Pfam, and SMART, Refseq-invertebrates and a subset of the GenBank sequences containing nematode protein sequences, as well as the presence or not of signal peptides and transmembrane domains. Protein repeats were analyzed using repseq and reptile (www.reptile.unibe.ch) algorithms. Further manual annotation was done as required.

Transcriptome data (RPKM) from Excel spreadsheets was imported into JMP Genomics (SAS, Inc.) for general assessment of distribution analyses, correlations, principal component analyses, analysis of variation (ANOVA), hierarchical clustering, and heatmap generation, parallel co-ordinate plots. Heatmaps of clustering analyses were also done in R using array of packages. Differential expressing of genes was analysed using DESeq. Two replicate samples Ov1F (male) and Ov4F (female), were observed to not be exclusively male or female (pre-analyses) and were excluded from all stage-specific analyses. However, they were used for differential expression analyses with the rationale that any contaminating female transcripts present in the male sample would result in the differentially expressed genes with lower adjusted p-values to drop off and thus enriching for highly expressed genes. Likewise, any male transcripts in the female (including contributions from stored sperm and embryos) would lead to drop-off of lower range of genes and selecting for the most highly regulated genes.

Protein Depletion, Denaturation, Digestion, and Desalting. For proteomic analyses, additional stages of embryos (OvEMB), L3D2 (OvL3D2), and L4 larvae (OvL4) were also analyzed. Total soluble proteins from all the stages were extracted using the UPX universal protein extraction kit (Protein Discovery) as per manufacturer's instructions and quantified using PIERCE® BCA assay (ThermoFisher Scientific). Extracted protein samples were prepared for digestion using the filter-assisted sample preparation (FASP) method. Briefly, the samples were suspended in 1% SDC, 50 mM Tris-HCl, pH 7.6, 3 mM DTT, sonicated briefly, and incubated in a Thermo-Mixer at 40° C., 1000 RPM for 20 min. Samples were centrifuged to clarify and the supernatant was transferred to a 30 kD MWCO device (Millipore) and centrifuged at 13000×g for 30 min. The remaining sample was buffer exchanged with 1% SDC, 100 mM Tris-HCl, pH 7.6, then alkylated with 15 mM iodoacetamide. The SDC concentration was then reduced to 0.1%. Samples were digested overnight using trypsin at an enzyme:substrate ratio of 1:100 at 37° C. in a Thermo-Mixer at 1000 RPM. Digested peptides were collected by centrifugation. Twenty micrograms of the digested peptides were desalted using reversed phase stop-and-go extraction (STAGE) tips. Peptides were eluted with 80% acetonitrile, 0.2% trifluoroacetic acid and lyophilized in a SPEEDVAC® (ThermoFisher) to near dryness, approximately 1 hr.

Protein Array Construction. The following cDNA libraries from OvAM (SAW98MLW-OvAM), OvAF (SAW98MLW-OvAF), OvL2 (SAW98MLW-OvL2), OvL3 (SAW94WL-OvL3), molting L3 (SL96MLW-OvML3), and MF (SAW98MLW-OvMf) were obtained from the NIH/NIAID Filariasis Research Reagent Resource Center (www.filariasiscenter.org) and used to amplify selected gene products. Molting larvae transcripts that were not amplified successfully from the cDNA libraries were subsequently obtained from oligodT cDNA prepared from RNA purified from OvL3D1, OvL3D2 or OvL3D3 (SUPERSCRIPT® µl First-Strand Synthesis System, Invitrogen). In vivo recombination cloning was performed. Briefly, PCR primers were designed as 40 mer oligonucleotides with 20 sequence specific bases and a 20-base adapter sequence. The adapter sequences were designed to be homologous to the cloning site of the linearized T7 expression vector pXT7 and allow the PCR products to be cloned by homologous recombination in *E. coli* DH5a cells. PCR reactions were set up using HOT MASTER MIX® (5 Prime) plus DMSO (5%). The recommended cycling conditions were used and PCR products were checked for correct size using an agarose gel. PCR products were mixed with linearized pXT7 vector and were transformed into DH5a competent cells. DNA was purified using QIAPREP 96 Turbo® Miniprep Kit (Qiagen). Resulting clones were checked for insert on an agarose gel and were sent for sequencing (Retrogen).

Chip Fabrication. Proteins were expressed using a coupled in vitro transcription and translation (IVTT) system, *E. coli* based cell-free Rapid Translation System (RTS) 100 High Yield Kit (5 Prime), from the *O. volvulus* expressible clone library following the manufacturer's instructions with the exception of adding detergent to the IVTT master mix at a final concentration of 0.1% Brij 78. Shortlisted *O. volvulus* proteins were synthesized using IVTT in disulfide-bond folded formats and printed onto an array. Known immunogenic proteins (purified recombinant proteins) were also printed as positive controls.

Approximately 1 nL of unpurified IVTT reactions were spotted onto 8-pad nitrocellulose coated ONCYTE® Avid Slides (GraceBio Labs) using an OmniGrid Accent microarray printer (Digilab) equipped with an Avid™ 946 Printhead and 946MP4 Spotting Pins (ArrayIt). Each IVTT expressed protein includes an N-terminal 10× polyhistidine (HIS) epitope tag and C-terminal hemagglutinin (HA) epitope tag. Microarray chip printing and protein expression were quality checked by probing random slides with mouse anti-polyHIS (Sigma), rat anti-HA (Roche) and rabbit anti-*E. coli* (LifeSpan BioSciences). Antibodies were diluted 1:1,000 in a 3 mg/mL *E. coli* DH5a lysate solution in protein arraying buffer (GVS Filter Technology) and incubated at room temperature for 30 min. Chips, FAST® Slide Holders (GVS Filter Technology) and FAST® Slide Incubation Chambers (GVS Filter Technology) were assembled and nitrocellulose pads were hydrated using 100 µL blocking buffer for 30 min at room temperature with rocking. Blocking buffer was removed, pre-incubated antibodies were added and chips were incubated for 2 hr at room temperature, washed three times with 1× TBS-0.05% TWEEN® 20, followed by incubation with Cy5-conjugated goat anti-mouse IgG Fcγ, Cy5-conjugated goat anti-rat IgG Fcγ or Cy5-conjugated goat anti-rabbit IgG Fcγ (Jackson ImmunoResearch) diluted 1:400 in blocking buffer for 1 hr at room temperature with agitation. Chips were washed three times with 1×TBS-0.05% Tween 20, three times with 1×TBS, and once with water. Chips were air dried by centrifugation at 500×g for 10 min, stored in a light proof desiccator for at least 2 hr and scanned on a GENEPIX® 4300 with Autoloader (Molecular Devices) using the 635 nm laser. Resulting 16-bit TIFF images were quantified using GENEPIX® Pro Microarray Analysis Software (Molecular Devices) and a GENEPIX® Array List (GAL) file. Spot and background intensities were measured and median spot values minus local background (M635-B) values were exported as comma delimited file (CSV).

Probing Samples. Serum samples were diluted 1:100 for IgG and 1:50 for IgE in a 3 mg/mL *E. coli* DH5a lysate solution in protein arraying buffer and incubated at room temperature for 30 min. Chips, FAST® Slide Holders and FAST® Slide Incubation Chambers were assembled and nitrocellulose pads were hydrated using 250 µL blocking buffer for 30 min at room temperature with rocking. Blocking buffer was removed, pre-incubated serum samples were added and chips were incubated overnight at 4° C. with agitation. The following day, chips were washed three times with 1×TBS-0.05% TWEEN® 20, followed by incubation with biotin-conjugated anti-human secondary antibodies against IgG1, IgG3, IgG4 or IgE (Sigma Aldrich) diluted (1:1,000 for IgG, 1:500 for IgE) in blocking buffer for 1 hr at room temperature with agitation for one hour. Chips were washed three times with 1×TBS-0.05% TWEEN® 20, followed by incubation with streptavidin-conjugated SURELIGHT™ P-3 (Columbia Biosciences) at room temperature protected from light with agitation. Chips were washed three times with 1×TBS-0.05% TWEEN® 20, three times with 1×TBS, and once with water. Chips were air dried by centrifugation at 500×g for 10 min, stored in a light proof desiccator for at least 2 hr and scanned on a GENEPIX® 4300 with Autoloader using the 635 nm laser. Resulting 16-bit TIFF images were quantified using Innopsys Mapix Software and a GAL file. M635-B values were exported for each slide as GPR files.

Data Analysis. Software developed in R (Antigen Discovery Inc) was used to process the individual GPR files in batch to create a single matrix of the raw data and to perform automated data quality checks. The raw data were normalized by dividing the IVTT protein spot intensity by the sample specific median of the IVTT control spots printed throughout the chip, then taking the base-2 logarithm of the ratio. The normalized data provides a relative measure of the specific antibody binding to the non-specific antibody binding to the IVTT controls. Normalized data was imported into JMP Genomics (SAS) and analyzed for antigen reactivity and significance (ANOVA) between the clinical groups and isotypes, and adjusted for multiple comparisons. Significant proteins were graphed in Prism 6.0 (GraphPad).

Figure 1B:
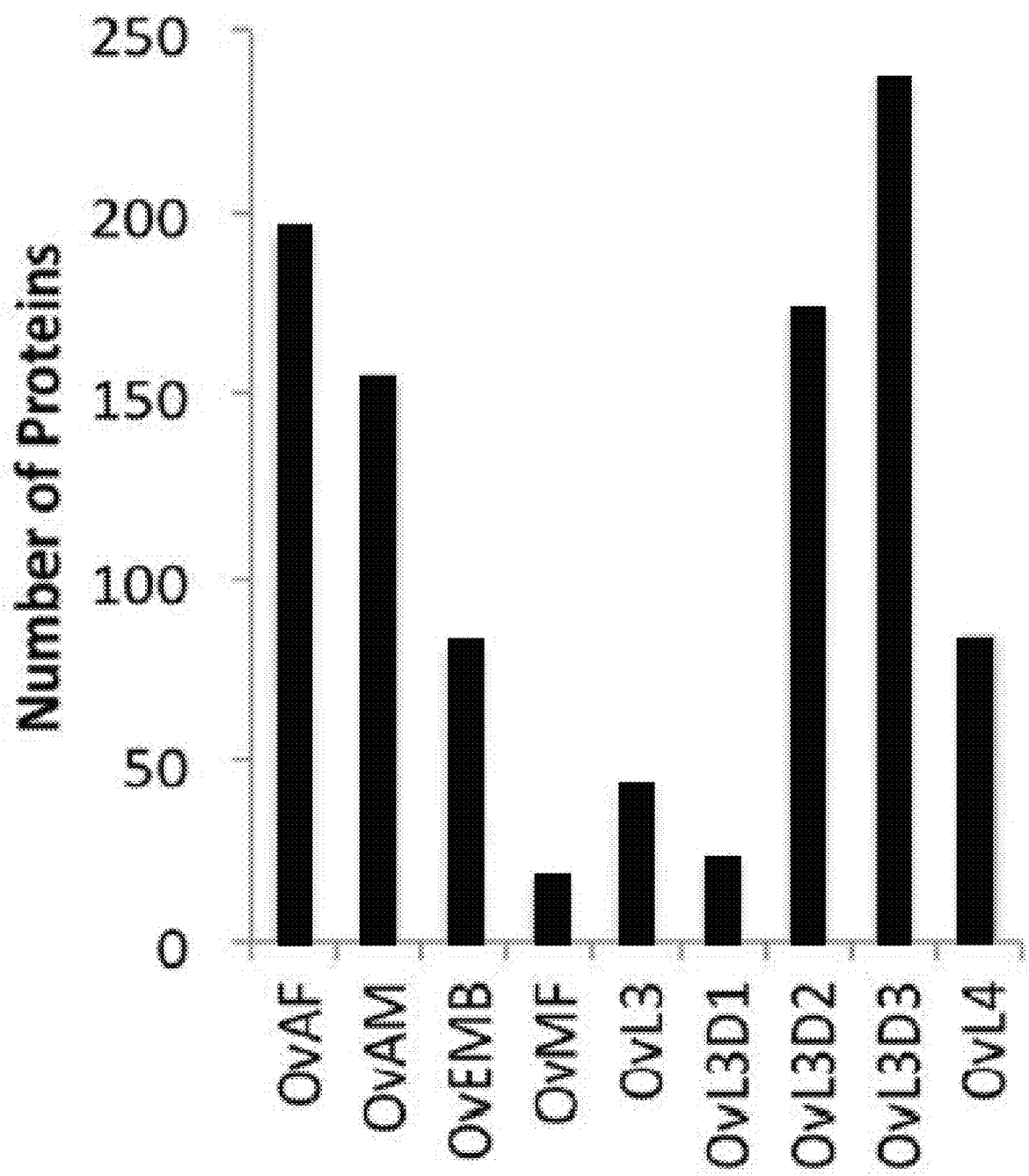

Transcriptional profiling by RNAseq resulted in the identification of transcripts corresponding to 99% of the predicted genes (FIG. 1A) across all the stages in the parasite lifecycle. Over 75% of the genes had 100% transcript coverage in all the stages except the adult female which may have been related to the age/condition of the worm(s) inside the nodule, degradation of RNA during the digestion of the nodules, or the fact that the majority of the adult female worm is comprised of uterine tissue and embryos. Several transcripts with less than 1 RPKM were subsequently identified and verified by mass spectrometry (in proteomic analyses) and thus have not been excluded. Shotgun proteomics identified proteins with a median coverage range of ~10-15% from each of the stages profiled. A total of 7,774 *O. volvulus* proteins were identified across all the stages (FIG. 1A) resulting in the validation of over 64% of all predicted proteins. Though there were no differences in the number of transcripts identified in each of the stages, maximal proteomic coverage was observed during the L3 to L4 development and in the adult male and female worms (FIG. 1A). This approach also resulted in the identification of 465 of the 785 putative *Wolbachia* proteins (FIG. 1B). *Wolbachia* is a genus of bacteria which infects some nematodes. *Wolbachia* species have been found to be endosymbionts of *O. volvulus* adults and microfilariae, and are thought to be the driving force behind most of *O. volvulus* morbidity. Overall r-values for correlations across all of the stages between the transcriptome's RPKMs and proteome abundance ranged from 0.25-0.39, values that are considered acceptable for global comparisons.

Multivariate analysis revealed stage specific transcript profiles that segregated the vector-derived stages (OvL2, OvL3), the early human developmental stages performed in vitro (L3 to L4 molting: L3D1, L3D3), the adult male (OvAM), the adult female (OvAF) and the microfilarial stages (SknMF—mf obtained from skin, NodMF—mf obtained from nodules). Infected nodules often contain more male worms than female worms which has been attributed to adult male migration between nodules. The proteomic analyses indicate a probable bias towards a male-like expression profile as the worms develop from L3 to L4 and to young adults. Hence it was hypothesized that it is also likely that proportionately more male worms develop from a single infection. Indeed, structural gender differentiation can be observed in in vitro developing L4 larvae. Notable among transcriptional and proteomic profiles was the observation that, compared to all other stages, the adult males have higher transcript abundance levels with many differentially expressed genes.

Example 2. Stage-Specific Functional Enrichment

Functionally, the total putative proteome was classified into functional categories. Forty-four percent of *O. volvulus* genes have no yet known function. The distinctive biology of *O. volvulus* is likely to be underpinned by genes with potentially novel functions and with relatively few homologues in other helminth parasites. Approximately 9% (1173) of the predicted genes in the *O. volvulus* genome encode unique genes with less than 30% homology with other nematodes. 92% of these 'unique' genes are hypothetical or genes of unknown function of which 7% are potentially secreted. Clustering of these unique and divergent genes based on transcript and protein abundances indicates distinct subsets that are enriched in specific stages, and that these clusters have signatures of being able to be secreted ("secreted-divergent"). Although largely uncharacterized, the stage specificity of their expression is an indication of their developmental regulation and may allow for functional assignments in the future.

Gene Set Enrichment Analysis (GSEA) demonstrated that the female stages were associated with pathways linked to detoxification and the extracellular matrix. This enriched subset of extracellular matrix related genes was primarily comprised of collagens and chitin. Although the microfilariae are an integral part of the fertile adult female, genes corresponding to NADH dehydrogenase activity (GO: 0008137) and cytochrome-c oxidase activity (GO:0004129) were highly represented in adult females. In contrast, the microfilarial stages showed significant enrichment for processes associated with protein synthesis (ribosomal proteins) and protein modification with cyclophilins and chaperones (heat shock proteins) being the major contributors. These are likely the machinery required for cellular morphogenesis that occurs after being ingested by the blackfly vector.

Example 3. Secretome and Host-Parasite Interactions

The *O. volvulus* genome encodes ~20% of genes predicted to be secreted by classical secretion and about ~42% through non-classical secretion. All filarial helminths are known to release excretory/secretory (E/S) products that are critical components in the helminth arsenal of proteins that perform diverse functions that include: 1) modulating the host immune response; 2) host tissue remodeling; 3) alteration in host tissue nutritional status; or 4) enhancement of larval tissue migration. The *O. volvulus* genome encodes many of these immunologically relevant genes. Among the examples of the stage-specific enrichment of these immune-related gene products are the L3-enriched or mf-enriched cystatins and serpins that have been shown to interfere with antigen processing and presentation to T cells; the OvAM-enriched expression of indoleamine 2,3 dioxygenase (IDO); and the developmentally regulated L3/L4-enriched homolog of suppressor of cytokine signaling 7 (SOCS7; OVOC678). Proteases (serine, aspartic, cysteine and metallo-) are integral to host invasion, developmental molts and migration in a number of nematodes. Serine protease inhibitors also play an important role in controlling the molting process and immune evasion. The analysis of the Ov genome revealed the presence of 18 serine protease inhibitors, nine of which are highly expressed during the L3 to L4 molt. Four of these are SPI-like, probably having resulted from a duplication event of Ov-SPI-1 and Ov-SPI-2; their marked expression during the L3 to L4 molt is consistent with not only their role in early larval development but also in their putative role in immune evasion during their early adaptation to their human host. Interestingly, two of the serpins are also highly expressed in adult males indicating a potential role in spermatogenesis, while one is highly expressed in both nodular and skin mf.

Example 4. Immunomics

Figure 2A:
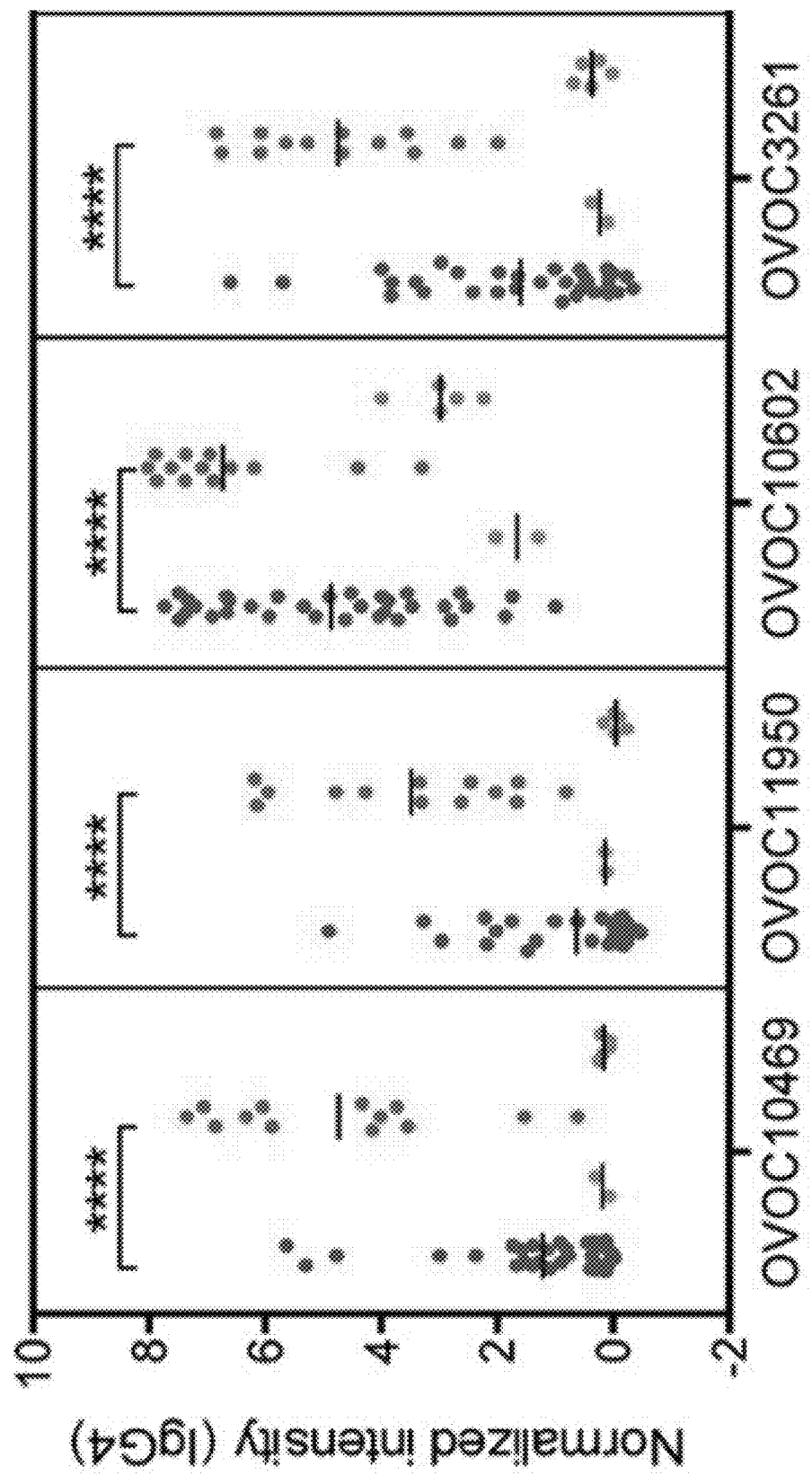
FIG. 2A-B depicts immunoreactivity of disclosed *O. volvulus* proteins.
Figure 2A:
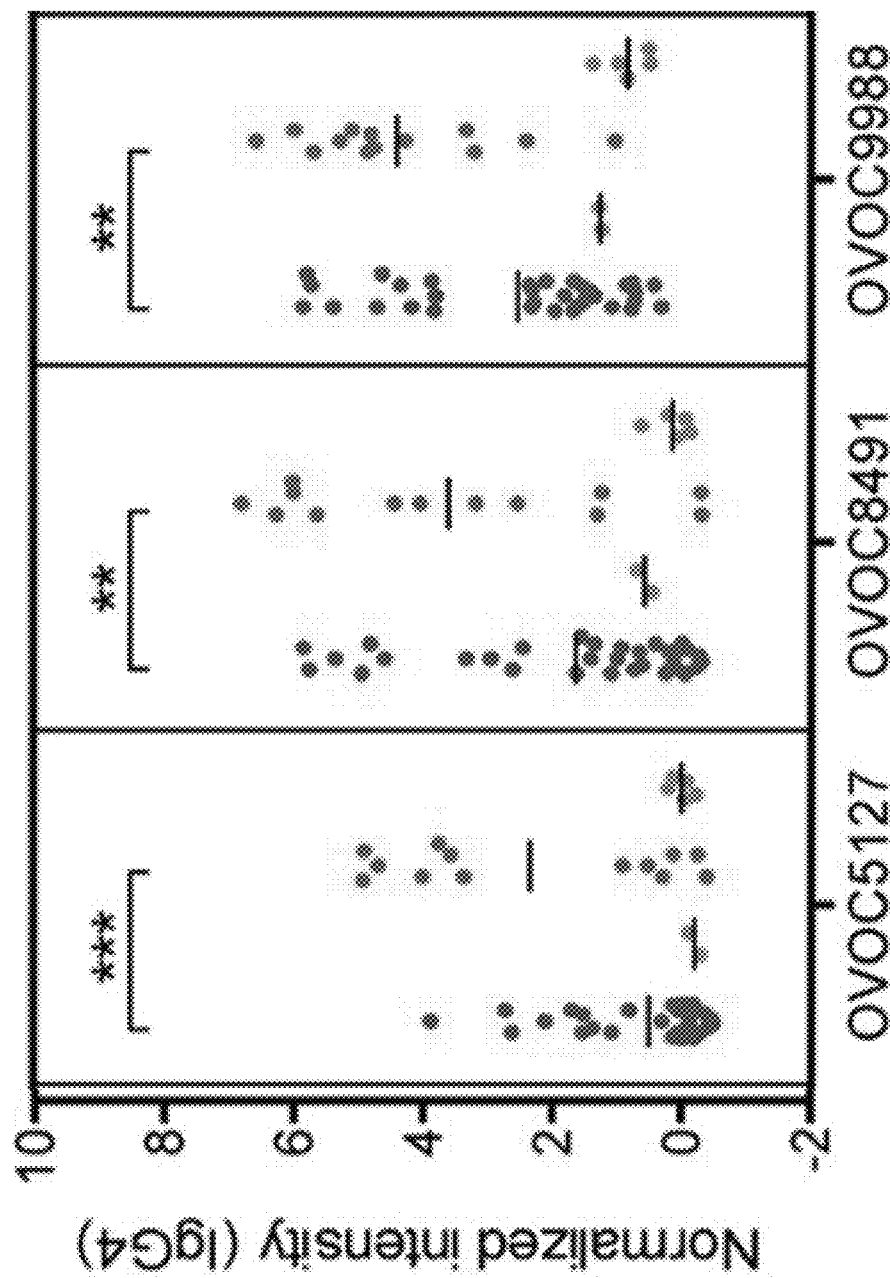
Figure 2B:
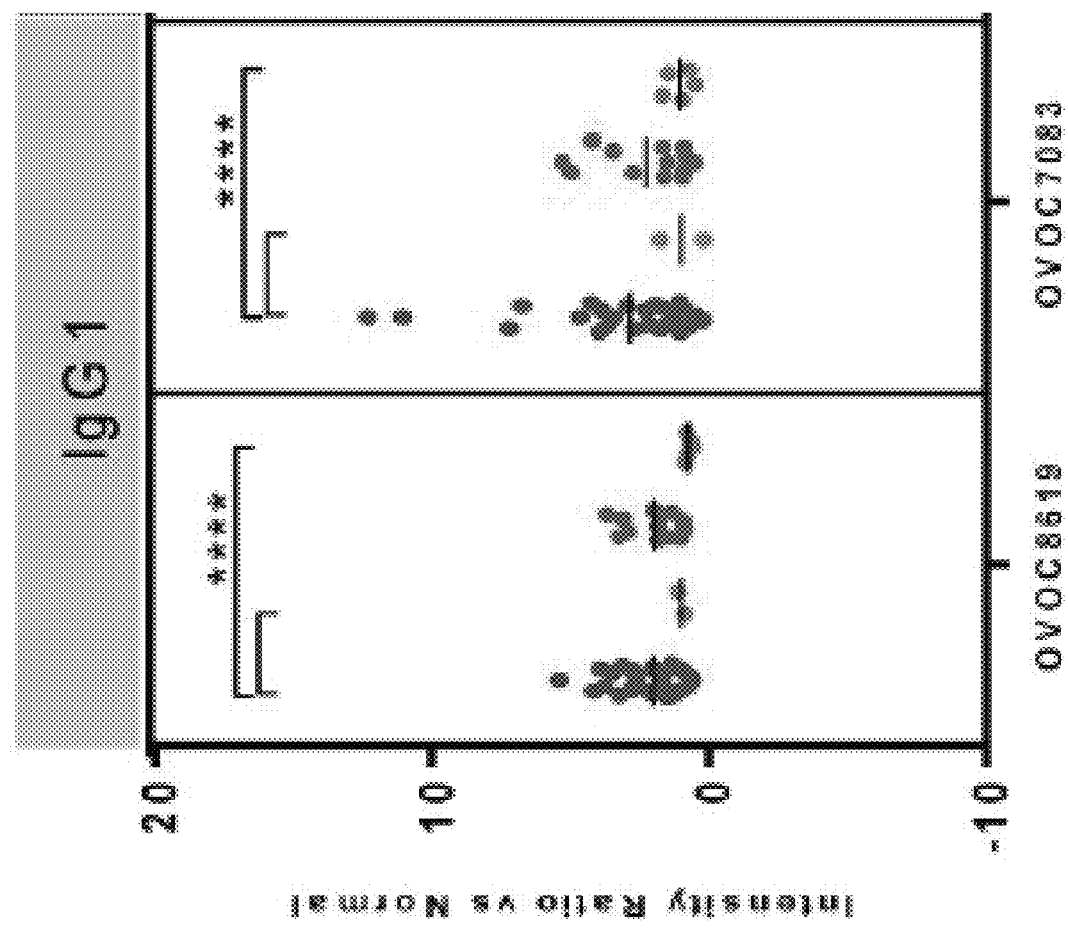
Figure 2B:
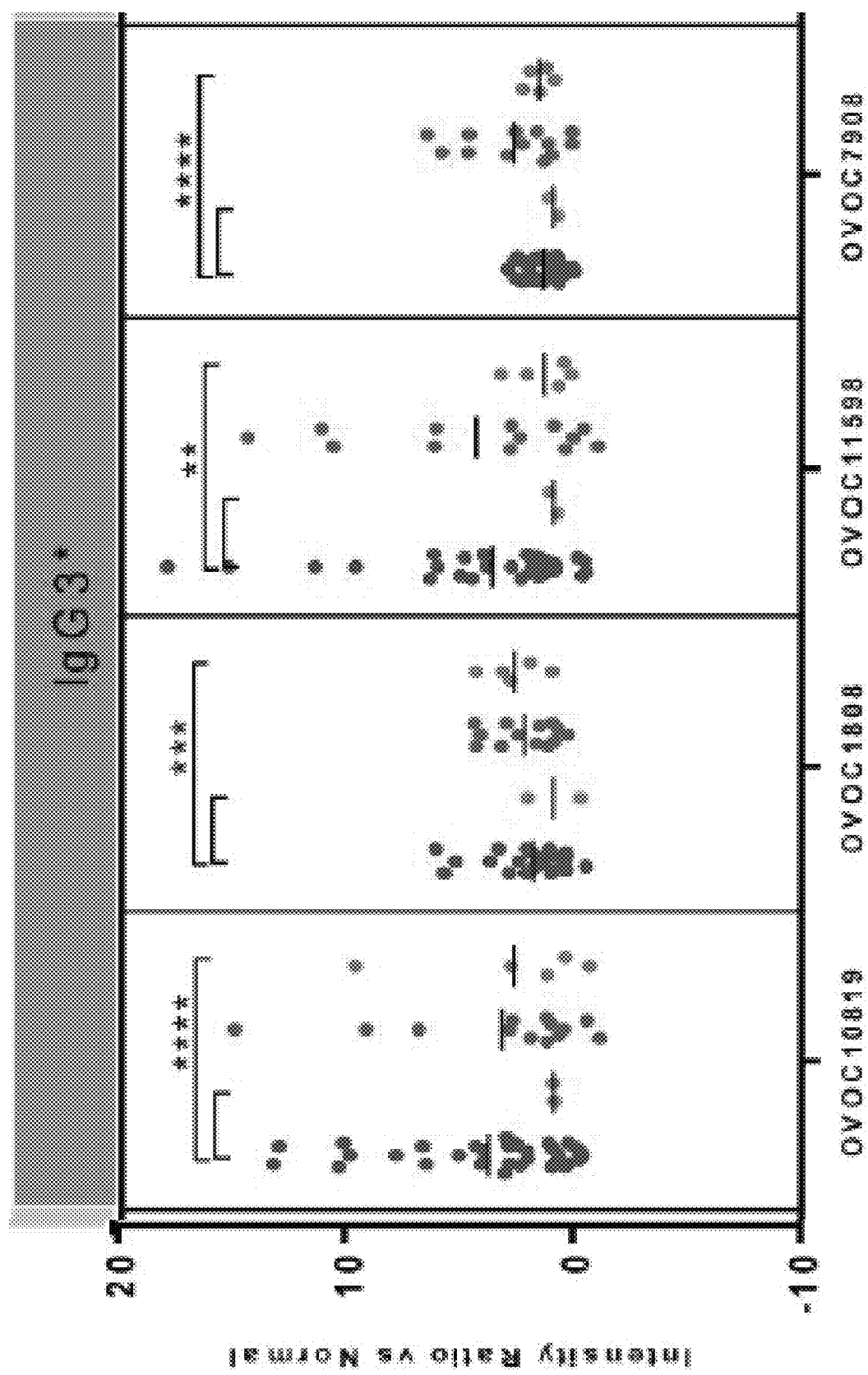
Figure 2B:
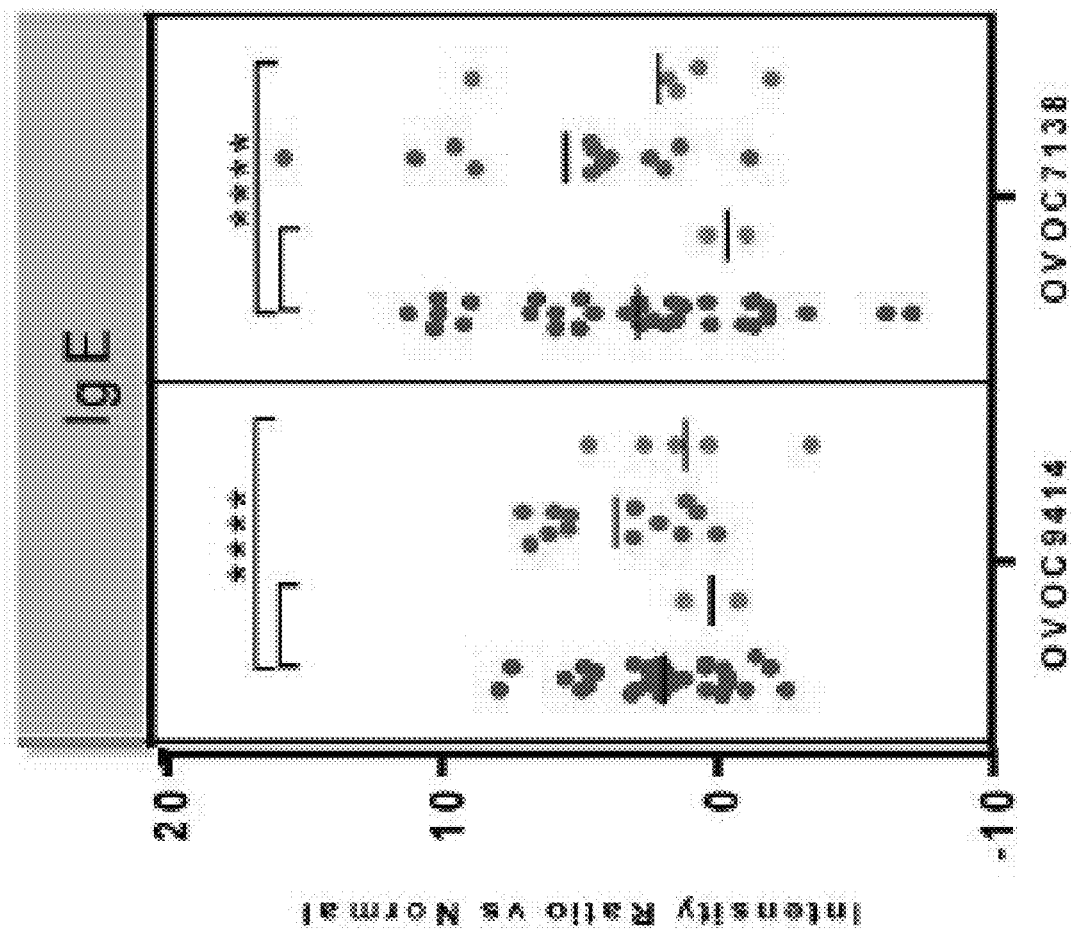

Using an immunomics approach, host antibody responses to candidate parasite antigens were profiled. Selected (397) proteins (based on their elevated expression in infective stage larvae and during molting and/or in microfilariae and/or adult stages) were printed as protein microarrays, quality checked, and assessed for isotype-specific responses (IgG1, IgG3, IgG4, IgE) with 52 individual sera comprising *O. volvulus*-infected, putatively immune, and control individuals from Ecuador, Guatemala, and Cameroon. After normalization, clusters specific for IgG4, IgG3 and/or IgG1, and with or without IgE reactivity were identified. Heretofore unrecognized biomarkers of active infection were identified (e.g. OVOC10469, OVOC10602, OVOC11950, OVOC3261, OVOC5127, OVOC8491, OVOC9988) as seen in FIG. 2A and Table 3. Further analyses led to the identification of potential novel vaccine candidates (e.g. OVOC10819, OVOC5395, OVOC11598, OVOC12235, OVOC8619, OVOC7083) (FIG. 2B and Table 4), based on IgG1 and/or IgG3 reactivity (with little to no IgE reactivity).

TABLE 3

*O. volvulus* biomarker sequences

| SEQ ID NO. | Protein Description | Sequence |
|---|---|---|
| 1 | OVOC10469 Secreted protein | NIAFAPNPKDSNNELFADAESALGSEYAQFVEQSKQHKPVYFSDNQNTLET IKLESIPNPETETAYPMFICGFLGCMKKMNSVEEYLEHFKMHEKQGY |
| 2 | OVOC11950 Secreted protein | YPTEKETVEPIDTMVKDDIDLVKAEVAEAEEADVEKEVAELTEEEAAEIAEVL DEMEEEFFAFLLFDFILDLFRETLEKNSESQEASIDEVMPEIQGVSAEEA |
| 3 | OVOC10602 Conserved secreted protein | FRTQSIGIRGRLMCGSKPASNERIKLWEEDSDDLLDQGYTDENGEFLLKGD TVELTPIDPVFKVYHDCDDGIKPGKRKVKFKIPKSYITEGKTPKKIFDLGTLN LETIFNDEERELIVT |
| 4 | OVOC3261 Secreted protein | SYCEDWDPEDFPSFVLKLSQNATEEFCELYEMEMEVPINKFYDMLRKWAE KYSVQAETNRFIAEEMNYDKMQSKVLMERLQASNGTTEVKGVLEKALKLQ ESMHLSPDYIQNVIDTMMENLPIDKQNEATLLWNSLYPDDIYNECGPRF |
| 5 | OVOC5127 DNA binding protein | APPNRDTADDLQNADMQRQWEQEQRQREEVQKEEIAKYVKYMRYLETVL NILQATPQWKEAMQSMTQEEMRGGKIAEMVDKLEPHIIEQLAKAKILELQRL EQEIKDQLNADGGATHNIKVSEILTVCLKEGFKKPSNLGIPEHLDFNNWETF |

TABLE 3-continued

O. volvulus biomarker sequences

| SEQ ID NO. | Protein Description | Sequence |
|---|---|---|
| | | SQEDLRKLIVKIVTDMDELEEQRKQDFKQYEMKKKAEEDHKMQAKMIQTE REEYIRQMEEQRRHNKHEPLKHPGSRNQLRKVWEDTDKLDKDAYDPTT LFGLHDRNNDGYWSYDELNTIFLPEIEKLNNFSDVERLEELYRMRDHVMKQ MDTDGDHRISRAEFLADREAQEEKPDQGWEDIGDKDQYTKEELEIFEKEY AKQQGWGEYAYSTPAPTPDPSRMIQPDQAPMQRLDAPSDQVGDMFAQQ SHQIPVKHVEPIQSVQQQQMDEVNS |
| 6 | OVOC8491 Fatty acid retinoid binding protein 2 | FPTEANPAVGTDNAHEDNLTTEEKMQLKKFAKTNAANFSLTDPEFIDGLKN EAAGLFSKLTGLRDIINAKLDTMQPESRLFIEKLLRRFLAAFSHDGLMNILES LKGFGKEVIDMFDGLSRPIQNDILNAFPLVGSYITSDIARLMLRKLAELDLLS RKSTLTPTVDQFNDDSGKHFPRPQVIEPEEPENSDPEDAQSTDYGKKKVV TTTTFPIITGEEDEILVKKIVENK |
| 7 | OVOC06759 Conserved secreted protein | IPLPEELDYDGEIPNCRDGEKPLLAADIGVYTCDKNCPKGFRCEYRTMDST SKKGICCPNLKELAKIYSEDEEVDKSIKKSNI |
| 8 | OVOC451 Filarial antigen Av33 | MISCFALPFPHVCYMAYCTQVIASIMKGWNQNFRFSTVIYLFRNIFSSSVISC VNMILSSTFYALLFVSAVVIVEAMPASESTYSVIIIRINDTTCKIEDGVVSVNG QVIGNLTEEQKEELEAYNVQTQGWFQQLHQKIEELFKTFFGSIKSMWKHSP ISGSESSPQSSTPDNIITDKLDDQDRRLKDQGDSENSSLFGLKLPSFCKVN |
| 9 | OVOC12329 Conserved secreted protein | FRSLKIGRKQSTAVKGVLTCNGKPAVNVKVKLYNDSQGRYVENSMDEGKT DSEGRFLLQGHETSITSIDPILKLYHNCDVENAQCLKRFSILIPNDFVSEGLE PKKTFDMGTLNLGGKFFDEGRECAS |
| 10 | OVOC3337 Glycine-rich cell wall structural protein-like | QIIGSFNGNYAGDGSLNNNANSFGERTTTTRSTSRPSLPPRPGYPSRPGY PFKPGFPPRGPPIPYPHGKPSGPRYPCYGGYGGYHPGYGPFGGNGYLG YTVCSGRGEFGGYGPGLGGGTGLGGLGPGEFGGYGPGLGGGTGLGGLG PGGFGGIGPGLGGGGLGGPGRGGFAGYGPGLGGGRGLGGPGPGGFD GYGPGLGGRPYPGGYGRFYGPGPYPGDRLDPRGLSESGRPRTRLASYN RNDRGTQFSYIRDR |
| 11 | OVOC10264 Beta-galactoside-binding lectin | MTNEYETNYPVPYRSKLTESFEPGQTLLVKGKTAEDSVRFTINLHNTSADF SGNDVPLHISVRFDEGKIVFNTFSKGEWGKEERKSNPYKKGDDIDIRIRAHD SKYTIYVDQKEVKEYEHRVPLSSVTHFSIDGDVLVTYIHWGGKYYPVPYES GLSGEGLVPGKSLLIFATPEKKGKRFHINLLKKNGDIALHFNPRFDEKAIVRN SLIAGEWGNEEREGKMILEKGIGFDLEIKNEEYAFQIFINGERYATYAHRLDP REINGLQIGGDLEVSGIQMR |
| 12 | OVOC4230 Conserved secreted protein | DLLSEAGDFFTKHFTDIKSLFAKDEKQLQQSVDRVKDLLATIQDKMSMLQP LANDMQKTTLGKIGDLISQVNSFRETMSNPKMDFTNKENKWEELLKKIFVT EGLNKVIPLLQKLKNSAPTTFATYLFTCIVPVLINTLRE |
| 13 | OVOC10384 | MARINRLNFLLCIVHANITSAPNPKDSNDELFADAESALGSEYAQFVEQSKQ HKPVYFSDNQNTLETIKLESIPNPETETAYPMFICGFLGCMKKMNSVEEYLE HFKMHEKQGY |
| 14 | OV008422 secreted protein | FSWKFGERLDEPVLMLRDLRAKEISPPSYMKRFESDTNEQLLRYILHPKML RRHDLSNALFYQPLWKMR |
| 15 | OVOC6395 Protein LOAG_00657 | MEGSPIKETRGLEATPVFEMVRSATLTFLLAVSTVLVVSRPNVLLPPKLPW DSDWRQKPPPFPPEPPPEFKGILPPEIFAKLTAIHQDQSLTIPQKIVKIEEIMN SLPEDVLQRLPLPPVFRLLPQNVQEMIKTVRTTKNLTMEEKWLQMIILIESLP KQQHRLLQQMLPKFSLGPLPDFQDIIPKEDWDKLTAVYQDTNLDNIEKLRR VDEIIDALPDSIRQKIPLSPPFQKLPDHIQQQLQIIHTERGLTTEQRFRKMKAII ESLPWDMKKLMFQP |
| 51 | OVOC10469_Pep2 | EQSKQHKPVYFSDNQNTLETIKLESIPNPETETA |
| 52 | OVOC3261_Pep1 | CPSLSSYCEDWDPEDFPSFV |
| 53 | OVOC3261_Pep3 | LPIDKQNEATLLWNSLYPDDIYNECGPRF |
| 54 | OVOC10469_Pep1 | AFAPNPKDSNNELFADAESALGSEY |
| 55 | OVOC10469_Pep3 | GCMKKMNSVEEYLEHFKMHEKQGY |
| 56 | OVOC3261_Pep2 | INKFYDMLRKWAEKYSVQAETNRFIAEEMNYDKMQS |

TABLE 3-continued

*O. volvulus* biomarker sequences

| SEQ ID NO. | Protein Description | Sequence |
|---|---|---|
| 57 | OVOC5127_Pep1 | APPNRDTADDLQNADMQRQWEQEQRQREEVQKEEI |
| 58 | OVOC5127_Pep2 | TDMDELEEQRKQDFKQYEMKKKAEEDHKMQAIQTEREEYIRQMEEQRRR HNKHEPLKHPGSRNQLR |
| 59 | OVOC5127_Pep4 | DREAQEEKPDQGWEDIGDKDQYTKEELE |
| 60 | OVOC5127_Pep5 | TPAPTPDPSRMIQPDQAPMQRLDAPSDQVG |
| 61 | OVOC5127_PepX | VSEILTVCLKEGFKKPSNLGI |

TABLE 4

Immunogenic composition *O. volvulus* protein sequences

| SEQ ID NO. | Protein Description | Sequence |
|---|---|---|
| 16 | OVOC8619 Adhesion-regulating molecule | LIKVFPEISANMSVMFANSRSNQANNGYLVEFKAGRSNLQAGSTVDRRKV VADKTKGLVFIKQSSDQLMHFCWKNRETGAVVDDLIIFPGDTEFLRVRECT DGRVYMLKFKSTDEKRLFWMQDGKTDKDDENCKKVNETLNNPPAPRAAA RGGADRADVSSFGTLAALGSAGAESELGALGNLDQSQLMQLLSLMNHTN STSASEATNLLPQLPLVADTSHPMTSEDSGTTSTHGATPSNTPANGIVADS SSNNAMQLSQLKEIIASITPPDGSGRKPSIDFTDVLCCADKINDVLRKYAEQL IPHLPSQEPIYNNQEELQQTLRTPQFRQAADIFGHALQTGQLAPVLRQFGID GNTATAAGNGDMVAWAAQFTTAENGKEITAKTETSPSQPGMESDVEDEE TNEKAIRETEKNRTDDHMDLD |
| 17 | OVOC7083 Secreted protein | MNYKAPIELQQLLSITKMLSLSVLLLFTSMAIMARPPNSDEIKELRQQQLNES KDDYDTLPDVNHIPESFKESLKKQKMLYLDMLRQHNL |
| 18 | OVOC4111 Mediator of RNA polymerase II transcription subunit 15 | LSVPAGLRPAKKVGDPKEQIVPGKQQQLQQQQQQQLLQQQQQQQQQQQQ QQQQQQQQQQQQQQQQEQQEELQQLQESEETGEEHRQQQQQQH DEALTLSPTPKVPPNLSIRSRMMAALSASVGESNKEKNSSNDETDNSSKST NSPSKPPIIFPKANKKTVVGKIAPSGISKGSARVIVAPPSKLGTNNFGLNTVL QTNLVDSRGRIMKNVNSPVIKVPSSAEMRNARTRHTARQVESDADKVVPIK FGSTSRRR |
| 19 | OVOC1808 | NNSNLDISMREKNAVNAIEKQDLPRSHRFKRQYSCGQCGGGGGPPVVVS PCQQCKGGGAGVSAIGGAGGISAIGGGVSAIGGGFGGGGGDTVAVVCCG ATGLKGMFRNWWLHIPLLLLPMSMSWIKALFL |
| 20 | OVOC11598 Secreted protein | YYVPDNYWPLRIIGYHHIPVMINMWYLFQTEISNIGVDAVLVQSPLYRTLTP DVVHDIISINVEPNHTVVVEQSNPMLQASSVEQAPAAAPLSITLIAPGITISRT HKVDTYKSTMEMYDADKLHSNEIFKRRVRKMVLPPSRGEEVRKPPSSTDG YESENVESYGQKGVEQAPPEIEQYVKKKK |
| 21 | OVOC3901 Immuno-globulin I-set domain containing protein | MKYCLSSIIAATIATTTTTATAIIATTITAATISVAPFHASSPSSSLSSSSFSSFF LVLPLITTILLIVPEQAHSTATVTEHRSPPDLSIPSQTEFRVPVGTKQFRLICP VKEKNDDLLMIQWKKNDEPIGFDFNNRPFKLARSDRELKIRNPQLSDGGIYQ CQVVNGFGHRELNFTVTFYDPAMENDQNTDSTLTLTTKASPPIWKNETEIR NWMINPVRITIGGALLLKCPAKGNPLPHITWLRDGKVLEREITYHYSSAILYL SDVQPSEGGKYICKLENEHGSIEASFHVYVENFFEGLDGESWSIDQTNAQL YPVIDEPFNNTVRVGRTAQFQCKVKNQQQPLIKWLKRVEDPNAIRQTNAN ATLIHANNMHLLLLEKPETSAELSDGISLNRLIIPNVRYEHSGTYLCVVTNAR GDIAYRSAYLNVIARSDHGELSNLYFYGGLLVLIVVFTLITYAVHFLRKNQAA KSTESAPGITNIRYSFSLRPPPPNLPPPKAPALPSERQQLMPNNQPCDRYT VNSAAATYYPQFATPDKKLQKIITESGTRPTPIRRTNGGDTKYRLKDDYISS PKWVHAKGDNIEVEMDQNLLKNRSTHCHNPVSIAYGRIDNIDRQQQKSFLT IGNLQKR |
| 22 | OVOC10819 Secreted protein | KEIIWDCYGDYEECVAESSKMDHVDVNNVESRNIIEFCSDHTQNILPCLATK LGLIKSMSVSMFSLLLTICEAETRNNRPAATEVQQILKHLARLYAYFCAYSN VIDLRYNKECFRYLKKRCILNKPDDSCIFHHCGEKNLNLSESSPFIQQHKTTI INQLNQSATFKNYHHRITTIFTVIITFISMIQ |
| 23 | OVOC5395 Protein Bm1_06245 | MYNQENHDKRRNDDRFILSLPFGTNVENKSYFKPIKLSNPYSDKYLEVNKK SSDDSDQNLNQALSVPQSNYDQSSESLSIDDSDLIDDSTSAAQLSTSSPISV TSASTSSFYPTLNIGNGMEISAKYAKLEQSQGIKSDQTSRVSDRYKKYTA VKRRLSELYGIIEEKDEQLRVVRNELNGKDLEIGKLCDKIRALEYNCGRLQS MIESAGDESDQNVKLHEIINERDGLLIRNASLSRQIEFEKREWSIERERLS |

TABLE 4-continued

Immunogenic composition O. volvulus protein sequences

| SEQ ID NO. | Protein Description | Sequence |
|---|---|---|
| | | MDLDDVTRELELQKMILNGESISEIVQRWQTKVFELEGMITDRDRAIRAQQ VQISKLKESIAETDRISCADSSESQTKFDFPSFTYIKRLLLQYLTRLADLHFSS DEERMQLVRNMSSILHLSDEEQRQVWANLKSKIQIS |
| 24 | OVOC12235 Conserved secreted protein | QCPTGSVSLLSGYRCTSSIQCQTIIPGSYCYYGVCCTGGSDVLSKTVSYGG YCTMTVQCSTTGATCISNICQCDINSHYNGHSCVSISNFCPSNQVFIKGECY RKVTYGFLCNYTQQCGYIGAFCIGNICSCQLDYTFDGSKCIPRSRICPANQI AIGGQCYPSARFGERCLYSEQCIDRWYRSLSCVNGFCNIRNDDDISKPKC RNPRAEVEYVNGTAKNCLYWPCTVGYFCEYAGGMNGGRYICCGTNANKI YGKVQLYPGTGTPLQCTEIGRCPFPDTPNCVMSYRYGYKVCCSTLNC |
| 25 | OVOC7908 Lateral signaling target protein 2 homolog | QETSEQPGLTVEIIAEQQDATTADQEVTTTVDTHHQHQHQTDKVVKSRQIT GDEQTTTTTTAINLNETITNSTTDSNSTIITTTLDLQESTTTGTTDNHHHHHH HHHHHE |
| 26 | OVOC7430 RhoA GTPase effector DIA/ Diaphanous | MKQTTAWGNALCVLCNCHQPQIICPPPPPAVCPRVVCPPPRPPVCPPIYC PPPVVCPPPPVCPPVPFCHSQICPPCGTHTVPVAVVGCCKGCACSVRFKR DSSSVNGLMLKKNLLCNNDQLMTIMEKKIGTNATEAAFAIKKEADSELKAKF SVFCAMNDLIYVAHAESFCQHKKGDIICFAYKS |
| 27 | OVOC8936 Microfilarial sheath protein | MDCKLILPFYILLANLEANAFHLSGYRSRSYLQGIQPYDIQPLDVQPQFIRVQ TLKSQDIQPYSIQSRSEDQPCEGCKITISCGSKNCKSKKLPYVVYKPIFKLLST RSTKKPVFTLPTQPPAQWDCPCPCHVPQRCRMCSACHESYI |
| 28 | OVOC5806 Conserved plasma membrane protein | NRIISRRLSLFIQQYCCNNISQIYRLNDCKYSKVKMEIDKKIFIIVSKTEWCNE AIKVVFGKSAEAIRNNSDAISWLASYNYTGSMDLRSKWPYDAYFDNVTRTA HGLARIDLLCHKKRPQLGPRIWKRSVQKIKQKKDRPFAVNTYGNNKGLFTIT VGVLLYAAFGTCFLIANLAYLFGIYIIYDASIIDEVS |
| 29 | OVOC4665 Conserved secreted protein | IGENPMDVNAIAGIIGGISNMMQNNVETIDVPSSQIMGRWYQVYKAAIAFDV YRTDIFCPVAYFKPNSVMGEDGFSIEEAYRVITKNGPVETYKRDLNKVGTG QYWMYTEEYFYPRQFNIISVGPNYTNTTDGSEEEKQYQYMVVTDGNRLSL SVYARHPMIFYQKYNEEVVKFLEHAGFGGKVFWNSPKPIYQGADCEWPSE KEVFARRVLKNQELAKNGGLDTATKSGSFGGSSQATDVRSSITEILQNPQL ALQKLVQGH |
| 30 | OVOC8227 HAD- superfamily hydrolase | MTIIKSMLKITHVIFDLDGLLIDTEVVFSKVNQCLLSKYDKKFTPHLRGLVTG MPKKAAVTYMLEHEKLSGKVDVDEYCKKYDEMAEEMLPKCSLMPGVMKL VRHLKTHRIPMAICTGATKKEFEIKTRHHKELLDLISLWVLSGDDPAIKRGKP APDPFLVTMDRFKQKPEKAENVLVFEDATNGVCAAIAAGMNVVMVPDLTY MKIPEGLENKINSVLKSLEDFKPESVGLPAYDASSNE |
| 31 | OVOC9988 Serine/ threonine protein kinase DDB_G0280133 | IPQRRQQQQQQQQQQRDEREIPPFLEGAPPSVIDEFYNLLKTDENKTDQ QTEADVEAFINRLGGSYKVRFTQFMEEVKKARADYERIHQQAVARFSPAA KDADARMSAIADSPHLTTRQKSQQIQAIMDSLSESVRREIINALSPQE |
| 32 | OVOC4230 Conserved secreted protein | DLLSEAGDFFTKHFTDIKSLFAKDEKQLQQSVDRVKDLLATIQDKMSMLQP LANDMQKTTLGKIGDLISQVNSFRETMSNPKMDFTNKENKWEELLKKIFVT EGLNKVIPLLQKLKNSAPTTFATYLFTCIVPVLINTLRE |
| 62 | OVOC7453 (CPI2M) | KNPSKMESKTGENQDRPVLLGGWEDRDPKDEEILELLPSILMKVNEQSKD EYHLMPIKLLKVSSQVVAGVKYKMDVQVARSQCKKSSNEKVDLTKCKKLE GHPEKVMTLEVWEKPWENFMRVEILGTKEV |

Natural immunity against *O. volvulus* can be acquired in a few individuals in affected populations and these individuals are known as putatively immune. Consequently, they exhibit protective immune response against L3 larvae, suggesting that E/S products released by molting larvae and/or surface proteins of L3 larvae are an important source of protective antigens. The identification of proteins that are highly expressed by the mf and that are specifically recognized by sera from protected individuals who never developed a patent infection opens up new possibilities for also developing a safe anti-transmission or therapeutic vaccine. The identification of Ov-unique proteins that are adult and/or mf stage-specific that are recognized by sera of Ov-infected individuals provided additional novel biomarkers needed for better mapping the prevalence of infection and for post-control surveillance.

It is anticipated that *O. volvulus* proteins, or orthologs thereof, will provide protection against infection with *D. immitis*. *D. immitis* orthologs of *O. volvulus* proteins are provided in Table 5.

TABLE 5

*D. immitis* orthologs of *O. volvulus* proteins

| SEQ ID NO. | Protein Description | Ortholog of | Sequence |
|---|---|---|---|
| 33 | nDi.2.2.2.t00004 Proteasomal ubiquitin receptor ADRM1 homolog | OVOC8619 | MRTASQLTFMLFLVLKKKFKNIDKLFSQISVNMSVMFANSRS SQANSGYLVEFKAGRSNLQAGSTVDKRKVVADKTKGLIFIKQ SSDQLMHFCWKNRETGTVVDDLIIFPGDTEFLRVKECTDGRV YMLKFKSTDEKRLFWMQDGKTDKDDENCCKKINETLNNPPAP RAAARGGADRAGASSFGTLAALGSAGADSELGALGNLDQN QLMQLLSLMNHTNSASASEAANLLPQLPLVADTPNPVASEES GTTSTQGATPSNTPANGIIAGSSSNNAVQLSQLKEIIASITPPD GSIRKPSVDFTDVLCCADKINDVLGKYAERLIPHLPNQEPIYN NQEELQQTLRTPQFRQAVDIFGHALQTGQLAPILRQFGIDSN TAIAAGNGDLIAWATQFTTSENEKEIAVKTETLPFHPGMESDV EDEETNEKAVRESDKNRTDDHMDLD |
| 34 | nDi.2.2.2.t03357 | OVOC7083 | MLPTLYINNAVIRPVLSETKKVKVQNISSPPLIFLLLSITKMLSLS VLLLFISMATMARPPNPDEIKELHEQQLNDSKDDYDMLPDVG HIPESFKESLKKQKMLYLDMLRQQSL |
| 35 | nDi.2.2.2.t05919 | OVOC4111 | MISSRLRITIPESIVIFGIFCFFIFFCFLSFFFFFTLWSHRDTINFQ TDFMTETIKFIVYAVVILRMMFFDIVCFYSFLMMTIVLINTSNGL SVPAGLRPAKKVGDPREQIVPGKEQQQQREQQQQQQQQLQ EEEQQQQQQHDEVSNLRPTPKVPPNLSIRSRMMAALSASPV EPNKEKNSSKVETDSFSKPPIIFSKGNKKTVPGKIAPSGSSKG NARVIVAPPADLGKNNYGLNTVLQTNLVDSHGRIMKNVNSVPI KVPSSAEMKNARTRHTARQVESDADKVVPIKFGSTSRRR |
| 36 | nDi.2.2.2.t07753 | OVOC1808 | MMRIKWIILLLLLLLPIITAEFSAPVGTNSSLTIFDKDKQVLLRSD RLKRQCGPCGVAPSPVIVCCGAAGLKEIFRSWWLHIPLLLLP MSTSWLKTMVC |
| 37 | nDi.2.2.2.t06812 | OVOC11598 | MFRLLIAIQILRFCQANYINDVYWKRSIIGYQHIPIILNICYLLQTE VSNKGVVDALFLHSPTYHRVEMSEETDNIESIADKSNITVANKP NLMIYPADFQVSSNERASASIPITITITSSGDTIIKSFKHKHQSNE IFKRRVAKMAIAPVNAPEVENLAPEVENPSPSTAGYESKTEEQ APSESGQYGKRRK |
| 38 | Fibroblast growth factor receptor-like 1 nD 2.2.2.t10368 | OVOC3901 | MYNLAKLLENEHGSIEASFHVYVENFFEGLDGESWSIDQTNA QLYPIIDEPFNNTVRVGRTAQFQCVKNQQQPLIKWLKRIDDP NAIRQANANATLIHANNMHLLLLEKPETSAELSDGISLNRLIIPN VRYEHSGTYLCVVTNAHGDIAYRSAYLHVIARSDHGMLSNIYF YGGILVLIVVFTLITYAVYFLRKNQAAKNSESAQDITNTRYSFSL RPPPPNLPPPKAPALPSERQQLMSDNQPCDRYAVNSAATTYY PQFATPDKKLQKIITESGGTRPTPIRRTNGGDTKYRLKDEYINS PKWVHTKGDNIEVEMDQNLLKNRSSHCYNPISGAYGRIDNID RQQQKSFLTIGNLQKR |
| 39 | nDi.2.2.2.t02919 | OVOC10819 | MLKLANTEIFFIAFLVYSKEIILNCYEDYKECVATSNKTNHVNMD NVNPQNLIEFCFDHTQNILPCLVTKLGLTKGISVSIFSLFLSTCE LEAQNNKSSSTTEMQQILRHLLRLYAYFCAYSNIIDLHRNRECF RYLMKRCVLNKPDESCMFYHCGKIHFNLSKSSRKILFTRQHDT TKIVNLGNKMNQLATFNNHQVRSAVVVTLIITFIDMIQ |
| 40 | nDi.2.2.2.t01093 | OVOC5395 | MYSQENQDDKRRNDERIALSVPYNNTNIMDRSYFKPIKLSYPY SDECLEVNKKSSDDSDQRLSQNSSTPQSNYDQSSERLSIDDS DLIDDSTSAAQLSTSSPISVTSASTSSFYPTLNIGNGMEMNAKY AKIEQSEGIRSDQSSTLRISDKYKKYTAIKRRLSELCGIIEEKDK QLRVVRNGLNEKDLEIGKLCDKIRALEYNCGRLQAVIESVGDE SDQNQIKLHEIINERDGLLVRNASLSRQIEFEKREWSIERERLS MDLDDVTRELELQKMILNGENISEIVQRWQTKVFELEGMIADR DRAIRAQQVRISKLKQSLAEADRISCDDSSESQTKLDSPSFICI KRLLLQYLTSSDEERIQLLRNVSTMLHLSDDEQHQVLTNLKSRI QIS |
| 41 | nDi.2.2.2.t11596 | OVOC12235 | XKCIRDQRAEVEYVNGSAKNCLYWPCTVGYFCEYTESRNGGH YICCGTNANNIYGKVKVYPGTNKPLHCSIMNTCPFLDTPNCVM SHRYGYKVCCSTMNC |
| 42 | nDi.2.2.2.t05701 | OVOC7908 | MLMKQSDSCVDYFYDQYKGQEYVKDDAFNTQNITDNFRKSS SDIAQLMNSQIELISQPEKVNEDSAKSSHYNDDLQKSIEDDTVE ATQRKKDEKLLEFLHSLIVSTIPKTIHLEGNSVNLLTLITTITPIAII TTKNTSGTANAITTRKYKKYKLNAFVNISSDTLTELPKFLPENF NSTNFANVEKTEKFSNSKQVATDSIFSLKESAYLETPVIRDFSS ANDSAKTDPLFTRNYVDKQIDMNTTKFNKNLKKSRLTTISTSNL TTVLSQLQTTTSISTTTSVTTTISTSITIPELTLVSQSHRHLHHYH HHHHQYENYDHESPIIVTALFDIGRGKWPRYTRTYEQYMNY LKHLLKLENCLVIYTDSRGAEFVRQTRNVHNTQIFEISMHDLPL |

TABLE 5-continued

*D. immitis orthologs of O. volvulus proteins*

| SEQ ID NO. | Protein Description | Ortholog of | Sequence |
|---|---|---|---|
| | | | YRYREEMKGIIQREQKDWQFSPKTRYHPEANSADYNIIVNSKP YFLYNATQNVRFRTSDRMFVWIDAGYGHGRKGIIPDHCHWRP RLQRDRMTIIQLTPKHDKVSRYSITDLYRVDWVVLSGGFIAGD SHTINRFYRFYQKLFMELLDSGRIDDDQTILTLMLKHYTTLFNPI SSNGDWYALFRLFPCHDRQ |
| 43 | nDi.2.2.2.t04336 | OVOC7430 | MKQATTWGSICEMCPCAAKPICPPPVICPPRICPPPVICPPQIC PPCPPRICPPPVICPPQICPPCPPQICPPCPKPQPPPPPPPPPV LPSLPPTSFKPMITCCRTCICYIRRKRDSLNDYDRIHDINPVCN NDQLMMIMKKKIRTNVTESTIAIKKAADSMLQAEFNVFCAINDL THVAHAEHFCQYKKDNSVFDSFLFRSTLKGLIEECREGVRWW PGSLGDLDFSHISLYRAHKYIGNEEMNRSTKTKISFTRINKKWR LGHTGKKYNKVRFSRNIAKKFIGVCNIIRLKKSVSRSVRPFENQ KSTSFNVFQLLVPKEKVEIVVDDTQAEEMNSETAQEVQLFNVR KSNADSKTDGEKDTADLDVILLTNEECSSSRQENLNKDEPEIVI LDDSAPSKSDLNTSDEIICLQDLKMVNEVPTFSVTPKQKTVKEL PRETRTYGTRRGRQSRAYCEDLRKFPSIRNPVSSSSSSIHAKN MPEFVDLLTQGTLLICKKWLRRWDIVQSGVIGGNPLRICSYNV LCQQTAYKTPELYIHLTKPGRAYELTWENRWRLLTREFSMIGA DIFCLQEVQYDHYDQFFRPYFEAAGFFGKYKKRTNNLLDGCAI FYKSHLQLLHYRYIEYFLNIDSVLNRDNVGQLIRLKDMRSGREF CVVNTHLLFNKRRGDVKLAQLAILLANIDQECGPESGQECPYIL CGDFNFHPYSPIYNFIMNGEICFTNLRRGDISGQGNAGGPFVS VNLLPEDVKIARNCRFNYLKNRTMLLPSLNCWSHPLCFNSVY QNMNGETRPMISTYHSIEAVNPDFIFYSVKSKRVQQSMLPHSV PAMNVSEREIRLIRRLSLPDMNELAGTLGPWPNSTTPSDHIPLI ADFVLQ |
| 44 | nDi.2.2.2.t10647 | OVOC8936 | MYCKLIISFYMLLSIANMTHLVGYRPQIYLQGIPQNIQSHDIQRL DMQQQSLKLPDTELYSIPSHDNQLQGLQLYDMQFQGKQSKG SEKLCSGCKISINCSGKKCVPMRTRKPIVTTPSPLSTQRPVLTR PRLLADCPCPCHVSRQCRICQPCQESFI |
| 45 | nDi.2.2.2.t03537 | OVOC5806 | MFVGMRLYLAIDVLLLLVLRIKSNRIILHRFSLFIQQHCCNNISQI HRLNDCKYSKVRMKIDKKILIIVSKTEWCNEAIKVVFGKSAEAR RNRSDAISWVTPYNFTGLMNLHSKWRYDAYFDNVIRTAHGLA RIDLLCPKRRSHSGRRILKRSIQENKQEKSRRSFTVNIYGSSKG IFTITVGVVIYAIFGVCFLITNMAYLSGIYTVHNTSVIPEDKKRKE TSKRKEIL |
| 46 | nDi.2.2.2.t01073 | OVOC4665 | MISVFLLLTVIVSYVETIGENPMDINALAGIIGGISNMMQNNVETI DVPSSQIMGQWYQVYKAAISFDAYKTDMFCPVAYFKPNSVMG EDGFSIEEAYRVITKNGPVETFKRDLNKVGTGQYWMYTEEYF YPRQFNIIGVGPNYTNATDGREKENLYEYMIVTDANRLSLSVY ARHPMIFYQKYNEEVVKFLEHAGFGGRVFWNSPRPIYQGTDC EWPSEKEVFARRVLKNQEAARNTGLETATKSGLFGSSLTTDA YNPIKEMLQNPQLALQKLVQGH |
| 47 | nDi.2.2.2.t00378 | OVOC8227 | MTVIKSMLNITHVIFDLDGLLINTEIVFSQVNQCLLSKYGKKFTS HLRGLVTGMPKKAAVAHILEHERLSEKIDVDEYCKKYDEMAEE MLPKCSLMPGVMKLVRHLKAHSIPMAICTGATKKEFELKTRCH KELLDLISLRVLSGDDPAVKRGKPAPDPFLVTMERFKQKPEKA ENVLVFEDATNGVYAAIAAEESKIVK |
| 48 | nDi.2.2.2.t01674 | OVOC9988 | MILEQLEVPPFLVGAPQSVIKQFYDLLKADETKTDAQTEADVE AFINRLGGTYKTRFDQFKQEIKQGKAAYERLHQQAVAKFSKEA READAKMSAIADSPSLITQQKTQQ1QAIMD |
| 49 | nDi.2.2.2.t06953 | OVOC4230 | MLKYGILLILITVGAYCDLLSEAGDFFSKHFTDFKSLFASDEKQL QQNMDRVKDLLATIQDKMTILKQLADNSQKSTLEKITDIISQVN DFRENVFNSNVDFNQKKTKWEEVVTKIFVTDGLNKVIPLLQKA KNSAPATFITYLLTCIVPLLINALRE |

Example 5. Immunoreactivity of *O. volvulus* Proteins

Figure 3A:
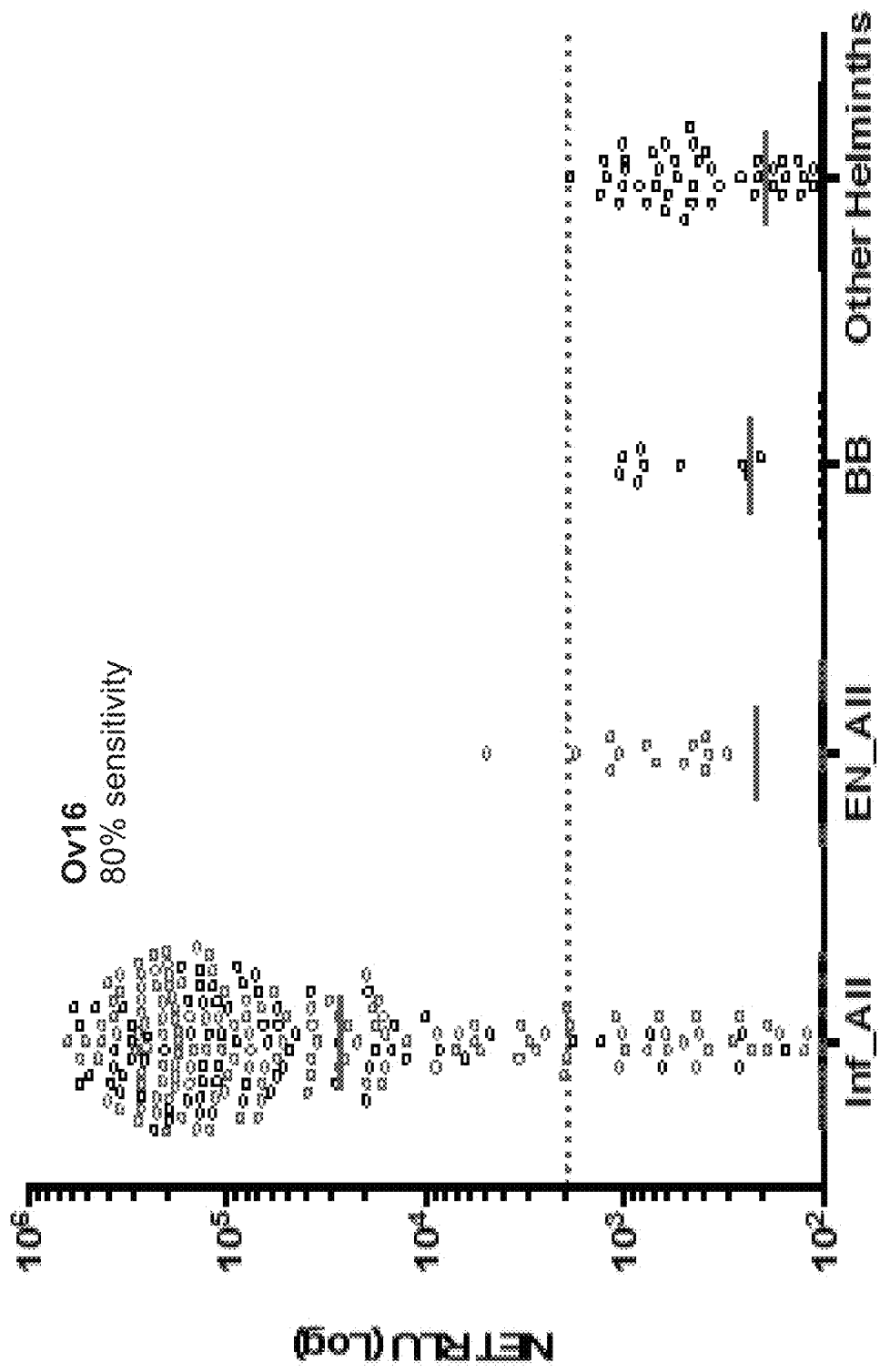
FIG. 3A-H depicts the sensitivity of the biomarkers for *O. volvulus* infection.
Figure 3B:
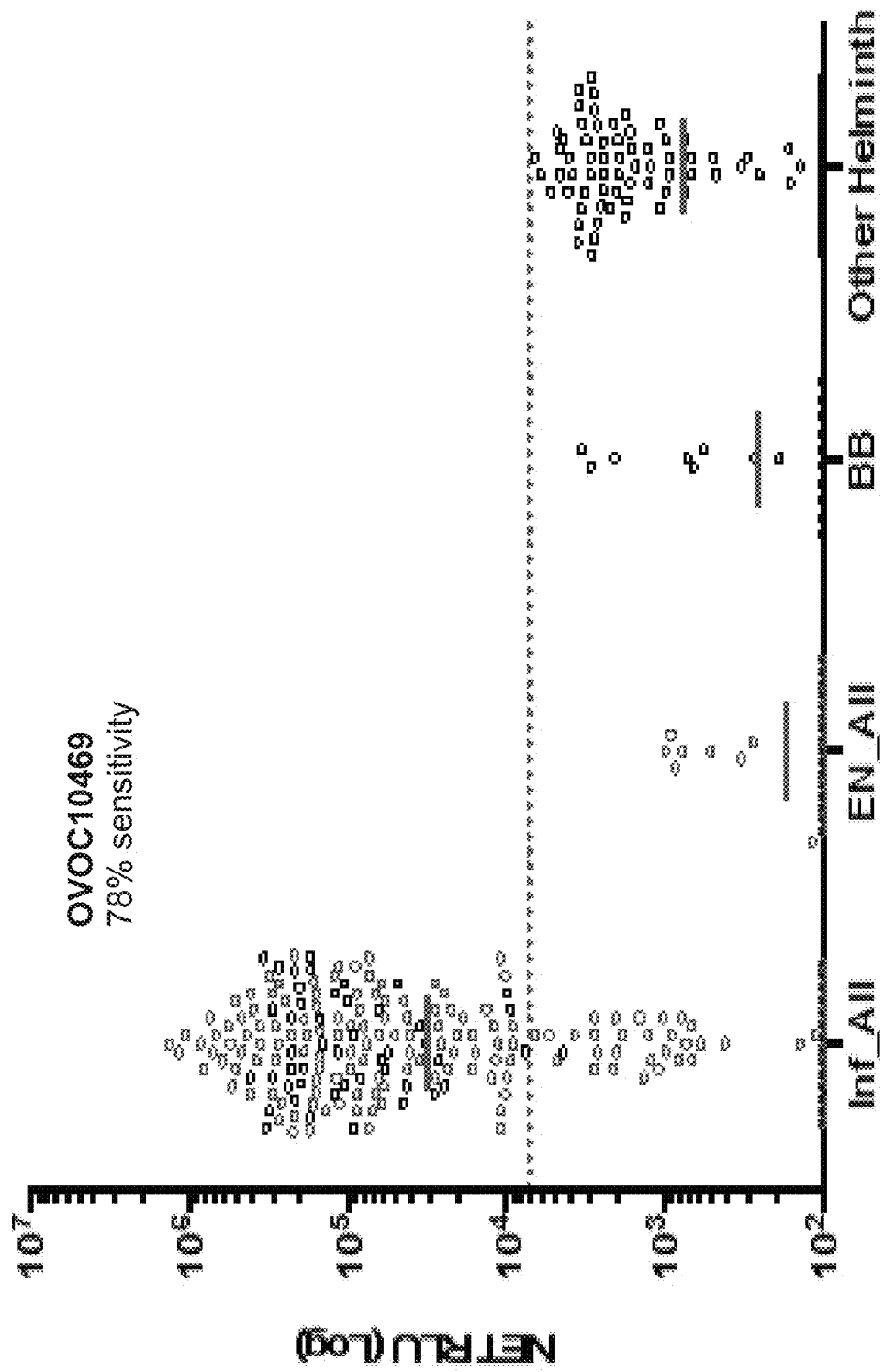
Figure 3C:
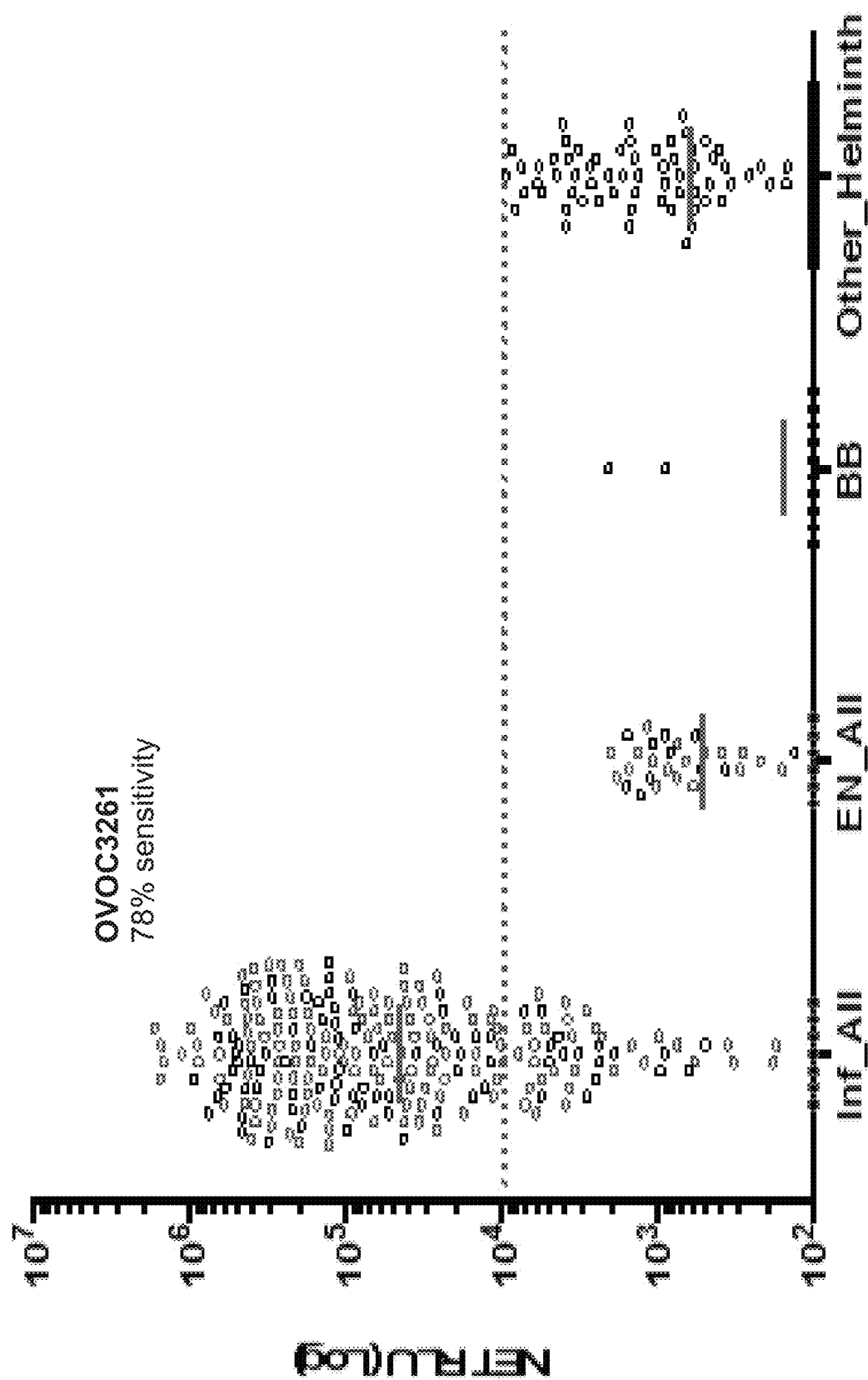
Figure 3D:
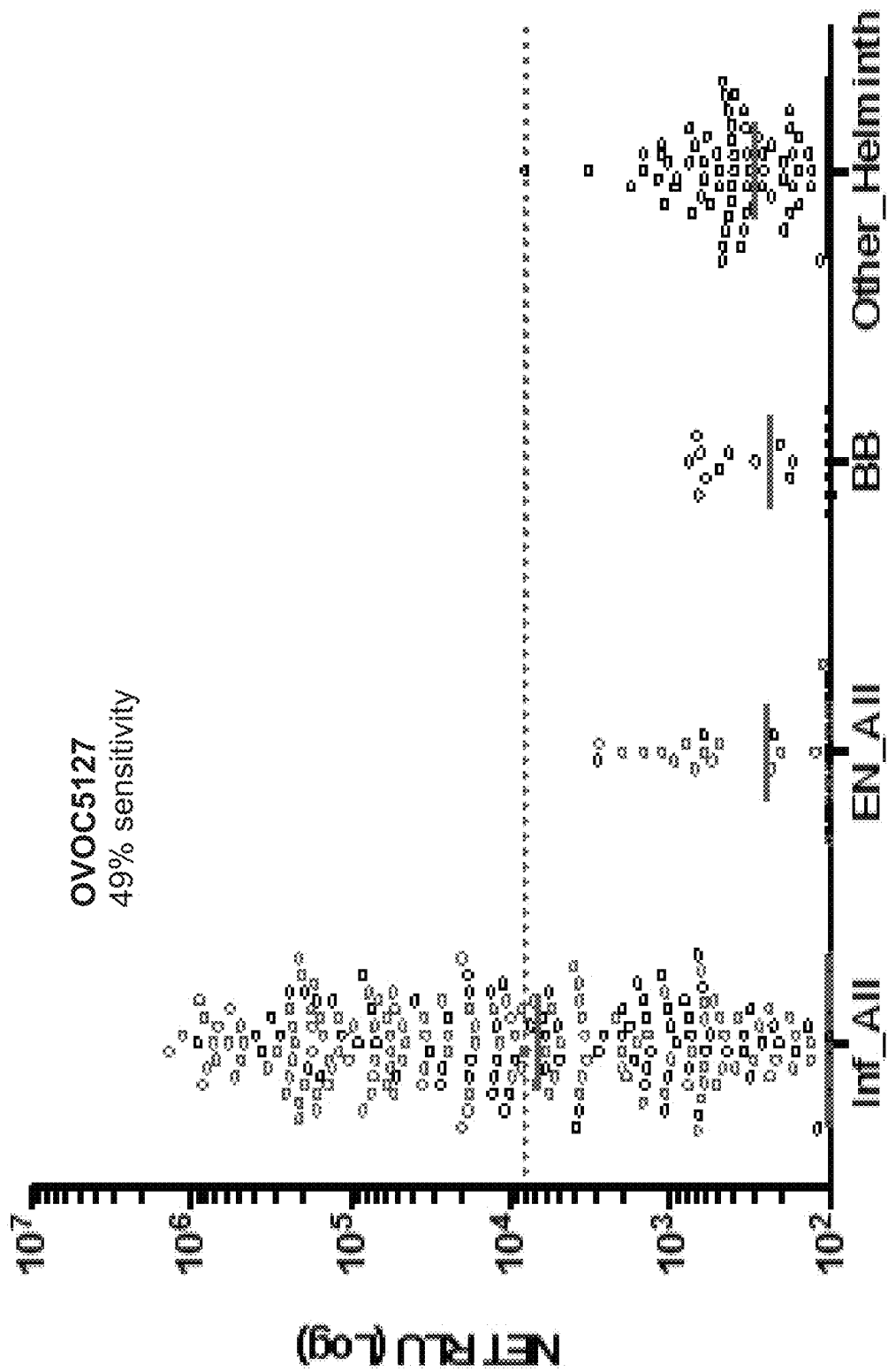
Figure 3E:
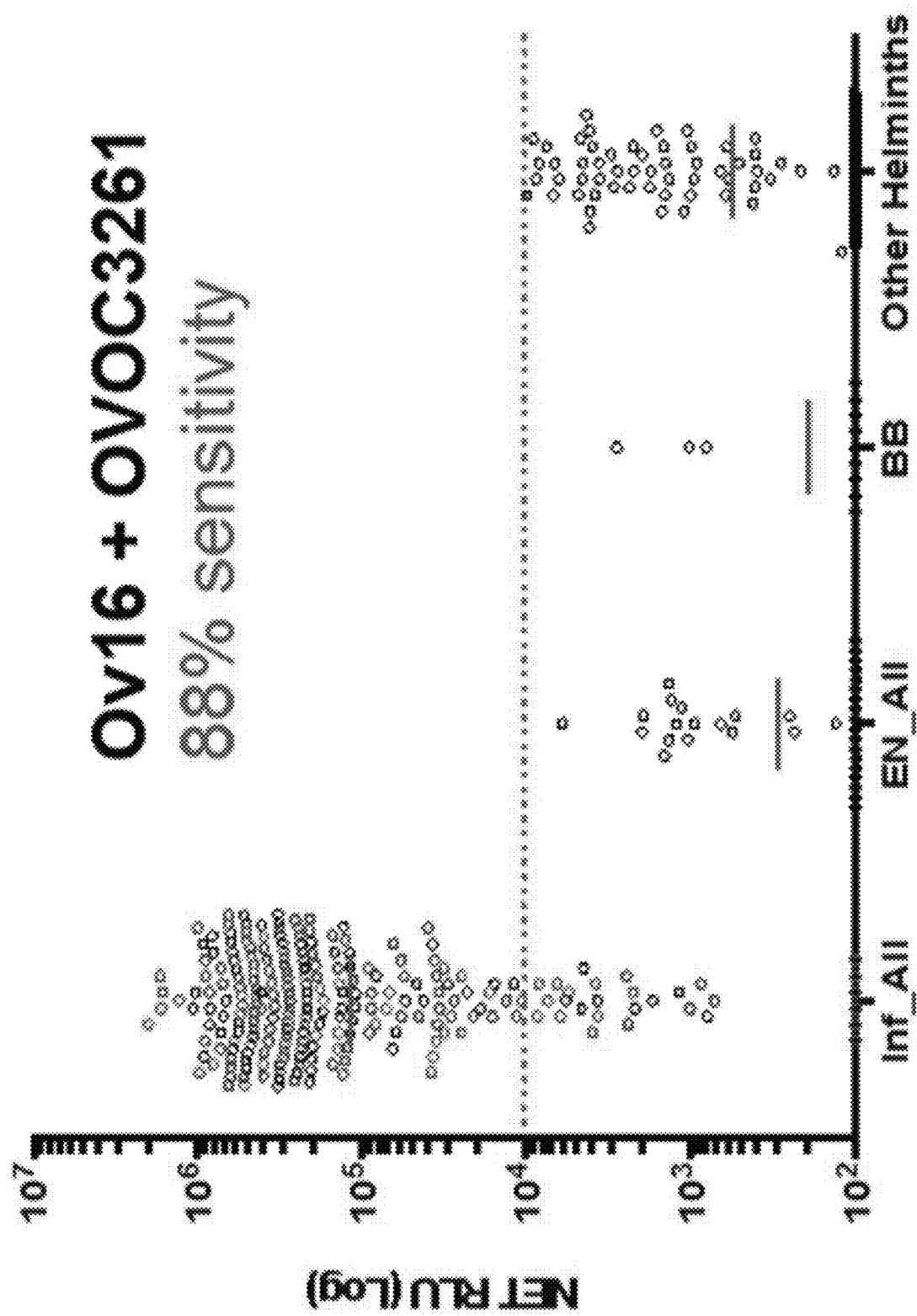
Figure 3F:
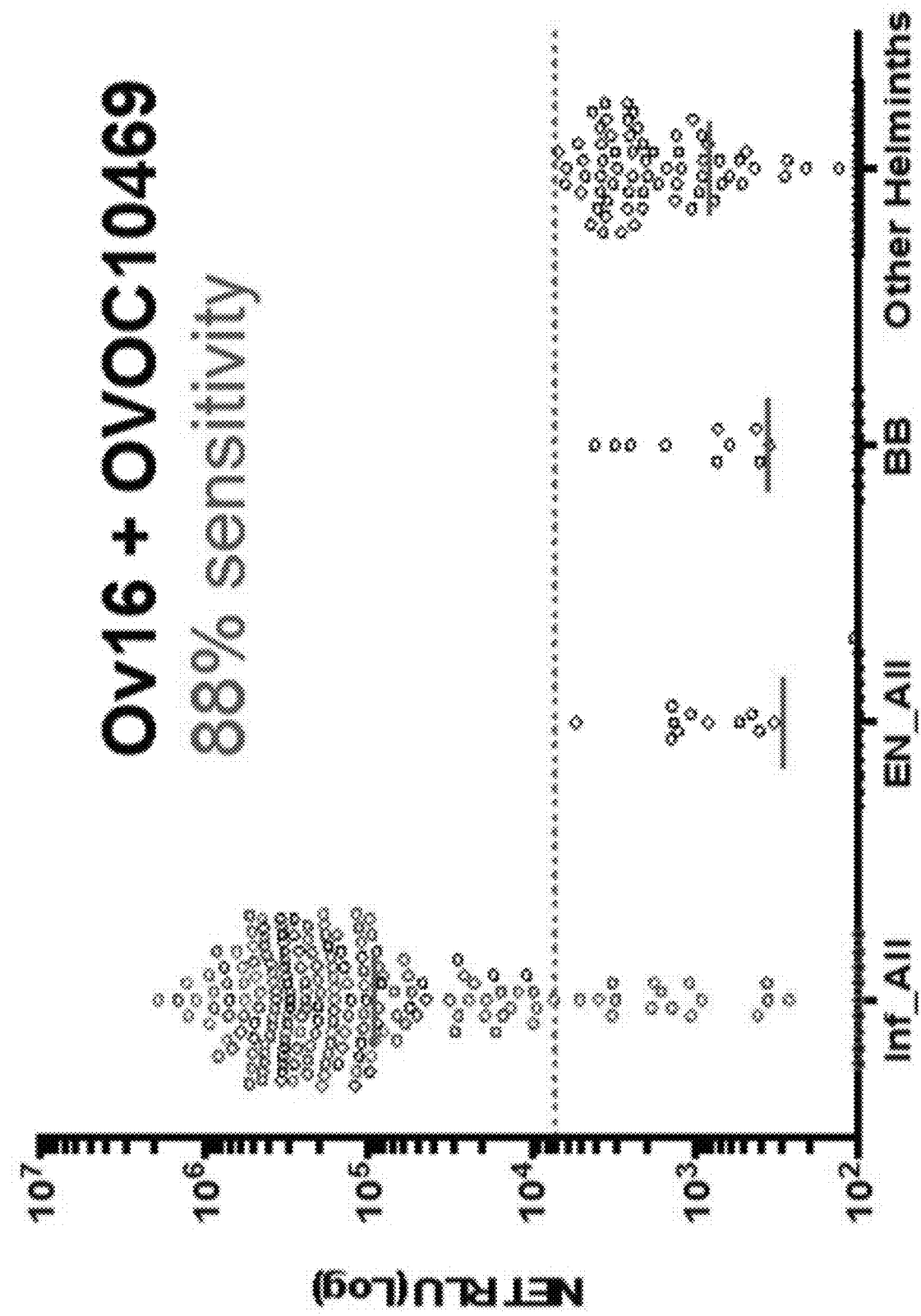
Figure 3G:
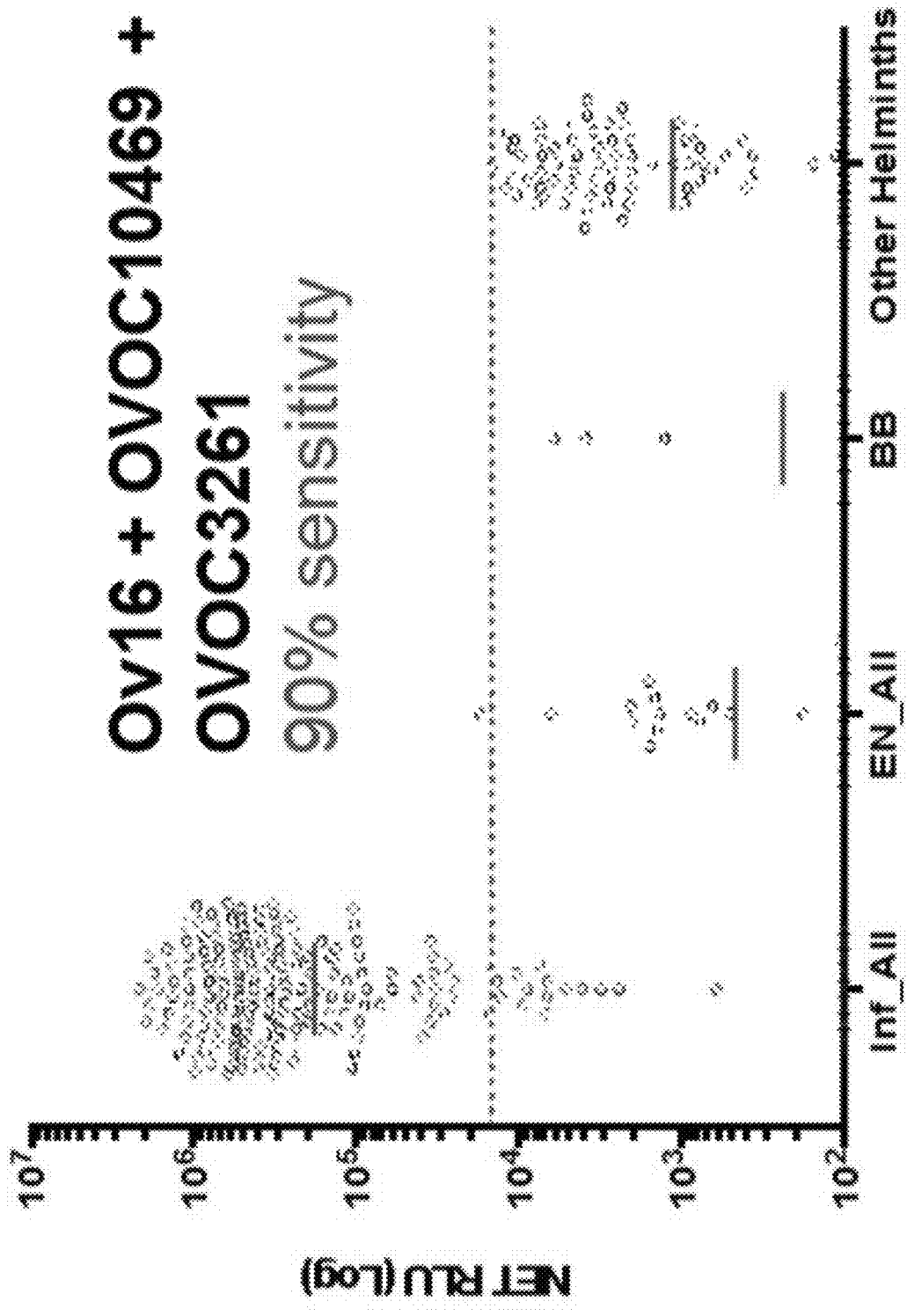
Figure 3H:
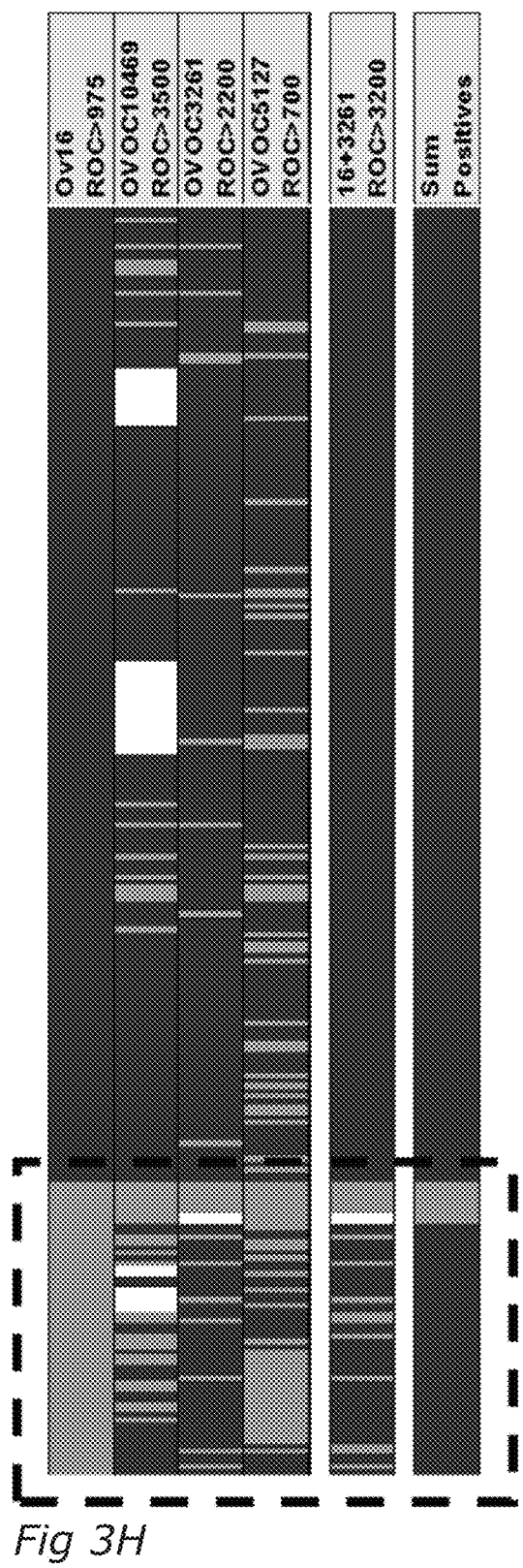

Among the biomarker sequences listed in Table 3, OVOC3261, OVOC5127 and OV10469 were tested for their individual immunoreactivity using a variety of *Onchocerca* microfilaria positive infected sera (truly infected) and a variety of control sera (non-infected (EN_all, BB), infected with unrelated human filarial pathogens or *S. stercoralis*) in immunoassays. As can be seen in FIG. 3, when using a cutoff that gave 100% specificity, OVOC10469 had 78% sensitivity (FIG. 3B), OVOC3261 had 78% sensitivity (FIG. 3C), and OVOC5127 had a sensitivity of 49% (FIG. 3D). Combinations of these newly identified proteins were tested in combination with the known Ov16 (KISAE-NANCKKCTPMLVDSAFKEHGIVPDW- STAPTKLVNVSYNNLTVNLGNELTPTQVKN
QPTKVSWDAEPGALYTLVMTDPDAPSRKNPVFRE-
WHHWLIINISGQNVSSGTVLSDYIGSG
PRKGTGLHRYVFLVYKQPGSITDTQHGG-
NRRNFKVMDFANKHHLGNPVAGNFFQAKHED; SEQ
ID NO:63) (Table 6), it can be seen that the sensitivity increases for all of these combination compared to Ov16 alone. Each individual positive sera was tested against each of the antigens and in combination with all four. As can be seen in Table 6, the combination gets to 97 percent sensitivity (8/245 mf positives being false negatives).

TABLE 6

Reactivity of Ov-infected samples with *O. volvulus* biomarkers

|  | Ov16 | OVOC10469 | OVOC3261 | OVOC5127 | Ov16 OVOC3261 | Combination of 4 biomarkers |
|---|---|---|---|---|---|---|
| Positive | 187 (77%)* | 167 (81%) | 219 (91%) | 172 (70%) | 225 (94%) | 235 (97%) |
| Negative | 53 (23%) | 40 (19%) | 22 (9%) | 71 (29%) | 16 (6%) | 8 (3%) |
| Not tested | 2 | 38 | 4 | 2 | 4 | 2 |

*number of samples (percent of samples tested)

Further analysis demonstrated that OVOC3261, OVOC10469, OVOC8491, OVOC11950, OVOC10602 are microfilaria-specific. Moreover, most of these antigens are relatively invariant based on non-synonymous SNPs and that antibodies of the IgG and IgG₄ isotypes of two of these (OVOC3261 and OVOC10469) only appear after microfilariae appear in the skin of experimentally infected chimpanzees.

Example 6. Immunization of Mice with *O. volvulus* Proteins

Yeast codon optimized DNAs encoding for *O. volvulus* proteins Ov-CPI-2M (OVOC7453), Ov-103 (OVOC4230), and Ov-RAL-2 (OVOC9988), minus the signal peptides at the N-terminus, were synthesized and subsequently subcloned in-frame into the yeast expression vector pPinkα-HC (Life Technologies) with XhoI/KpnI sites and *E. coli* expression vector pET41a (EMDMillipore) with the fusion GST deleted (NdeI/XhoI). The correct open reading frame (ORF) was confirmed by double-stranded sequencing using the vector flanking primers (5'AOX1/CYC1 for pPinkα-HC and T7 promoter/T7 terminator for pET41a). For expression in yeast, the recombinant plasmids were linearized with AflII digestion and then transformed by electroporation into PichiaPink strain #4 with protease A and B knockout (pep4/prb1⁻) to prevent *P. pastoris*-derived protease degradation. Yeast transformants were selected on *P. pastoris* adenine dropout (PAD) selection plates. The expression of recombinant filarial antigens with hexahistidine (6His)-tag at the C-terminus was induced with 0.5% methanol and the soluble recombinant proteins secreted into the culture were purified with immobilized metal ion affinity chromatography (IMAC). For expression in *E. coli*, the recombinant constructs cloned into pET41a were transformed into BL21 (DE3) (EMDMillipore) and recombinant proteins were induced with 1 mM isopropyl-β-thiogalactoside (IPTG) and purified with IMAC.

In order to test the synergistic protection of two or three *O. volvulus* protective antigen combinations, protective *O. volvulus* antigens Ov-103, Ov-RAL-2 and Ov-CPI-2M, were fused together as a triple antigen (Ov-103-RAL-2-CP12-M) or as two double antigens (Ov-103-RAL-2 and Ov-RAL-2-CP12-M) by using a flexible linker (KGPDVPETNQQCPSNTGMTD; SEQ ID NO:50) obtained from Na-ASP-1 structure between two pathogenesis-related (RP) domains. The yeast codon optimized fusion DNAs were subcloned into either yeast expression vector pPICZαA (Life Technologies) or *E. coli* expression vector pET41a with GST knockout. The recombinant fusion proteins were expressed and purified using the same methods described above except for the use of yeast strain *P. pastoris* X-33.

TABLE 7

| SEQ ID NO. | Protein Description | Sequence |
|---|---|---|
| 64 | Ov-103-RAL2-CPI2M fusion protein | DLLSEAGDFFTKHFTDIKSLFAKDEKQLQQSVDRVKDLLATIQDKMSMLQ PLANDMQKTTLGKIGDLISQVNSFRETMSNPKMDFTNKENKWEELLKKIF VTEGLNKVIPLLQKLKNSAKGPDVPETNQQCPSNTGMTDPQRRQQQQQ QQQQQQRDEREIPPFLEGAPPSVIDEFYNLLKTDENKTDQQTEADVEAFIN RLGGSYKVRFTQFMEEVKKARADYERIHQQAVARFSPAAKDADARMSAIA DSPHLTTRQKSQQIQAIMDSLSESVRREIINALSPQEKGPDVPETNQQCPS NTGMTD*KNPSKMESKTGENQDRPVLLGGWEDRDPKDEEILELLPSILMKV* *NEQSKDEYHLMPIKLLKVSSQVVAGVKYKMDVQVARSQCKKSSNEKVDLT* *KCKKLEGHPEKVMTLEVWEKPWENFMRVEILGTKEV* |
| 65 | Ov103-RAL2 fusion protein | DLLSEAGDFFTKHFTDIKSLFAKDEKQLQQSVDRVKDLLATIQDKMSMLQ PLANDMQKTTLGKIGDLISQVNSFRETMSNPKMDFTNKENKWEELLKKIF VTEGLNKVIPLLQKLKNSAKGPDVPETNQQCPSNTGMTDPQRRQQQQQ QQQQQQRDEREIPPFLEGAPPSVIDEFYNLLKTDENKTDQQTEADVEAFIN RLGGSYKVRFTQFMEEVKKARADYERIHQQAVARFSPAAKDADARMSAIA DSPHLTTRQKSQQIQAIMDSLSESVRREIINALSPQE |

TABLE 7-continued

| SEQ ID NO. | Protein Description | Sequence |
|---|---|---|
| 66 | OvRAL2-CPI2M fusion protein | PQRRQQQQQQQQQQQRDEREIPPFLEGAPPSVIDEFYNLLKTDENKTDQ QTEADVEAFINRLGGSYKVRFTQFMEEVKKARADYERIHQQAVARFSPAA KDADARMSAIADSPHLTTRQKSQQIQAIMDSLSESVRREIINALSPQEKGPD VPETNQQCPSNTGMTD*KNPSKMESKTGENQDRPVLLGGWEDRDPKDEEI LELLPSILMKVNEQSKDEYHLMPIKLLKVSSQVVAGVKYKMDVQVARSQCK KSSNEKVDLTKCKKLEGHPEKVMTLEVWEKPWENFMRVEILGTKEV* |

Ov103 sequence—Bold; Linkers—Highlighted; OvRAL2 sequence—underlined; OVCPI-2M sequence—Italics.

The purity and the molecular weight of purified recombinant proteins were analyzed by SDS-PAGE using pre-cast 4-20% Tris-glycine gels (Life Technologies) and stained with Coomassie brilliant blue R-250 (Fisher Scientific).

Male BALB/cByJ mice were purchased from The Jackson Laboratory at 6-8 weeks of age. All mice were housed in micro-isolator boxes in a room that was pathogen-free and under temperature, humidity and light cycle controlled conditions. Mice were fed autoclavable rodent chow and given water ad libitum. All protocols using mice were approved by the Institutional Animal Care and Use Committee.

Mice were immunized with 25 µg of the produced vaccine antigens (Ov-CPI-2M, Ov-103, or Ov-RAL-2, or the two- or three-antigen fusion proteins) in 0.1 ml of Tris-buffered saline (TBS) formulated with 0.1 ml of 1:5 Rehydragel LV (alum) in PBS (General Chemical). Mice were immunized s.c. in the nape of the neck, followed by two booster injections 14 and 28 days later.

The mice were challenged 14 days after the final booster as previously described (Hess et al., Int. J. Parasitology 44:637-646, 2014) with 25 L3 larvae delivered within a diffusion chamber. The diffusion chambers were implanted in a s.c. pocket on a rear flank of each mouse. Recovery of the chambers was performed 21 days later and larval survival was determined based on mobility and morphology of the remaining larvae. Protective immunity was calculated in two ways: (i) percentage of reduction in larvae was calculated as follows: % reduction=((average worm survival in control mice−average worm survival in immunized mice) ÷average worm survival in control mice)×100; and (ii) host protection was calculated as follows: (number of immunized mice with parasite recovery levels below the lower S.D. of parasite recovery in control mice÷total number of immunized mice)×100). Host cells within the diffusion chamber were collected and analyzed by centrifugation onto slides using a Cytospin 3 (Shandon Inc.) and then stained for differential cell counts using Hemastain 3 (Fisher Scientific).

Serum was collected at the time of recovery for antigen-specific IgG analysis. Maxisorp 96-well plates (Nunc Nalgene) were coated with 2 µg/ml of the immunizing recombinant antigen in 50 mM Tris-CI coating buffer, pH 8.8, overnight at 4° C. Plates were washed with deionized water between each step. Plates were blocked with borate buffer solution (BBS) (0.17 M boric acid, 0.12 M NaCl, 0.5% TWEEN 20, 0.025% BSA, 1 mM EDTA, pH 8.2) at room temperature for 30 min. Individual sera were diluted to an appropriate starting concentration with BBS and serially diluted; plates were sealed and incubated at 4° C. overnight. Biotinylated IgG (eBioscience) was diluted 1:250 in BBS and incubated for 1 hr at room temperature, followed by ExtrAvidin Px (Sigma) which was diluted 1:1000 in BBS and incubated for 30 min at room temperature. One component ABTS peroxidase substrate (KPL) was added and O.D.s were read after 30 min at 405 nm in a Bio-Rad iMark Microplate reader (Bio-Rad). ELISA data are presented as endpoint titers which were calculated as the serum dilution from experimental animals that had an O.D. reading three times higher than the O.D. recorded for control serum.

*Onchocerca volvulus* proteins were expressed as soluble recombinant proteins in high yield in *P. pastoris* and *E. coli* BL21(DE3) after being induced with 0.5% methanol for *P. pastoris* and 1 mM IPTG for *E. coli*, and purified with IMAC. Purified recombinant Ov-103, Ov-RAL-2 and Ov-CPI-2M expressed in *P. pastoris* or in *E. coli* migrated at the same molecular mass as calculated by the coding sequence (14.5 kDa, 17.9 kDa and 16.0 kDa, respectively) on SDS-PAGE and Coomassie staining. The fusion recombinant proteins of two or three antigen combination (Ov-103-RAL2, Ov-RAL2-CPI2M and Ov-103-RAL2-CP12M) were also expressed in *P. pastoris* and *E. coli* expression systems as soluble proteins and the purified 500321271 v recombinant fusions were shown at the correct molecular weight as estimated by sequences on SDS-PAGE (50.6 kDa, 32.5 kDa and 35.2 kDa, respectively).

Figure 4A:
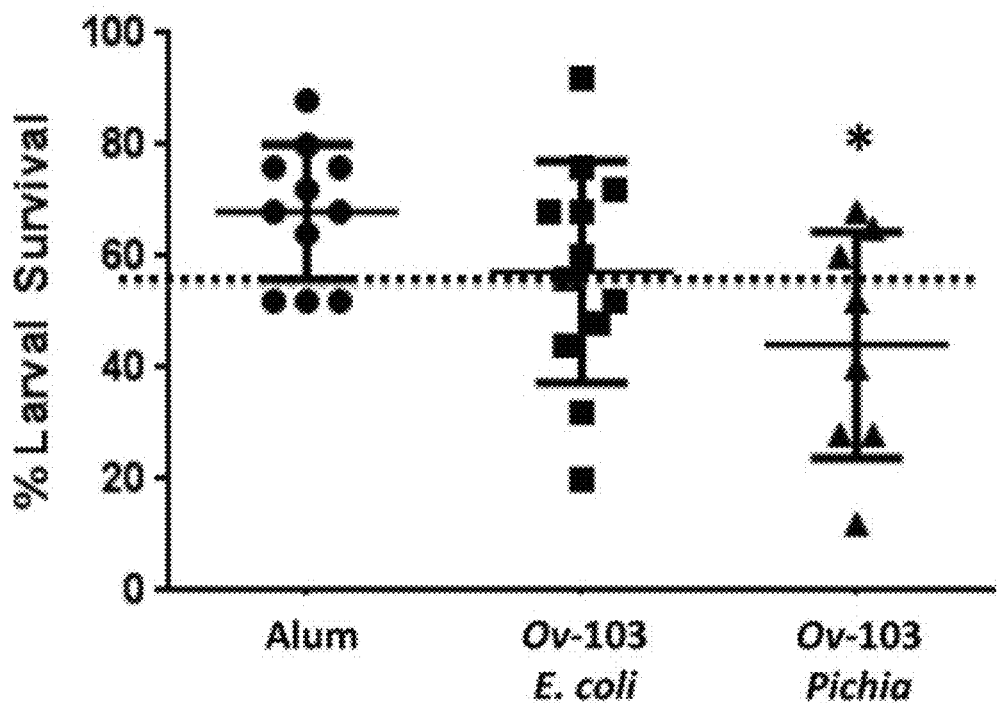
FIG. 4A-C depicts the effect of immunization with a single vaccine antigen expressed by either *Escherichia coli* or *Pichia pastoris* on the development of protective immunity to *O. volvulus* larvae in mice.

In BALB/cByJ mice immunized with Ov-103 with alum prepared in both *P. pastoris* and *E. coli* expression systems, *E. coli*-expressed protein induced an 8% reduction in larval survival and a 50% level of host protection, whereas mice immunized with the *P. pastoris*-expressed protein had a statistically significant 30% reduction in parasite survival and a 63% level of host protection (FIG. 4A). Differential cell counts were performed at the conclusion of the experiments on the diffusion chamber contents. Comparable numbers of total cells ($1.4 \times 10^6 \pm 1.3 \times 10^6$), and percentages of lymphocytes (5±7%), neutrophils (52±20%), macrophages (37±15%) and eosinophils (12±14%) were seen in the control and immunized mice. Parasite-specific antibody titers show equivalent endpoint titers for mice immunized with *P. pastoris* and *E. coli* expressed Ov-103 when measured against both the *P. pastoris* and *E. coli* expressed proteins (Table 8). Correlation analyses were performed between parasite survival and antibody endpoints titers and there were no significant relationships between the amount of antibody produced and the survival of the larvae.

Figure 4B:
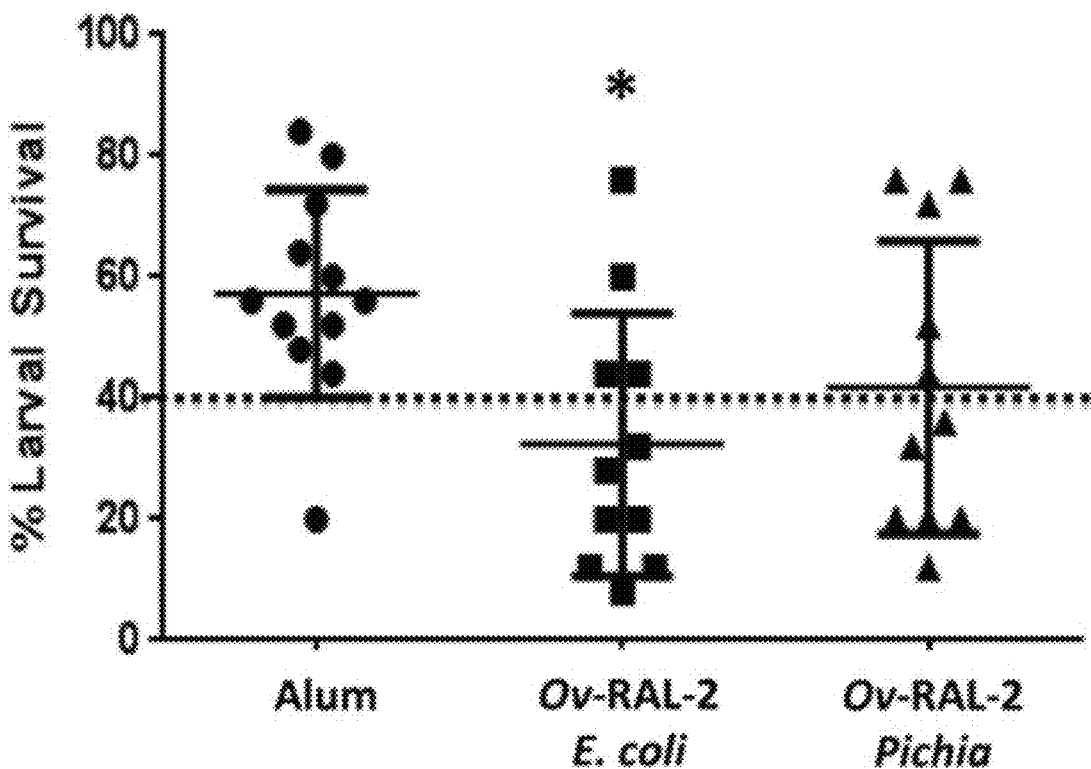

Mice immunized with *E. coli*-expressed Ov-RAL-2 induced a statistically significant 39% reduction in larval survival and a 64% level of host protection, whereas mice immunized with the *P. pastoris*-expressed protein induced a 24% reduction in parasite survival and a 55% level of host protection (FIG. 4B). As with Ov-103, differential cell counts showed comparable numbers of total cells, lymphocytes, neutrophils, macrophages and eosinophils in the control and immunized mice. Parasite-specific antibody titers show equivalent endpoint titers for both the *P. pastoris* and

*E. coli* expressed proteins (Table 8). Again, correlations between parasite survival and antibody endpoints titers did not reveal any significant relationship between the amount of antibody produced and parasite survival.

Figure 4C:
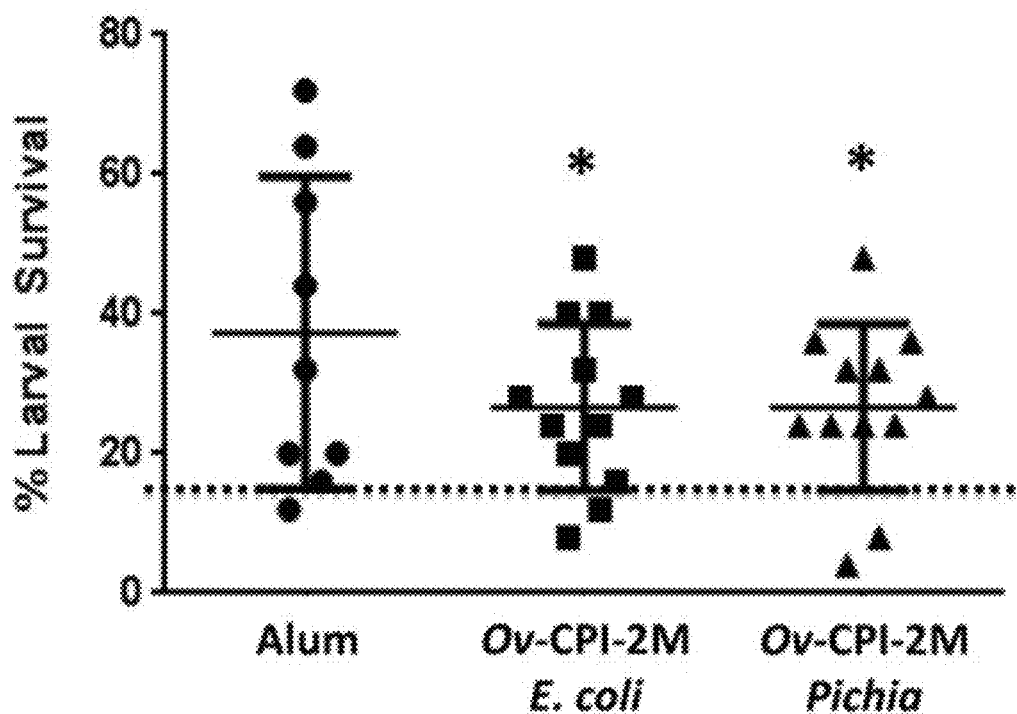

Immunization of mice with Ov-CPI-2M expressed in both *E. coli* and *P. pastoris* induced statistically significant reductions of 30% in larval survival and 17% levels of host protection (FIG. 4C). As with the other two antigens, differential cell counts showed comparable numbers of total and specific cells in the control and immunized mice, and parasite-specific antibody titers had equivalent endpoints (Table 8). There were no significant correlations between antibody endpoint titers and parasite survival.

three-antigen fusion protein and the concurrent immunization resulted in significant levels of protective immunity, with the fusion inducing a 20% reduction in larval survival and a 45% level of host protection and the concurrent immunization resulting in a 25% reduction in parasite survival and a 64% level of host protection (FIG. 7). Analysis of the cells within the diffusion chamber contents showed similar numbers of total cells, lymphocytes neutrophils, macrophages and eosinophils. Antibody titer endpoints were measured against the individual antigens and the fusion protein. Mice immunized with the three antigens concurrently had antibody endpoint titers to the three antigens that were comparable with those seen in mice immunized with

TABLE 8

Geometric mean of IgG endpoint titers following immunization with individual, fusion, or concurrent antigen formulations.

| Immunizing Antigen | Ov-103 | Ov-RAL-2 | Ov-CPI-2M | Ov-RAL-2/103 | Ov-RAL-2/CPI-2M | Ov-RAL-2/103/CPI-2M |
|---|---|---|---|---|---|---|
| Ov-103 *E. coli* | 33,064 | | | | | |
| Ov-103 *P. pastoris* | 35,882 | | | | | |
| Ov-RAL-2 *E. coli* | | 571,055 | | | | |
| Ov--RAL-2 *P. pastoris* | | 519,490 | | | | |
| Ov-CPI-2M *E. coli* | | | 431,803 | | | |
| Ov-CPI-2M *P. pastoris* | | | 462,057 | | | |
| Ov-103/RAL-2 fusion | 317,320 | 439,250 | | 1,509,278 | | |
| Ov-RAL-2/CPI-2M fusion | | 187,884 | 266,079 | | 691,063 | |
| Ov-RAL-2/103/CPI-2M fusion | 90,464 | 146,607 | 165,510 | | | 1,112,542 |
| OV-RAL-2,103, CPI-2M concurrent | 16,019 | 271,416 | 392,676 | | | |

Figure 5A:
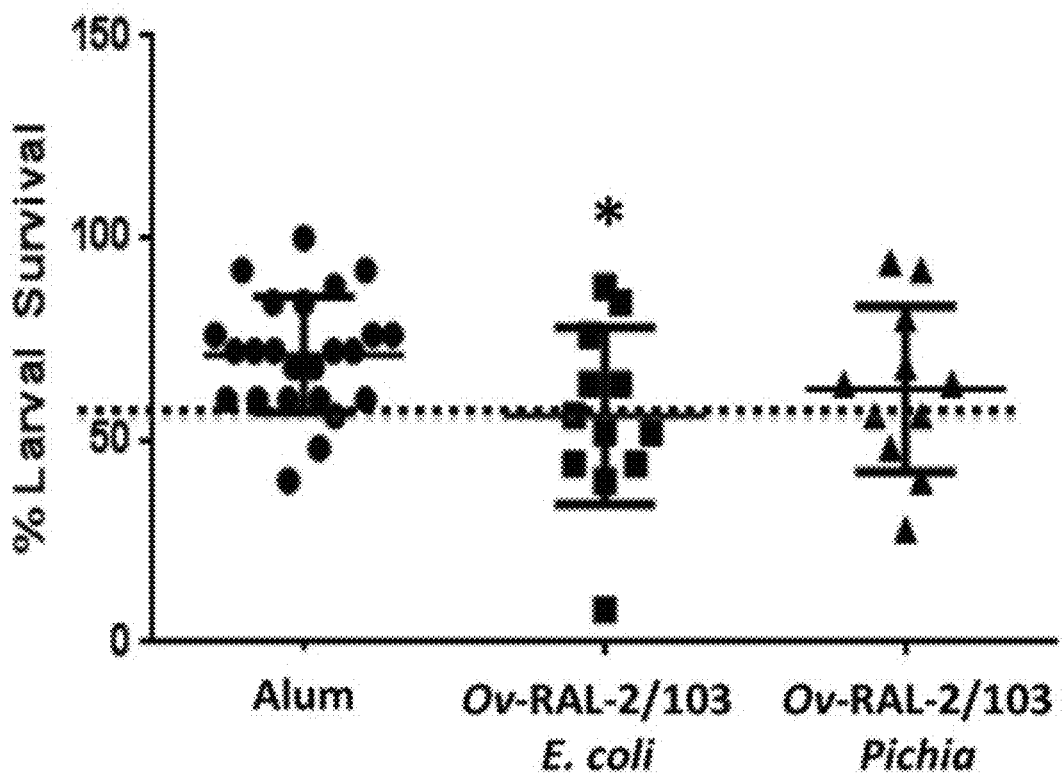
FIG. 5A-B depicts the effect of immunization with fusion antigens on the development of protective immunity to *O. volvulus* larvae in mice.
Figure 5B:
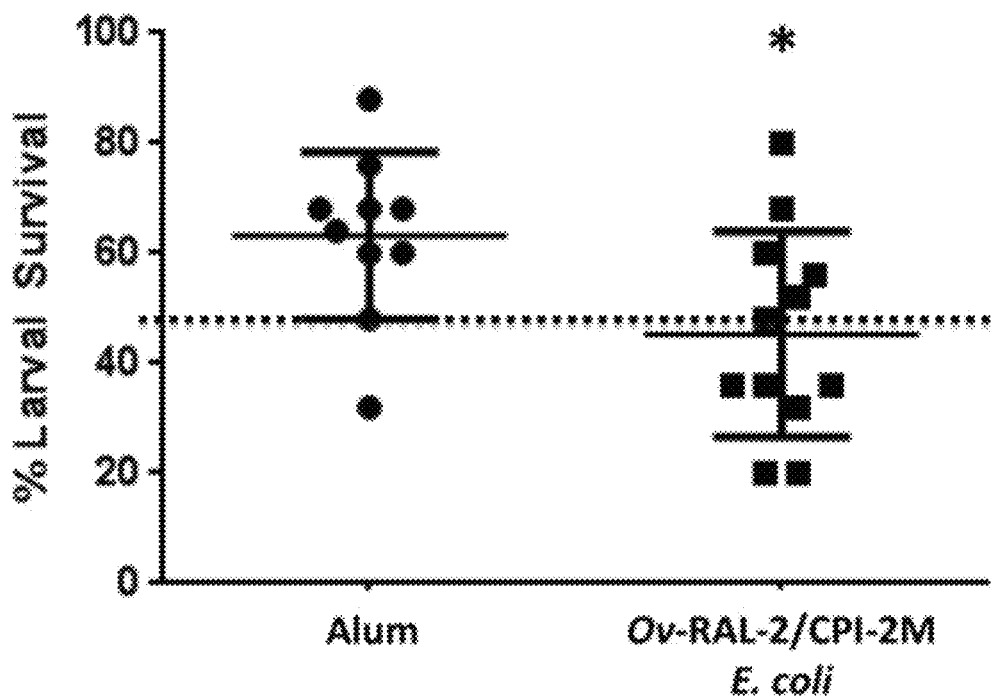
Figure 6:
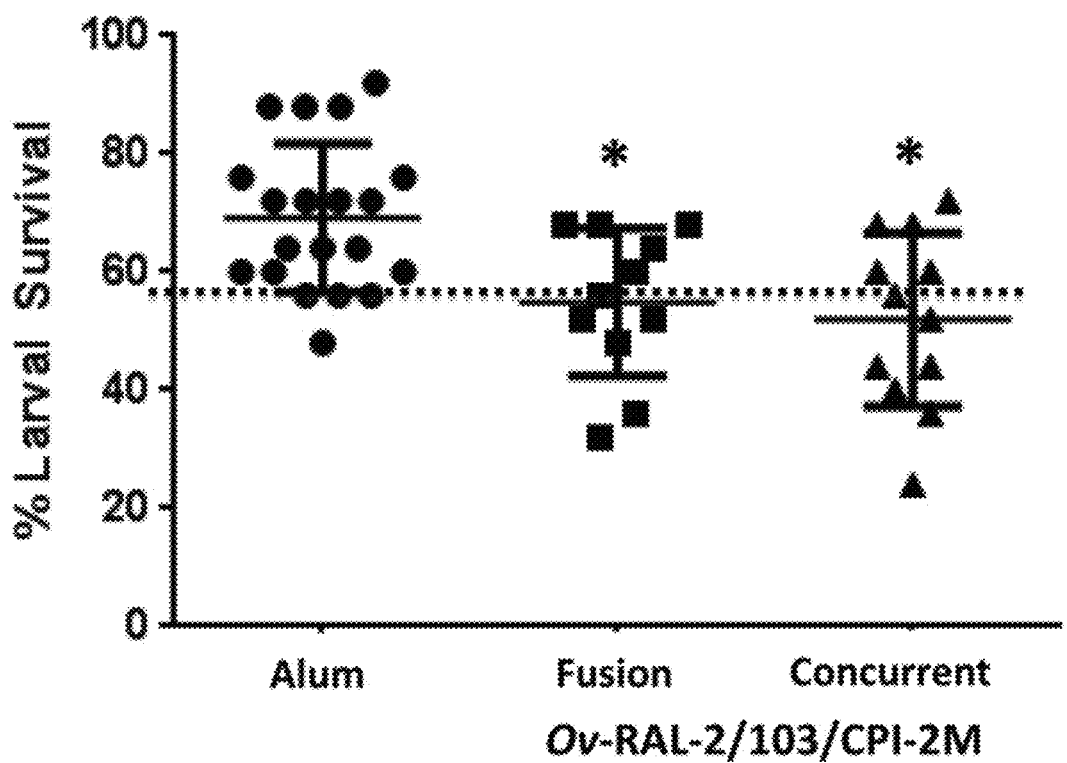
FIG. 6 depicts the comparative effect of immunization with concurrent injections of *O. volvulus* Ov-103 (expressed in *P. pastoris*), Ov-RAL-2 (expressed in *E. coli*) and Ov-CPI-2M (expressed in *E. coli*) compared with immunization with the combined fusion antigen Ov-RAL-2/103/CPI-2M (expressed in *E. coli*). Each dot represents larval recovery from an individual animal. Data presented are mean±S.D. Asterisk represents statistical difference in larval recoveries; P 0.05.

In mice immunized with Ov-RAL-2/103 fusion protein expressed in *P. pastoris* and *E. coli*, *E. coli*-expressed protein significantly reduced larval survival by 21% and provided a 58% level of host protection, whereas immunization with *P. pastoris*-expressed protein only reduced larval survival by 11% and provided a 45% level of host protection (FIG. 5A). Immunization with Ov-RAL-2/CPI-2M *E. coli* fusion protein induced protective immunity with parasite reduction at 34% and a 50% level of host protection (FIG. 5B). Analysis of the cells within the diffusion chamber contents showed similar numbers of total cells, lymphocytes, neutrophils, macrophages and eosinophils. Parasite-specific antibody titer endpoints were measured against the individual antigens and the fusion protein. Antibody endpoint titers for the two fusion proteins were significantly higher than the antibody responses in these mice to the individual antigens of which the fusion was composed. The antibody response to Ov-RAL-2 and Ov-CPI-2M by mice immunized with these antigens as part of a fusion were equivalent to the responses seen in mice immunized with antigen individually. However, the parasite-specific antibody titer endpoint to Ov-103 was approximately eight-fold higher in mice immunized with the antigen as part of a fusion compared with immunization with the individual antigen (Table 8). Once again, there were no significant correlations between antibody endpoints and parasite survival.

A fusion protein consisting of Ov-103, Ov-RAL-2 and Ov-CPI-2M was created to determine whether enhanced protective immunity would be achieved with this triple fused antigen. The Ov-RAL-2/103/CPI-2M *E. coli* fusion was tested in comparison with concurrent immunization consisting of the three antigens injected simultaneously but at different locations on the mice. Immunization with the three individual antigens (Table 8). Mice immunized with the three-antigen fusion protein had endpoint titers to the single antigens that were comparable with the titers seen in mice immunized with individual antigens. Antibody endpoint titers for the three-antigen fusion protein were significantly higher than the antibody responses in these mice to the individual antigens of which the fusion was composed (Table 8). There were no significant correlations between antibody endpoints and parasite survival.

Example 7. Orthologs of *O. volvulus* Proteins Induce Protective Immunity to Other Filarial Parasites

*Brugia malayi* is a filarial parasite, one of the three causative agents of lymphatic filariasis in humans. Lymphatic filariasis, also known as elephantiasis, is a condition characterized by swelling of the lower limbs. The *B. malayi* Bm-103 and Bm-RAL-2 proteins are orthologous to *O. volvulus* Ov-103 and Ov-RAL-2 which are candidates for development of an *O. volvulus* immunogenic composition (Table 9). The *B. malayi* gerbil model was used to confirm the efficacy of these *O. volvulus* orthologs, alone or in combination, against adult worms. Efficacy of recombinant Bm-103 and Bm-RAL-2 administered individually, concurrently, or as a fusion protein were tested in gerbils using alum as adjuvant. Immunization with Bm-103 resulted in worm reductions of 39%, 34%, and 22% on 42, 120 and 150 days post infection (dpi), respectively, and immunization with Bm-RAL-2 resulted in worm reductions of 42%, 22%, and 46% on 42, 120, and 150 dpi, respectively. Immunization with a fusion protein comprised of Bm-103 and Bm-RAL-2 resulted in improved efficacy with significant reduction of worm burden of 51% and 49% at 90 dpi, as did the concurrent immunization with Bm-103 and Bm-RAL-2, with worm reduction of 61% and 56% at 90 dpi. Immunization with Bm-103 and Bm-RAL-2 as a fusion protein or concurrently not only induced a significant worm reduction of 61% and 42%, respectively, at 150 dpi, but also significantly reduced the fecundity of female worms as determined by embryograms. Elevated levels of antigen-specific IgG were observed in all immunized gerbils. Serum from gerbils immunized with Bm-103 and Bm-RAL-2 individually, concurrently, or as a fusion protein killed third stage larvae in vitro when combined with peritoneal exudate cells.

Thus, immunization with Bm-103 and Bm-RAL-2 individually conferred protection against *B. malayi* infection in gerbils.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

---

What is claimed is:

1. An immunogenic composition for administration to a canine subject, the composition comprising isolated *Dirofilaria immitis* proteins consisting of:
   a first protein having at least 95% sequence identity to SEQ ID NO:48 and a second protein having at least 95% sequence identity to the full length mature amino acid sequence of SEQ ID NO: 49; and
   an adjuvant.

2. The immunogenic composition of claim 1, wherein the two isolated *D. immitis* proteins are present in the immunogenic composition as a mixture.

3. The immunogenic composition of claim 1, wherein the two isolated *D. immitis* proteins are present in the immunogenic composition as a fusion protein comprising the amino acid sequences of the two proteins.

4. The immunogenic composition of claim 3, wherein the fusion protein optionally further comprises at least one linker sequence separating the two amino acid sequences.

5. The immunogenic composition of claim 1, wherein the second protein has the amino acid sequence of the full length mature amino acid sequence of SEQ ID NO:49.

6. The immunogenic composition of claim 1, wherein the immunogenic composition further comprises a third protein having at least 95% sequence identity to the full length mature amino acid sequence of the *D. immitis* protein of one of SEQ ID NOs: 33-47.

7. The immunogenic composition of claim 6, wherein the immunogenic composition further comprises a fourth protein having at least 95% sequence identity to the full length mature amino acid sequence of the *D. immitis* protein of one of SEQ ID NOs: 33-47.

8. The immunogenic composition of claim 7, wherein the third and fourth proteins are different proteins.

9. An immunogenic composition for administration to a canine subject, the composition comprising:
   (a) isolated *Dirofilaria immitis* proteins consisting of:
      (i) a first protein having at least 95% sequence identity to SEQ ID NO:48;
      (ii) a second protein having at least 95% sequence identity to the full length mature amino acid sequence of the *D. immitis* protein of one of SEQ ID NOs: 33-47 or 49; and
      (iii) a third protein having at least 95% sequence identity to the full length mature amino acid sequence of the *D. immitis* protein of one of SEQ ID NOs: 33-47 or 49; and
   (b) an adjuvant;
      wherein the second and third proteins are different proteins, and wherein the immunogenic composition induces an immune response against the *D. immitis* proteins in the canine subject.

10. An immunogenic composition for administration to a canine subject, the composition consisting essentially of:
    (a) isolated *Dirofilaria immitis* proteins consisting of:
       (i) a first protein having at least 95% sequence identity to SEQ ID NO:48 and (ii) a second protein having at least 95% sequence identity to the full length mature amino acid sequence of SEQ ID NO:49; and (b) an adjuvant.

\* \* \* \* \*

SEQUENCE LISTING

```
<160> NUMBER OF SEQ ID NOS: 66

<210> SEQ ID NO 1
<211> LENGTH: 98
<212> TYPE: PRT
<213> ORGANISM: Onchocerca volvulus

<400> SEQUENCE: 1

Asn Ile Ala Phe Ala Pro Asn Pro Lys Asp Ser Asn Asn Glu Leu Phe
```

-continued

```
1               5                   10                  15
Ala Asp Ala Glu Ser Ala Leu Gly Ser Glu Tyr Ala Gln Phe Val Glu
            20                  25                  30

Gln Ser Lys Gln His Lys Pro Val Tyr Phe Ser Asp Asn Gln Asn Thr
        35                  40                  45

Leu Glu Thr Ile Lys Leu Glu Ser Ile Pro Asn Pro Glu Thr Glu Thr
    50                  55                  60

Ala Tyr Pro Met Phe Ile Cys Gly Phe Leu Gly Cys Met Lys Lys Met
65                  70                  75                  80

Asn Ser Val Glu Glu Tyr Leu Glu His Phe Lys Met His Glu Lys Gln
                85                  90                  95

Gly Tyr

<210> SEQ ID NO 2
<211> LENGTH: 103
<212> TYPE: PRT
<213> ORGANISM: Onchocerca volvulus

<400> SEQUENCE: 2

Tyr Pro Thr Glu Lys Glu Thr Val Glu Pro Ile Asp Thr Met Val Lys
1               5                   10                  15

Asp Asp Ile Asp Leu Val Lys Ala Glu Val Ala Glu Ala Glu Glu Ala
            20                  25                  30

Asp Val Glu Lys Glu Val Ala Glu Leu Thr Glu Glu Glu Ala Ala Glu
        35                  40                  45

Ile Ala Glu Val Leu Asp Glu Met Glu Glu Glu Phe Phe Ala Phe Leu
    50                  55                  60

Leu Phe Asp Phe Ile Leu Asp Leu Phe Arg Glu Thr Leu Glu Lys Asn
65                  70                  75                  80

Ser Glu Ser Gln Glu Ala Ser Ile Asp Glu Val Met Pro Glu Ile Gln
                85                  90                  95

Gly Val Ser Ala Glu Glu Ala
            100

<210> SEQ ID NO 3
<211> LENGTH: 119
<212> TYPE: PRT
<213> ORGANISM: Onchocerca volvulus

<400> SEQUENCE: 3

Phe Arg Thr Gln Ser Ile Gly Ile Arg Gly Arg Leu Met Cys Gly Ser
1               5                   10                  15

Lys Pro Ala Ser Asn Glu Arg Ile Lys Leu Trp Glu Glu Asp Ser Asp
            20                  25                  30

Asp Leu Leu Asp Gln Gly Tyr Thr Asp Glu Asn Gly Glu Phe Leu Leu
        35                  40                  45

Lys Gly Asp Thr Val Glu Leu Thr Pro Ile Asp Pro Val Phe Lys Val
    50                  55                  60

Tyr His Asp Cys Asp Asp Gly Ile Lys Pro Gly Lys Arg Lys Val Lys
65                  70                  75                  80

Phe Lys Ile Pro Lys Ser Tyr Ile Thr Glu Gly Lys Thr Pro Lys Lys
                85                  90                  95

Ile Phe Asp Leu Gly Thr Leu Asn Leu Glu Thr Ile Phe Asn Asp Glu
            100                 105                 110

Glu Arg Glu Leu Ile Val Thr
        115
```
<210> SEQ ID NO 4
<211> LENGTH: 149
<212> TYPE: PRT
<213> ORGANISM: Onchocerca volvulus

<400> SEQUENCE: 4

```
Ser Tyr Cys Glu Asp Trp Asp Pro Glu Asp Phe Pro Ser Phe Val Leu
1               5                   10                  15

Lys Leu Ser Gln Asn Ala Thr Glu Glu Phe Cys Glu Leu Tyr Glu Met
            20                  25                  30

Glu Met Glu Val Pro Ile Asn Lys Phe Tyr Asp Met Leu Arg Lys Trp
        35                  40                  45

Ala Glu Lys Tyr Ser Val Gln Ala Glu Thr Asn Arg Phe Ile Ala Glu
    50                  55                  60

Glu Met Asn Tyr Asp Lys Met Gln Ser Lys Val Leu Met Glu Arg Leu
65                  70                  75                  80

Gln Ala Ser Asn Gly Thr Thr Glu Val Lys Gly Val Leu Glu Lys Ala
                85                  90                  95

Leu Lys Leu Gln Glu Ser Met His Leu Ser Pro Asp Tyr Ile Gln Asn
            100                 105                 110

Val Ile Asp Thr Met Met Glu Asn Leu Pro Ile Asp Lys Gln Asn Glu
        115                 120                 125

Ala Thr Leu Leu Trp Asn Ser Leu Tyr Pro Asp Asp Ile Tyr Asn Glu
    130                 135                 140

Cys Gly Pro Arg Phe
145
```

<210> SEQ ID NO 5
<211> LENGTH: 426
<212> TYPE: PRT
<213> ORGANISM: Onchocerca volvulus

<400> SEQUENCE: 5

```
Ala Pro Pro Asn Arg Asp Thr Ala Asp Asp Leu Gln Asn Ala Asp Met
1               5                   10                  15

Gln Arg Gln Trp Glu Gln Glu Gln Arg Gln Arg Glu Glu Val Gln Lys
            20                  25                  30

Glu Glu Ile Ala Lys Tyr Val Lys Tyr Met Arg Tyr Leu Glu Thr Val
        35                  40                  45

Leu Asn Ile Leu Gln Ala Thr Pro Gln Trp Lys Glu Ala Met Gln Ser
    50                  55                  60

Met Thr Gln Glu Glu Met Arg Gly Gly Lys Ile Ala Glu Met Val Asp
65                  70                  75                  80

Lys Leu Glu Pro His Ile Ile Glu Gln Leu Ala Lys Ala Lys Ile Leu
                85                  90                  95

Glu Leu Gln Arg Leu Glu Gln Glu Ile Lys Asp Gln Leu Asn Ala Asp
            100                 105                 110

Gly Gly Ala Thr His Asn Ile Lys Val Ser Glu Ile Leu Thr Val Cys
        115                 120                 125

Leu Lys Glu Gly Phe Lys Lys Pro Ser Asn Leu Gly Ile Pro Glu His
    130                 135                 140

Leu Asp Phe Asn Asn Trp Glu Thr Phe Ser Gln Glu Asp Leu Arg Lys
145                 150                 155                 160

Leu Ile Val Lys Ile Val Thr Asp Met Asp Glu Leu Glu Glu Gln Arg
                165                 170                 175
```

Lys Gln Asp Phe Lys Gln Tyr Glu Met Lys Lys Ala Glu Glu Asp
            180                 185                 190

His Lys Met Gln Ala Lys Met Ile Gln Thr Glu Arg Glu Glu Tyr Ile
        195                 200                 205

Arg Gln Met Glu Glu Gln Arg Arg His Asn Lys His Glu Pro Leu
    210                 215                 220

Lys His Pro Gly Ser Arg Asn Gln Leu Arg Lys Val Trp Glu Asp Thr
225                 230                 235                 240

Asp Lys Leu Asp Lys Asp Ala Tyr Asp Pro Thr Thr Leu Phe Gly Leu
                245                 250                 255

His Asp Arg Asn Asn Asp Gly Tyr Trp Ser Tyr Asp Glu Leu Asn Thr
            260                 265                 270

Ile Phe Leu Pro Glu Ile Glu Lys Leu Asn Asn Phe Ser Asp Val Glu
        275                 280                 285

Arg Leu Glu Glu Leu Tyr Arg Met Arg Asp His Val Met Lys Gln Met
    290                 295                 300

Asp Thr Asp Gly Asp His Arg Ile Ser Arg Ala Glu Phe Leu Ala Asp
305                 310                 315                 320

Arg Glu Ala Gln Glu Lys Pro Asp Gln Gly Trp Glu Asp Ile Gly
                325                 330                 335

Asp Lys Asp Gln Tyr Thr Lys Glu Glu Leu Glu Ile Phe Glu Lys Glu
            340                 345                 350

Tyr Ala Lys Gln Gln Gly Trp Gly Glu Tyr Ala Tyr Ser Thr Pro Ala
        355                 360                 365

Pro Thr Pro Asp Pro Ser Arg Met Ile Gln Pro Asp Gln Ala Pro Met
    370                 375                 380

Gln Arg Leu Asp Ala Pro Ser Asp Gln Val Gly Asp Met Phe Ala Gln
385                 390                 395                 400

Gln Ser His Gln Ile Pro Val Lys His Val Glu Pro Ile Gln Ser Val
                405                 410                 415

Gln Gln Gln Gln Met Asp Glu Val Asn Ser
            420                 425

<210> SEQ ID NO 6
<211> LENGTH: 231
<212> TYPE: PRT
<213> ORGANISM: Onchocerca volvulus

<400> SEQUENCE: 6

Phe Pro Thr Glu Ala Asn Pro Ala Val Gly Thr Asp Asn Ala His Glu
1               5                   10                  15

Asp Asn Leu Thr Thr Glu Glu Lys Met Gln Leu Lys Lys Phe Ala Lys
            20                  25                  30

Thr Asn Ala Ala Asn Phe Ser Leu Thr Asp Pro Glu Phe Ile Asp Gly
        35                  40                  45

Leu Lys Asn Glu Ala Ala Gly Leu Phe Ser Lys Leu Thr Gly Leu Arg
    50                  55                  60

Asp Ile Ile Asn Ala Lys Leu Asp Thr Met Gln Pro Glu Ser Arg Leu
65                  70                  75                  80

Phe Ile Glu Lys Leu Leu Arg Arg Phe Leu Ala Ala Phe Ser His Asp
                85                  90                  95

Gly Leu Met Asn Ile Leu Glu Ser Leu Lys Gly Phe Gly Lys Glu Val
            100                 105                 110

Ile Asp Met Phe Asp Gly Leu Ser Arg Pro Ile Gln Asn Asp Ile Leu

```
            115                 120                 125
Asn Ala Phe Pro Leu Val Gly Ser Tyr Ile Thr Ser Asp Ile Ala Arg
    130                 135                 140

Leu Met Leu Arg Lys Leu Ala Glu Leu Asp Leu Leu Ser Arg Lys Ser
145                 150                 155                 160

Thr Leu Thr Pro Thr Val Asp Gln Phe Asn Asp Ser Gly Lys His
                165                 170                 175

Phe Pro Arg Pro Gln Val Ile Glu Pro Glu Pro Glu Asn Ser Asp
                180                 185                 190

Pro Glu Asp Ala Gln Ser Thr Asp Tyr Gly Lys Lys Val Val Thr
                195                 200                 205

Thr Thr Thr Phe Pro Ile Ile Thr Gly Glu Glu Asp Glu Ile Leu Val
    210                 215                 220

Lys Lys Ile Val Glu Asn Lys
225                 230

<210> SEQ ID NO 7
<211> LENGTH: 83
<212> TYPE: PRT
<213> ORGANISM: Onchocerca volvulus

<400> SEQUENCE: 7

Ile Pro Leu Pro Glu Glu Leu Asp Tyr Asp Gly Glu Ile Pro Asn Cys
1               5                   10                  15

Arg Asp Gly Glu Lys Pro Leu Leu Ala Ala Asp Ile Gly Val Tyr Thr
                20                  25                  30

Cys Asp Lys Asn Cys Pro Lys Gly Phe Arg Cys Glu Tyr Arg Thr Met
            35                  40                  45

Asp Ser Thr Ser Lys Lys Gly Ile Cys Cys Pro Asn Leu Lys Glu Leu
        50                  55                  60

Ala Lys Ile Tyr Ser Glu Asp Glu Glu Val Asp Lys Ser Ile Lys Lys
65                  70                  75                  80

Ser Asn Ile

<210> SEQ ID NO 8
<211> LENGTH: 209
<212> TYPE: PRT
<213> ORGANISM: Onchocerca volvulus

<400> SEQUENCE: 8

Met Ile Ser Cys Phe Ala Leu Pro Phe Pro His Val Cys Tyr Met Ala
1               5                   10                  15

Tyr Cys Thr Gln Val Ile Ala Ser Ile Met Lys Gly Trp Asn Gln Asn
                20                  25                  30

Phe Arg Phe Ser Thr Val Ile Tyr Leu Phe Arg Asn Ile Phe Ser Ser
            35                  40                  45

Ser Val Ile Ser Cys Val Asn Met Ile Leu Ser Ser Thr Phe Tyr Ala
        50                  55                  60

Leu Leu Phe Val Ser Ala Val Val Ile Val Glu Ala Met Pro Ala Ser
65                  70                  75                  80

Glu Ser Thr Tyr Ser Val Ile Ile Ile Arg Ile Asn Asp Thr Thr Cys
                85                  90                  95

Lys Ile Glu Asp Gly Val Val Ser Val Asn Gly Gln Val Ile Gly Asn
            100                 105                 110

Leu Thr Glu Glu Gln Lys Glu Glu Leu Glu Ala Tyr Asn Val Gln Thr
        115                 120                 125
```

```
Gln Gly Trp Phe Gln Gln Leu His Gln Lys Ile Glu Glu Leu Phe Lys
            130                 135                 140

Thr Phe Phe Gly Ser Ile Lys Ser Met Trp Lys His Ser Pro Ile Ser
145                 150                 155                 160

Gly Ser Glu Ser Ser Pro Gln Ser Ser Thr Pro Asp Asn Ile Ile Thr
                165                 170                 175

Asp Lys Leu Asp Asp Gln Asp Arg Arg Leu Lys Asp Gln Gly Asp Ser
            180                 185                 190

Glu Asn Ser Ser Leu Phe Gly Leu Lys Leu Pro Ser Phe Cys Lys Val
            195                 200                 205

Asn
```

<210> SEQ ID NO 9
<211> LENGTH: 128
<212> TYPE: PRT
<213> ORGANISM: Onchocerca volvulus

<400> SEQUENCE: 9

```
Phe Arg Ser Leu Lys Ile Gly Arg Lys Gln Ser Thr Ala Val Lys Gly
1               5                   10                  15

Val Leu Thr Cys Asn Gly Lys Pro Ala Val Asn Val Lys Val Lys Leu
            20                  25                  30

Tyr Asn Asp Ser Gln Gly Arg Tyr Val Glu Asn Ser Met Asp Glu Gly
            35                  40                  45

Lys Thr Asp Ser Glu Gly Arg Phe Leu Leu Gln Gly His Glu Thr Ser
        50                  55                  60

Ile Thr Ser Ile Asp Pro Ile Leu Lys Leu Tyr His Asn Cys Asp Val
65                  70                  75                  80

Glu Asn Ala Gln Cys Leu Lys Arg Phe Ser Ile Leu Ile Pro Asn Asp
                85                  90                  95

Phe Val Ser Glu Gly Leu Glu Pro Lys Lys Thr Phe Asp Met Gly Thr
            100                 105                 110

Leu Asn Leu Gly Gly Lys Phe Phe Asp Glu Gly Arg Glu Cys Ala Ser
            115                 120                 125
```

<210> SEQ ID NO 10
<211> LENGTH: 256
<212> TYPE: PRT
<213> ORGANISM: Onchocerca volvulus

<400> SEQUENCE: 10

```
Gln Ile Ile Gly Ser Phe Asn Gly Asn Tyr Ala Gly Asp Gly Ser Leu
1               5                   10                  15

Asn Asn Asn Ala Asn Ser Phe Gly Glu Arg Thr Thr Thr Thr Arg Ser
            20                  25                  30

Thr Ser Arg Pro Ser Leu Pro Pro Arg Pro Gly Tyr Pro Ser Arg Pro
            35                  40                  45

Gly Tyr Pro Phe Lys Pro Gly Phe Pro Pro Arg Gly Pro Pro Ile Pro
        50                  55                  60

Tyr Pro His Gly Lys Pro Ser Gly Pro Arg Tyr Pro Cys Tyr Gly Gly
65                  70                  75                  80

Tyr Gly Gly Tyr Gly His Pro Gly Tyr Gly Pro Phe Gly Gly Asn Gly
            85                  90                  95

Tyr Leu Gly Tyr Thr Val Cys Ser Gly Arg Gly Glu Phe Gly Gly Tyr
            100                 105                 110
```

```
Gly Pro Gly Leu Gly Gly Gly Thr Gly Leu Gly Gly Leu Gly Pro Gly
            115                 120                 125

Glu Phe Gly Gly Tyr Gly Pro Gly Leu Gly Gly Thr Gly Leu Gly
        130                 135                 140

Gly Leu Gly Pro Gly Gly Phe Gly Gly Ile Gly Pro Gly Leu Gly Gly
145                 150                 155                 160

Gly Gly Gly Leu Gly Gly Pro Gly Arg Gly Gly Phe Ala Tyr Gly
                    165                 170                 175

Pro Gly Leu Gly Gly Arg Gly Leu Gly Gly Pro Gly Pro Gly Gly
            180                 185                 190

Phe Asp Gly Tyr Gly Pro Gly Leu Gly Gly Arg Pro Tyr Pro Gly Gly
        195                 200                 205

Tyr Gly Arg Phe Tyr Gly Pro Gly Pro Tyr Pro Gly Asp Arg Leu Asp
210                 215                 220

Pro Arg Gly Leu Ser Glu Ser Gly Arg Pro Arg Thr Arg Leu Ala Ser
225                 230                 235                 240

Tyr Asn Arg Asn Asp Arg Gly Thr Gln Phe Ser Tyr Ile Arg Asp Arg
                    245                 250                 255

<210> SEQ ID NO 11
<211> LENGTH: 280
<212> TYPE: PRT
<213> ORGANISM: Onchocerca volvulus

<400> SEQUENCE: 11

Met Thr Asn Glu Tyr Glu Thr Asn Tyr Pro Val Pro Tyr Arg Ser Lys
1               5                   10                  15

Leu Thr Glu Ser Phe Glu Pro Gly Gln Thr Leu Leu Val Lys Gly Lys
            20                  25                  30

Thr Ala Glu Asp Ser Val Arg Phe Thr Ile Asn Leu His Asn Thr Ser
        35                  40                  45

Ala Asp Phe Ser Gly Asn Asp Val Pro Leu His Ile Ser Val Arg Phe
    50                  55                  60

Asp Glu Gly Lys Ile Val Phe Asn Thr Phe Ser Lys Gly Glu Trp Gly
65                  70                  75                  80

Lys Glu Glu Arg Lys Ser Asn Pro Tyr Lys Lys Gly Asp Asp Ile Asp
                85                  90                  95

Ile Arg Ile Arg Ala His Asp Ser Lys Tyr Thr Ile Tyr Val Asp Gln
            100                 105                 110

Lys Glu Val Lys Glu Tyr Glu His Arg Val Pro Leu Ser Ser Val Thr
        115                 120                 125

His Phe Ser Ile Asp Gly Asp Val Leu Val Thr Tyr Ile His Trp Gly
    130                 135                 140

Gly Lys Tyr Tyr Pro Val Pro Tyr Glu Ser Gly Leu Ser Gly Glu Gly
145                 150                 155                 160

Leu Val Pro Gly Lys Ser Leu Leu Ile Phe Ala Thr Pro Glu Lys Lys
                165                 170                 175

Gly Lys Arg Phe His Ile Asn Leu Leu Lys Lys Asn Gly Asp Ile Ala
            180                 185                 190

Leu His Phe Asn Pro Arg Phe Asp Glu Lys Ala Ile Val Arg Asn Ser
        195                 200                 205

Leu Ile Ala Gly Glu Trp Gly Asn Glu Glu Arg Glu Gly Lys Met Ile
    210                 215                 220

Leu Glu Lys Gly Ile Gly Phe Asp Leu Glu Ile Lys Asn Glu Glu Tyr
225                 230                 235                 240
```

Ala Phe Gln Ile Phe Ile Asn Gly Glu Arg Tyr Ala Thr Tyr Ala His
245 250 255

Arg Leu Asp Pro Arg Glu Ile Asn Gly Leu Gln Ile Gly Gly Asp Leu
260 265 270

Glu Val Ser Gly Ile Gln Met Arg
275 280

<210> SEQ ID NO 12
<211> LENGTH: 141
<212> TYPE: PRT
<213> ORGANISM: Onchocerca volvulus

<400> SEQUENCE: 12

Asp Leu Leu Ser Glu Ala Gly Asp Phe Phe Thr Lys His Phe Thr Asp
1 5 10 15

Ile Lys Ser Leu Phe Ala Lys Asp Glu Lys Gln Leu Gln Gln Ser Val
20 25 30

Asp Arg Val Lys Asp Leu Leu Ala Thr Ile Gln Asp Lys Met Ser Met
35 40 45

Leu Gln Pro Leu Ala Asn Asp Met Gln Lys Thr Thr Leu Gly Lys Ile
50 55 60

Gly Asp Leu Ile Ser Gln Val Asn Ser Phe Arg Glu Thr Met Ser Asn
65 70 75 80

Pro Lys Met Asp Phe Thr Asn Lys Glu Asn Lys Trp Glu Glu Leu Leu
85 90 95

Lys Lys Ile Phe Val Thr Glu Gly Leu Asn Lys Val Ile Pro Leu Leu
100 105 110

Gln Lys Leu Lys Asn Ser Ala Pro Thr Thr Phe Ala Thr Tyr Leu Phe
115 120 125

Thr Cys Ile Val Pro Val Leu Ile Asn Thr Leu Arg Glu
130 135 140

<210> SEQ ID NO 13
<211> LENGTH: 114
<212> TYPE: PRT
<213> ORGANISM: Onchocerca volvulus

<400> SEQUENCE: 13

Met Ala Arg Ile Asn Arg Leu Asn Phe Leu Leu Cys Ile Val His Ala
1 5 10 15

Asn Ile Thr Ser Ala Pro Asn Pro Lys Asp Ser Asn Asp Glu Leu Phe
20 25 30

Ala Asp Ala Glu Ser Ala Leu Gly Ser Glu Tyr Ala Gln Phe Val Glu
35 40 45

Gln Ser Lys Gln His Lys Pro Val Tyr Phe Ser Asp Asn Gln Asn Thr
50 55 60

Leu Glu Thr Ile Lys Leu Glu Ser Ile Pro Asn Pro Glu Thr Glu Thr
65 70 75 80

Ala Tyr Pro Met Phe Ile Cys Gly Phe Leu Gly Cys Met Lys Lys Met
85 90 95

Asn Ser Val Glu Glu Tyr Leu Glu His Phe Lys Met His Glu Lys Gln
100 105 110

Gly Tyr

<210> SEQ ID NO 14
<211> LENGTH: 69

-continued

<212> TYPE: PRT
<213> ORGANISM: Onchocerca volvulus

<400> SEQUENCE: 14

```
Phe Ser Trp Lys Phe Gly Glu Arg Leu Asp Glu Pro Val Leu Met Leu
1               5                   10                  15

Arg Asp Leu Arg Ala Lys Glu Ile Ser Pro Pro Ser Tyr Met Lys Arg
            20                  25                  30

Phe Glu Ser Asp Thr Asn Glu Gln Leu Leu Arg Tyr Ile Leu His Pro
        35                  40                  45

Lys Met Leu Arg Arg His Asp Leu Ser Asn Ala Leu Phe Tyr Gln Pro
    50                  55                  60

Leu Trp Lys Met Arg
65
```

<210> SEQ ID NO 15
<211> LENGTH: 278
<212> TYPE: PRT
<213> ORGANISM: Onchocerca volvulus

<400> SEQUENCE: 15

```
Met Glu Gly Ser Pro Ile Lys Glu Thr Arg Gly Leu Glu Ala Thr Pro
1               5                   10                  15

Val Phe Glu Met Val Arg Ser Ala Thr Leu Thr Phe Leu Leu Ala Val
            20                  25                  30

Ser Thr Val Leu Val Val Ser Arg Pro Asn Val Leu Leu Pro Pro Lys
        35                  40                  45

Leu Pro Trp Asp Ser Asp Trp Arg Gln Lys Pro Pro Pro Phe Pro Pro
    50                  55                  60

Glu Pro Pro Pro Glu Phe Lys Gly Ile Leu Pro Pro Glu Ile Phe Ala
65                  70                  75                  80

Lys Leu Thr Ala Ile His Gln Asp Gln Ser Leu Thr Ile Pro Gln Lys
                85                  90                  95

Ile Val Lys Ile Glu Glu Ile Met Asn Ser Leu Pro Glu Asp Val Leu
            100                 105                 110

Gln Arg Leu Pro Leu Pro Pro Val Phe Arg Leu Leu Pro Gln Asn Val
        115                 120                 125

Gln Glu Met Ile Lys Thr Val Arg Thr Thr Lys Asn Leu Thr Met Glu
    130                 135                 140

Glu Lys Trp Leu Gln Met Ile Ile Leu Ile Glu Ser Leu Pro Lys Gln
145                 150                 155                 160

Gln His Arg Leu Leu Gln Gln Met Leu Pro Lys Phe Ser Leu Gly Pro
                165                 170                 175

Leu Pro Asp Phe Gln Asp Ile Ile Pro Lys Glu Asp Trp Asp Lys Leu
            180                 185                 190

Thr Ala Val Tyr Gln Asp Thr Asn Leu Asp Asn Ile Glu Lys Leu Arg
        195                 200                 205

Arg Val Asp Glu Ile Ile Asp Ala Leu Pro Asp Ser Ile Arg Gln Lys
    210                 215                 220

Ile Pro Leu Ser Pro Pro Phe Gln Lys Leu Pro Asp His Ile Gln Gln
225                 230                 235                 240

Gln Leu Gln Ile Ile His Thr Glu Arg Gly Leu Thr Thr Glu Gln Arg
                245                 250                 255

Phe Arg Lys Met Lys Ala Ile Ile Glu Ser Leu Pro Trp Asp Met Lys
            260                 265                 270
```

```
Lys Leu Met Phe Gln Pro
        275

<210> SEQ ID NO 16
<211> LENGTH: 425
<212> TYPE: PRT
<213> ORGANISM: Onchocerca volvulus

<400> SEQUENCE: 16

Leu Ile Lys Val Phe Pro Glu Ile Ser Ala Asn Met Ser Val Met Phe
1               5                   10                  15

Ala Asn Ser Arg Ser Asn Gln Ala Asn Asn Gly Tyr Leu Val Glu Phe
            20                  25                  30

Lys Ala Gly Arg Ser Asn Leu Gln Ala Gly Ser Thr Val Asp Arg Arg
        35                  40                  45

Lys Val Val Ala Asp Lys Thr Lys Gly Leu Val Phe Ile Lys Gln Ser
    50                  55                  60

Ser Asp Gln Leu Met His Phe Cys Trp Lys Asn Arg Glu Thr Gly Ala
65                  70                  75                  80

Val Val Asp Asp Leu Ile Ile Phe Pro Gly Asp Thr Glu Phe Leu Arg
                85                  90                  95

Val Arg Glu Cys Thr Asp Gly Arg Val Tyr Met Leu Lys Phe Lys Ser
            100                 105                 110

Thr Asp Glu Lys Arg Leu Phe Trp Met Gln Gly Lys Thr Asp Lys
        115                 120                 125

Asp Asp Glu Asn Cys Lys Lys Val Asn Glu Thr Leu Asn Asn Pro Pro
    130                 135                 140

Ala Pro Arg Ala Ala Arg Gly Gly Ala Asp Arg Ala Asp Val Ser
145                 150                 155                 160

Ser Phe Gly Thr Leu Ala Ala Leu Gly Ser Ala Gly Ala Glu Ser Glu
                165                 170                 175

Leu Gly Ala Leu Gly Asn Leu Asp Gln Ser Gln Leu Met Gln Leu Leu
            180                 185                 190

Ser Leu Met Asn His Thr Asn Ser Thr Ser Ala Ser Glu Ala Thr Asn
        195                 200                 205

Leu Leu Pro Gln Leu Pro Leu Val Ala Asp Thr Ser His Pro Met Thr
    210                 215                 220

Ser Glu Asp Ser Gly Thr Thr Ser Thr His Gly Ala Thr Pro Ser Asn
225                 230                 235                 240

Thr Pro Ala Asn Gly Ile Val Ala Asp Ser Ser Ser Asn Asn Ala Met
                245                 250                 255

Gln Leu Ser Gln Leu Lys Glu Ile Ile Ala Ser Ile Thr Pro Pro Asp
            260                 265                 270

Gly Ser Gly Arg Lys Pro Ser Ile Asp Phe Thr Asp Val Leu Cys Cys
        275                 280                 285

Ala Asp Lys Ile Asn Asp Val Leu Arg Lys Tyr Ala Glu Gln Leu Ile
    290                 295                 300

Pro His Leu Pro Ser Gln Glu Pro Ile Tyr Asn Asn Gln Glu Glu Leu
305                 310                 315                 320

Gln Gln Thr Leu Arg Thr Pro Gln Phe Arg Gln Ala Ala Asp Ile Phe
                325                 330                 335

Gly His Ala Leu Gln Thr Gly Gln Leu Ala Pro Val Leu Arg Gln Phe
            340                 345                 350

Gly Ile Asp Gly Asn Thr Ala Thr Ala Ala Gly Asn Gly Asp Met Val
        355                 360                 365
```

-continued

Ala Trp Ala Ala Gln Phe Thr Thr Ala Glu Asn Gly Lys Glu Ile Thr
370 375 380

Ala Lys Thr Glu Thr Ser Pro Ser Gln Pro Gly Met Glu Ser Asp Val
385 390 395 400

Glu Asp Glu Glu Thr Asn Glu Lys Ala Ile Arg Glu Thr Glu Lys Asn
405 410 415

Arg Thr Asp Asp His Met Asp Leu Asp
420 425

<210> SEQ ID NO 17
<211> LENGTH: 90
<212> TYPE: PRT
<213> ORGANISM: Onchocerca volvulus

<400> SEQUENCE: 17

Met Asn Tyr Lys Ala Pro Ile Glu Leu Gln Gln Leu Leu Ser Ile Thr
1 5 10 15

Lys Met Leu Ser Leu Ser Val Leu Leu Leu Phe Thr Ser Met Ala Ile
20 25 30

Met Ala Arg Pro Pro Asn Ser Asp Glu Ile Lys Glu Leu Arg Gln Gln
35 40 45

Gln Leu Asn Glu Ser Lys Asp Asp Tyr Asp Thr Leu Pro Asp Val Asn
50 55 60

His Ile Pro Glu Ser Phe Lys Glu Ser Leu Lys Lys Gln Lys Met Leu
65 70 75 80

Tyr Leu Asp Met Leu Arg Gln His Asn Leu
85 90

<210> SEQ ID NO 18
<211> LENGTH: 257
<212> TYPE: PRT
<213> ORGANISM: Onchocerca volvulus

<400> SEQUENCE: 18

Leu Ser Val Pro Ala Gly Leu Arg Pro Ala Lys Lys Val Gly Asp Pro
1 5 10 15

Lys Glu Gln Ile Val Pro Gly Lys Gln Gln Gln Leu Gln Gln Gln Gln
20 25 30

Gln Gln Gln Leu Leu Gln Gln Gln Gln Gln Gln Gln Gln Gln Gln Gln
35 40 45

Gln Gln Gln Gln Gln Gln Gln Gln Gln Gln Gln Gln Gln Gln Gln Gln
50 55 60

Gln Gln Gln Glu Gln Gln Glu Glu Leu Gln Gln Leu Gln Glu Ser Glu
65 70 75 80

Glu Thr Gly Glu Glu His Arg Gln Gln Gln Gln Gln Gln His Asp Glu
85 90 95

Ala Leu Thr Leu Ser Pro Thr Pro Lys Val Pro Pro Asn Leu Ser Ile
100 105 110

Arg Ser Arg Met Met Ala Ala Leu Ser Ala Ser Val Gly Glu Ser Asn
115 120 125

Lys Glu Lys Asn Ser Ser Asn Asp Glu Thr Asp Asn Ser Ser Lys Ser
130 135 140

Thr Asn Ser Pro Ser Lys Pro Pro Ile Ile Phe Pro Lys Ala Asn Lys
145 150 155 160

Lys Thr Val Val Gly Lys Ile Ala Pro Ser Gly Ile Ser Lys Gly Ser
165 170 175

```
Ala Arg Val Ile Val Ala Pro Pro Ser Lys Leu Gly Thr Asn Asn Phe
            180                 185                 190

Gly Leu Asn Thr Val Leu Gln Thr Asn Leu Val Asp Ser Arg Gly Arg
            195                 200                 205

Ile Met Lys Asn Val Asn Ser Val Pro Ile Lys Val Pro Ser Ser Ala
            210                 215                 220

Glu Met Arg Asn Ala Arg Thr Arg His Thr Ala Arg Gln Val Glu Ser
225                 230                 235                 240

Asp Ala Asp Lys Val Val Pro Ile Lys Phe Gly Ser Thr Ser Arg Arg
                245                 250                 255

Arg
```

<210> SEQ ID NO 19
<211> LENGTH: 130
<212> TYPE: PRT
<213> ORGANISM: Onchocerca volvulus

<400> SEQUENCE: 19

```
Asn Asn Ser Asn Leu Asp Ile Ser Met Arg Glu Lys Asn Ala Val Asn
1               5                   10                  15

Ala Ile Glu Lys Gln Asp Leu Pro Arg Ser His Arg Phe Lys Arg Gln
            20                  25                  30

Tyr Ser Cys Gly Gln Cys Gly Gly Gly Pro Val Val Val
            35                  40                  45

Ser Pro Cys Gln Gln Cys Lys Gly Gly Ala Gly Val Ser Ala Ile
        50                  55                  60

Gly Gly Ala Gly Gly Ile Ser Ala Ile Gly Gly Val Ser Ala Ile
65                  70                  75                  80

Gly Gly Gly Phe Gly Gly Gly Gly Asp Thr Val Ala Val Val Cys
                85                  90                  95

Cys Gly Ala Thr Gly Leu Lys Gly Met Phe Arg Asn Trp Trp Leu His
            100                 105                 110

Ile Pro Leu Leu Leu Leu Pro Met Ser Met Ser Trp Ile Lys Ala Leu
        115                 120                 125

Phe Leu
    130
```

<210> SEQ ID NO 20
<211> LENGTH: 185
<212> TYPE: PRT
<213> ORGANISM: Onchocerca volvulus

<400> SEQUENCE: 20

```
Tyr Tyr Val Pro Asp Asn Tyr Trp Pro Leu Arg Ile Ile Gly Tyr His
1               5                   10                  15

His Ile Pro Val Met Ile Asn Met Trp Tyr Leu Phe Gln Thr Glu Ile
            20                  25                  30

Ser Asn Ile Gly Val Asp Ala Val Leu Val Gln Ser Pro Leu Tyr Arg
            35                  40                  45

Thr Leu Thr Pro Asp Val Val His Asp Ile Ser Ile Asn Val Glu
        50                  55                  60

Pro Asn His Thr Val Val Val Glu Gln Ser Asn Pro Met Leu Gln Ala
65                  70                  75                  80

Ser Ser Val Glu Gln Ala Pro Ala Ala Pro Leu Ser Ile Thr Leu
                85                  90                  95
```

-continued

```
Ile Ala Pro Gly Ile Thr Ile Ser Arg Thr His Lys Val Asp Thr Tyr
            100                 105                 110

Lys Ser Thr Met Glu Met Tyr Asp Ala Asp Lys Leu His Ser Asn Glu
        115                 120                 125

Ile Phe Lys Arg Arg Val Arg Lys Met Val Leu Pro Pro Ser Arg Gly
    130                 135                 140

Glu Glu Val Arg Lys Pro Pro Ser Ser Thr Asp Gly Tyr Glu Ser Glu
145                 150                 155                 160

Asn Val Glu Ser Tyr Gly Gln Lys Gly Val Glu Gln Ala Pro Pro Glu
                165                 170                 175

Ile Glu Gln Tyr Val Lys Lys Lys Lys
            180                 185

<210> SEQ ID NO 21
<211> LENGTH: 633
<212> TYPE: PRT
<213> ORGANISM: Onchocerca volvulus

<400> SEQUENCE: 21

Met Lys Tyr Cys Leu Ser Ser Ile Ile Ala Ala Thr Ile Ala Thr Thr
1               5                   10                  15

Thr Thr Thr Ala Thr Ala Ile Ile Ala Thr Thr Ile Thr Ala Ala Thr
            20                  25                  30

Ile Ser Val Ala Pro Phe His Ala Ser Ser Pro Ser Ser Ser Leu Ser
        35                  40                  45

Ser Ser Ser Phe Ser Ser Phe Phe Leu Val Leu Pro Leu Ile Thr Thr
    50                  55                  60

Ile Leu Leu Ile Val Pro Glu Gln Ala His Ser Thr Ala Thr Val Thr
65                  70                  75                  80

Glu His Arg Ser Pro Pro Asp Leu Ser Ile Pro Ser Gln Thr Glu Phe
                85                  90                  95

Arg Val Pro Val Gly Thr Lys Gln Phe Arg Leu Ile Cys Pro Val Lys
            100                 105                 110

Glu Lys Asn Asp Asp Leu Leu Met Ile Gln Trp Lys Lys Asn Asp Glu
        115                 120                 125

Pro Ile Gly Phe Asp Phe Asn Asn Arg Phe Lys Leu Ala Arg Ser Asp
    130                 135                 140

Arg Glu Leu Lys Ile Arg Asn Pro Gln Leu Ser Asp Gly Gly Ile Tyr
145                 150                 155                 160

Gln Cys Gln Val Val Asn Gly Phe Gly His Arg Glu Leu Asn Phe Thr
                165                 170                 175

Val Thr Phe Tyr Asp Pro Ala Met Glu Asn Asp Gln Asn Thr Asp Ser
            180                 185                 190

Thr Leu Thr Leu Thr Thr Lys Ala Ser Pro Pro Ile Trp Lys Asn Glu
        195                 200                 205

Thr Glu Ile Arg Asn Trp Met Ile Asn Pro Val Arg Ile Thr Ile Gly
    210                 215                 220

Gly Ala Leu Leu Leu Lys Cys Pro Ala Lys Gly Asn Pro Leu Pro His
225                 230                 235                 240

Ile Thr Trp Leu Arg Asp Gly Lys Val Leu Glu Arg Glu Ile Thr Tyr
                245                 250                 255

His Tyr Ser Ser Ala Ile Leu Tyr Leu Ser Asp Val Gln Pro Ser Glu
            260                 265                 270

Gly Gly Lys Tyr Ile Cys Lys Leu Glu Asn Glu His Gly Ser Ile Glu
        275                 280                 285
```

```
Ala Ser Phe His Val Tyr Val Glu Asn Phe Phe Gly Leu Asp Gly
    290                 295                 300

Glu Ser Trp Ser Ile Asp Gln Thr Asn Ala Gln Leu Tyr Pro Val Ile
305                 310                 315                 320

Asp Glu Pro Phe Asn Asn Thr Val Arg Val Gly Arg Thr Ala Gln Phe
                325                 330                 335

Gln Cys Lys Val Lys Asn Gln Gln Pro Leu Ile Lys Trp Leu Lys
                340                 345                 350

Arg Val Glu Asp Pro Asn Ala Ile Arg Gln Thr Asn Ala Asn Ala Thr
                355                 360                 365

Leu Ile His Ala Asn Asn Met His Leu Leu Leu Glu Lys Pro Glu
    370                 375                 380

Thr Ser Ala Glu Leu Ser Asp Gly Ile Ser Leu Asn Arg Leu Ile Ile
385                 390                 395                 400

Pro Asn Val Arg Tyr Glu His Ser Gly Thr Tyr Leu Cys Val Val Thr
                405                 410                 415

Asn Ala Arg Gly Asp Ile Ala Tyr Arg Ser Ala Tyr Leu Asn Val Ile
                420                 425                 430

Ala Arg Ser Asp His Gly Glu Leu Ser Asn Leu Tyr Phe Tyr Gly Gly
    435                 440                 445

Leu Leu Val Leu Ile Val Val Phe Thr Leu Ile Thr Tyr Ala Val His
    450                 455                 460

Phe Leu Arg Lys Asn Gln Ala Ala Lys Ser Thr Glu Ser Ala Pro Gly
465                 470                 475                 480

Ile Thr Asn Ile Arg Tyr Ser Phe Ser Leu Arg Pro Pro Pro Asn
                485                 490                 495

Leu Pro Pro Pro Lys Ala Pro Ala Leu Pro Ser Glu Arg Gln Gln Leu
                500                 505                 510

Met Pro Asn Asn Gln Pro Cys Asp Arg Tyr Thr Val Asn Ser Ala Ala
                515                 520                 525

Ala Thr Tyr Tyr Pro Gln Phe Ala Thr Pro Asp Lys Lys Leu Gln Lys
    530                 535                 540

Ile Ile Thr Glu Ser Gly Thr Arg Pro Thr Pro Ile Arg Arg Thr Asn
545                 550                 555                 560

Gly Gly Asp Thr Lys Tyr Arg Leu Lys Asp Asp Tyr Ile Ser Ser Pro
                565                 570                 575

Lys Trp Val His Ala Lys Gly Asp Asn Ile Glu Val Glu Met Asp Gln
                580                 585                 590

Asn Leu Leu Lys Asn Arg Ser Thr His Cys His Asn Pro Val Ser Ile
                595                 600                 605

Ala Tyr Gly Arg Ile Asp Asn Ile Asp Arg Gln Gln Gln Lys Ser Phe
    610                 615                 620

Leu Thr Ile Gly Asn Leu Gln Lys Arg
625                 630

<210> SEQ ID NO 22
<211> LENGTH: 189
<212> TYPE: PRT
<213> ORGANISM: Onchocerca volvulus

<400> SEQUENCE: 22

Lys Glu Ile Ile Trp Asp Cys Tyr Gly Asp Tyr Glu Glu Cys Val Ala
1               5                   10                  15

Glu Ser Ser Lys Met Asp His Val Asp Val Asn Asn Val Glu Ser Arg
```

```
                20                  25                  30
Asn Ile Ile Glu Phe Cys Ser Asp His Thr Gln Asn Ile Leu Pro Cys
             35                  40                  45

Leu Ala Thr Lys Leu Gly Leu Ile Lys Ser Met Ser Val Ser Met Phe
 50                  55                  60

Ser Leu Leu Leu Thr Ile Cys Glu Ala Glu Thr Arg Asn Asn Arg Pro
 65                  70                  75                  80

Ala Ala Thr Glu Val Gln Gln Ile Leu Lys His Leu Ala Arg Leu Tyr
                 85                  90                  95

Ala Tyr Phe Cys Ala Tyr Ser Asn Val Ile Asp Leu Arg Tyr Asn Lys
            100                 105                 110

Glu Cys Phe Arg Tyr Leu Lys Lys Arg Cys Ile Leu Asn Lys Pro Asp
            115                 120                 125

Asp Ser Cys Ile Phe His His Cys Gly Glu Lys Asn Leu Asn Leu Ser
130                 135                 140

Glu Ser Ser Pro Phe Ile Gln Gln His Lys Thr Thr Ile Ile Asn Gln
145                 150                 155                 160

Leu Asn Gln Ser Ala Thr Phe Lys Asn Tyr His His Arg Ile Thr Thr
                165                 170                 175

Ile Phe Thr Val Ile Ile Thr Phe Ile Ser Met Ile Gln
                180                 185

<210> SEQ ID NO 23
<211> LENGTH: 399
<212> TYPE: PRT
<213> ORGANISM: Onchocerca volvulus

<400> SEQUENCE: 23

Met Tyr Asn Gln Glu Asn His Asp Lys Arg Arg Asn Asp Asp Arg Phe
 1               5                  10                  15

Ile Leu Ser Leu Pro Phe Gly Thr Asn Val Glu Asn Lys Ser Tyr Phe
             20                  25                  30

Lys Pro Ile Lys Leu Ser Asn Pro Tyr Ser Asp Lys Tyr Leu Glu Val
             35                  40                  45

Asn Lys Lys Ser Ser Asp Asp Ser Asp Gln Asn Leu Asn Gln Ala Leu
 50                  55                  60

Ser Val Pro Gln Ser Asn Tyr Asp Gln Ser Ser Glu Ser Leu Ser Ile
 65                  70                  75                  80

Asp Asp Ser Asp Leu Ile Asp Asp Ser Thr Ser Ala Ala Gln Leu Ser
                 85                  90                  95

Thr Ser Ser Pro Ile Ser Val Thr Ser Ala Ser Thr Ser Ser Phe Tyr
            100                 105                 110

Pro Thr Leu Asn Ile Gly Asn Gly Met Glu Ile Ser Ala Lys Tyr Ala
            115                 120                 125

Lys Leu Glu Gln Ser Gln Gly Ile Lys Ser Asp Gln Ser Thr Ser Arg
130                 135                 140

Val Ser Asp Arg Tyr Lys Lys Tyr Thr Ala Val Lys Arg Arg Leu Ser
145                 150                 155                 160

Glu Leu Tyr Gly Ile Ile Glu Glu Lys Asp Glu Gln Leu Arg Val Val
                165                 170                 175

Arg Asn Glu Leu Asn Gly Lys Asp Leu Glu Ile Gly Lys Leu Cys Asp
                180                 185                 190

Lys Ile Arg Ala Leu Glu Tyr Asn Cys Gly Arg Leu Gln Ser Met Ile
            195                 200                 205
```

-continued

```
Glu Ser Ala Gly Asp Glu Ser Asp Gln Asn Gln Val Lys Leu His Glu
    210                 215                 220

Ile Ile Asn Glu Arg Asp Gly Leu Leu Ile Arg Asn Ala Ser Leu Ser
225                 230                 235                 240

Arg Gln Ile Glu Phe Glu Lys Arg Glu Trp Ser Ile Glu Arg Glu Arg
                245                 250                 255

Leu Ser Met Asp Leu Asp Asp Val Thr Arg Glu Leu Glu Leu Gln Lys
            260                 265                 270

Met Ile Leu Asn Gly Glu Ser Ile Ser Glu Ile Val Gln Arg Trp Gln
        275                 280                 285

Thr Lys Val Phe Glu Leu Glu Gly Met Ile Thr Asp Arg Asp Arg Ala
    290                 295                 300

Ile Arg Ala Gln Gln Val Gln Ile Ser Lys Leu Lys Glu Ser Ile Ala
305                 310                 315                 320

Glu Thr Asp Arg Ile Ser Cys Ala Asp Ser Ser Glu Ser Gln Thr Lys
                325                 330                 335

Phe Asp Phe Pro Ser Phe Thr Tyr Ile Lys Arg Leu Leu Leu Gln Tyr
            340                 345                 350

Leu Thr Arg Leu Ala Asp Leu His Phe Ser Ser Asp Glu Glu Arg Met
        355                 360                 365

Gln Leu Val Arg Asn Met Ser Ser Ile Leu His Leu Ser Asp Glu Glu
    370                 375                 380

Gln Arg Gln Val Trp Ala Asn Leu Lys Ser Lys Ile Gln Ile Ser
385                 390                 395
```

<210> SEQ ID NO 24
<211> LENGTH: 301
<212> TYPE: PRT
<213> ORGANISM: Onchocerca volvulus

<400> SEQUENCE: 24

```
Gln Cys Pro Thr Gly Ser Val Ser Leu Leu Ser Gly Tyr Arg Cys Thr
1               5                   10                  15

Ser Ser Ile Gln Cys Gln Thr Ile Ile Pro Gly Ser Tyr Cys Tyr Tyr
            20                  25                  30

Gly Val Cys Cys Thr Gly Gly Ser Asp Val Leu Ser Lys Thr Val Ser
        35                  40                  45

Tyr Gly Gly Tyr Cys Thr Met Thr Val Gln Cys Ser Thr Thr Gly Ala
    50                  55                  60

Thr Cys Ile Ser Asn Ile Cys Gln Cys Asp Ile Asn Ser His Tyr Asn
65                  70                  75                  80

Gly His Ser Cys Val Ser Ile Ser Asn Phe Cys Pro Ser Asn Gln Val
                85                  90                  95

Phe Ile Lys Gly Glu Cys Tyr Arg Lys Val Thr Tyr Gly Phe Leu Cys
            100                 105                 110

Asn Tyr Thr Gln Gln Cys Gly Tyr Ile Gly Ala Phe Cys Ile Gly Asn
        115                 120                 125

Ile Cys Ser Cys Gln Leu Asp Tyr Thr Phe Asp Gly Ser Lys Cys Ile
    130                 135                 140

Pro Arg Ser Arg Ile Cys Pro Ala Asn Gln Ile Ala Ile Gly Gly Gln
145                 150                 155                 160

Cys Tyr Pro Ser Ala Arg Phe Gly Glu Arg Cys Leu Tyr Ser Glu Gln
                165                 170                 175

Cys Ile Asp Arg Trp Tyr Arg Ser Leu Ser Cys Val Asn Gly Phe Cys
            180                 185                 190
```

```
Asn Ile Arg Asn Asp Asp Asp Ile Ser Lys Pro Lys Cys Arg Asn Pro
        195                 200                 205

Arg Ala Glu Val Glu Tyr Val Asn Gly Thr Ala Lys Asn Cys Leu Tyr
    210                 215                 220

Trp Pro Cys Thr Val Gly Tyr Phe Cys Glu Tyr Ala Gly Gly Met Asn
225                 230                 235                 240

Gly Gly Arg Tyr Ile Cys Cys Gly Thr Asn Ala Asn Lys Ile Tyr Gly
                245                 250                 255

Lys Val Gln Leu Tyr Pro Gly Thr Gly Thr Pro Leu Gln Cys Thr Glu
            260                 265                 270

Ile Gly Arg Cys Pro Phe Pro Asp Thr Pro Asn Cys Val Met Ser Tyr
        275                 280                 285

Arg Tyr Gly Tyr Lys Val Cys Cys Ser Thr Leu Asn Cys
    290                 295                 300

<210> SEQ ID NO 25
<211> LENGTH: 110
<212> TYPE: PRT
<213> ORGANISM: Onchocerca volvulus

<400> SEQUENCE: 25

Gln Glu Thr Ser Glu Gln Pro Gly Leu Thr Val Glu Ile Ile Ala Glu
1               5                   10                  15

Gln Gln Asp Ala Thr Thr Ala Asp Gln Glu Val Thr Thr Thr Val Asp
            20                  25                  30

Thr His His Gln His Gln His Gln Thr Asp Lys Val Val Lys Ser Arg
        35                  40                  45

Gln Ile Thr Gly Asp Glu Gln Thr Thr Thr Thr Thr Thr Ala Ile Asn
    50                  55                  60

Leu Asn Glu Thr Ile Thr Asn Ser Thr Thr Asp Ser Asn Ser Thr Ile
65                  70                  75                  80

Ile Thr Thr Thr Leu Asp Leu Gln Glu Ser Thr Thr Thr Gly Thr Thr
                85                  90                  95

Asp Asn His His His His His His His His His His His Glu
            100                 105                 110

<210> SEQ ID NO 26
<211> LENGTH: 185
<212> TYPE: PRT
<213> ORGANISM: Onchocerca volvulus

<400> SEQUENCE: 26

Met Lys Gln Thr Thr Ala Trp Gly Asn Ala Leu Cys Val Leu Cys Asn
1               5                   10                  15

Cys His Gln Pro Gln Ile Ile Cys Pro Pro Pro Pro Pro Ala Val Cys
            20                  25                  30

Pro Arg Val Val Cys Pro Pro Pro Arg Pro Pro Val Cys Pro Pro Ile
        35                  40                  45

Tyr Cys Pro Pro Pro Val Val Cys Pro Pro Pro Pro Val Cys Pro Pro
    50                  55                  60

Val Pro Phe Cys His Ser Gln Ile Cys Pro Pro Cys Gly Thr His Thr
65                  70                  75                  80

Val Pro Val Ala Val Val Gly Cys Cys Lys Gly Cys Ala Cys Ser Val
                85                  90                  95

Arg Phe Lys Arg Asp Ser Ser Ser Val Asn Gly Leu Met Leu Lys Lys
            100                 105                 110
```

Asn Leu Leu Cys Asn Asn Asp Gln Leu Met Thr Ile Met Glu Lys Lys
            115                 120                 125

Ile Gly Thr Asn Ala Thr Glu Ala Ala Phe Ala Ile Lys Lys Glu Ala
        130                 135                 140

Asp Ser Glu Leu Lys Ala Lys Phe Ser Val Phe Cys Ala Met Asn Asp
145                 150                 155                 160

Leu Ile Tyr Val Ala His Ala Glu Ser Phe Cys Gln His Lys Lys Gly
                165                 170                 175

Asp Ile Ile Cys Phe Ala Tyr Lys Ser
                180                 185

<210> SEQ ID NO 27
<211> LENGTH: 147
<212> TYPE: PRT
<213> ORGANISM: Onchocerca volvulus

<400> SEQUENCE: 27

Met Asp Cys Lys Leu Ile Leu Pro Phe Tyr Ile Leu Leu Ala Asn Leu
1               5                   10                  15

Glu Ala Asn Ala Phe His Leu Ser Gly Tyr Arg Ser Arg Ser Tyr Leu
            20                  25                  30

Gln Gly Ile Gln Pro Tyr Asp Ile Gln Pro Leu Asp Val Gln Pro Gln
        35                  40                  45

Phe Ile Arg Val Gln Thr Leu Lys Ser Gln Asp Ile Gln Pro Tyr Ser
    50                  55                  60

Ile Gln Ser Arg Ser Glu Asp Gln Pro Cys Glu Gly Cys Lys Ile Thr
65                  70                  75                  80

Ile Ser Cys Gly Ser Lys Asn Cys Lys Ser Lys Leu Pro Tyr Val
                85                  90                  95

Tyr Lys Pro Ile Phe Lys Leu Leu Ser Thr Arg Ser Thr Lys Lys Pro
                100                 105                 110

Val Phe Thr Leu Pro Thr Gln Pro Pro Ala Gln Trp Asp Cys Pro Cys
            115                 120                 125

Pro Cys His Val Pro Gln Arg Cys Arg Met Cys Ser Ala Cys His Glu
        130                 135                 140

Ser Tyr Ile
145

<210> SEQ ID NO 28
<211> LENGTH: 194
<212> TYPE: PRT
<213> ORGANISM: Onchocerca volvulus

<400> SEQUENCE: 28

Asn Arg Ile Ile Ser Arg Arg Leu Ser Leu Phe Ile Gln Gln Tyr Cys
1               5                   10                  15

Cys Asn Asn Ile Ser Gln Ile Tyr Arg Leu Asn Asp Cys Lys Tyr Ser
            20                  25                  30

Lys Val Lys Met Glu Ile Asp Lys Lys Ile Phe Ile Ile Val Ser Lys
        35                  40                  45

Thr Glu Trp Cys Asn Glu Ala Ile Lys Val Val Phe Gly Lys Ser Ala
    50                  55                  60

Glu Ala Ile Arg Asn Asn Ser Asp Ala Ile Ser Trp Leu Ala Ser Tyr
65                  70                  75                  80

Asn Tyr Thr Gly Ser Met Asp Leu Arg Ser Lys Trp Pro Tyr Asp Ala
                85                  90                  95

```
Tyr Phe Asp Asn Val Thr Arg Thr Ala His Gly Leu Ala Arg Ile Asp
            100                 105                 110

Leu Leu Cys His Lys Lys Arg Pro Gln Leu Gly Pro Arg Ile Trp Lys
        115                 120                 125

Arg Ser Val Gln Lys Ile Lys Gln Lys Lys Asp Arg Pro Phe Ala Val
    130                 135                 140

Asn Thr Tyr Gly Asn Asn Lys Gly Leu Phe Thr Ile Thr Val Gly Val
145                 150                 155                 160

Leu Leu Tyr Ala Ala Phe Gly Thr Cys Phe Leu Ile Ala Asn Leu Ala
                165                 170                 175

Tyr Leu Phe Gly Ile Tyr Ile Ile Tyr Asp Ala Ser Ile Ile Asp Glu
            180                 185                 190

Val Ser

<210> SEQ ID NO 29
<211> LENGTH: 263
<212> TYPE: PRT
<213> ORGANISM: Onchocerca volvulus

<400> SEQUENCE: 29

Ile Gly Glu Asn Pro Met Asp Val Asn Ala Ile Ala Gly Ile Ile Gly
1               5                   10                  15

Gly Ile Ser Asn Met Met Gln Asn Asn Val Glu Thr Ile Asp Val Pro
            20                  25                  30

Ser Ser Gln Ile Met Gly Arg Trp Tyr Gln Val Tyr Lys Ala Ala Ile
        35                  40                  45

Ala Phe Asp Val Tyr Arg Thr Asp Ile Phe Cys Pro Val Ala Tyr Phe
    50                  55                  60

Lys Pro Asn Ser Val Met Gly Glu Asp Gly Phe Ser Ile Glu Glu Ala
65                  70                  75                  80

Tyr Arg Val Ile Thr Lys Asn Gly Pro Val Glu Thr Tyr Lys Arg Asp
                85                  90                  95

Leu Asn Lys Val Gly Thr Gly Gln Tyr Trp Met Tyr Thr Glu Glu Tyr
            100                 105                 110

Phe Tyr Pro Arg Gln Phe Asn Ile Ile Ser Val Gly Pro Asn Tyr Thr
        115                 120                 125

Asn Thr Thr Asp Gly Ser Glu Glu Glu Lys Gln Tyr Gln Tyr Met Val
    130                 135                 140

Val Thr Asp Gly Asn Arg Leu Ser Leu Ser Val Tyr Ala Arg His Pro
145                 150                 155                 160

Met Ile Phe Tyr Gln Lys Tyr Asn Glu Glu Val Val Lys Phe Leu Glu
                165                 170                 175

His Ala Gly Phe Gly Gly Lys Val Phe Trp Asn Ser Pro Lys Pro Ile
            180                 185                 190

Tyr Gln Gly Ala Asp Cys Glu Trp Pro Ser Glu Lys Glu Val Phe Ala
        195                 200                 205

Arg Arg Val Leu Lys Asn Gln Glu Leu Ala Lys Asn Gly Gly Leu Asp
    210                 215                 220

Thr Ala Thr Lys Ser Gly Ser Phe Gly Gly Ser Ser Gln Ala Thr Asp
225                 230                 235                 240

Val Arg Ser Ser Ile Thr Glu Ile Leu Gln Asn Pro Gln Leu Ala Leu
                245                 250                 255

Gln Lys Leu Val Gln Gly His
            260
```

<210> SEQ ID NO 30
<211> LENGTH: 242
<212> TYPE: PRT
<213> ORGANISM: Onchocerca volvulus

<400> SEQUENCE: 30

Met Thr Ile Ile Lys Ser Met Leu Lys Ile Thr His Val Ile Phe Asp
1               5                   10                  15

Leu Asp Gly Leu Leu Ile Asp Thr Glu Val Val Phe Ser Lys Val Asn
            20                  25                  30

Gln Cys Leu Leu Ser Lys Tyr Asp Lys Lys Phe Thr Pro His Leu Arg
        35                  40                  45

Gly Leu Val Thr Gly Met Pro Lys Lys Ala Ala Val Thr Tyr Met Leu
    50                  55                  60

Glu His Glu Lys Leu Ser Gly Lys Val Asp Val Asp Glu Tyr Cys Lys
65                  70                  75                  80

Lys Tyr Asp Glu Met Ala Glu Glu Met Leu Pro Lys Cys Ser Leu Met
                85                  90                  95

Pro Gly Val Met Lys Leu Val Arg His Leu Lys Thr His Arg Ile Pro
            100                 105                 110

Met Ala Ile Cys Thr Gly Ala Thr Lys Lys Glu Phe Glu Ile Lys Thr
        115                 120                 125

Arg His His Lys Glu Leu Leu Asp Leu Ile Ser Leu Trp Val Leu Ser
    130                 135                 140

Gly Asp Asp Pro Ala Ile Lys Arg Gly Lys Pro Ala Pro Asp Pro Phe
145                 150                 155                 160

Leu Val Thr Met Asp Arg Phe Lys Gln Lys Pro Glu Lys Ala Glu Asn
                165                 170                 175

Val Leu Val Phe Glu Asp Ala Thr Asn Gly Val Cys Ala Ala Ile Ala
            180                 185                 190

Ala Gly Met Asn Val Val Met Val Pro Asp Leu Thr Tyr Met Lys Ile
        195                 200                 205

Pro Glu Gly Leu Glu Asn Lys Ile Asn Ser Val Leu Lys Ser Leu Glu
    210                 215                 220

Asp Phe Lys Pro Glu Ser Val Gly Leu Pro Ala Tyr Asp Ala Ser Ser
225                 230                 235                 240

Asn Glu

<210> SEQ ID NO 31
<211> LENGTH: 148
<212> TYPE: PRT
<213> ORGANISM: Onchocerca volvulus

<400> SEQUENCE: 31

Ile Pro Gln Arg Arg Gln Gln Gln Gln Gln Gln Gln Gln Gln Gln Gln
1               5                   10                  15

Arg Asp Glu Arg Glu Ile Pro Pro Phe Leu Glu Gly Ala Pro Pro Ser
20 25 30

Val Ile Asp Glu Phe Tyr Asn Leu Leu Lys Thr Asp Glu Asn Lys Thr
35 40 45

Asp Gln Gln Thr Glu Ala Asp Val Glu Ala Phe Ile Asn Arg Leu Gly
50 55 60

Gly Ser Tyr Lys Val Arg Phe Thr Gln Phe Met Glu Glu Val Lys Lys
65 70 75 80

-continued

```
Ala Arg Ala Asp Tyr Glu Arg Ile His Gln Gln Ala Val Ala Arg Phe
                85                  90                  95

Ser Pro Ala Ala Lys Asp Ala Asp Ala Arg Met Ser Ala Ile Ala Asp
            100                 105                 110

Ser Pro His Leu Thr Thr Arg Gln Lys Ser Gln Gln Ile Gln Ala Ile
        115                 120                 125

Met Asp Ser Leu Ser Glu Ser Val Arg Arg Glu Ile Ile Asn Ala Leu
    130                 135                 140

Ser Pro Gln Glu
145

<210> SEQ ID NO 32
<211> LENGTH: 141
<212> TYPE: PRT
<213> ORGANISM: Onchocerca volvulus

<400> SEQUENCE: 32

Asp Leu Leu Ser Glu Ala Gly Asp Phe Phe Thr Lys His Phe Thr Asp
1               5                   10                  15

Ile Lys Ser Leu Phe Ala Lys Asp Glu Lys Gln Leu Gln Gln Ser Val
            20                  25                  30

Asp Arg Val Lys Asp Leu Leu Ala Thr Ile Gln Asp Lys Met Ser Met
        35                  40                  45

Leu Gln Pro Leu Ala Asn Asp Met Gln Lys Thr Thr Leu Gly Lys Ile
    50                  55                  60

Gly Asp Leu Ile Ser Gln Val Asn Ser Phe Arg Glu Thr Met Ser Asn
65                  70                  75                  80

Pro Lys Met Asp Phe Thr Asn Lys Glu Asn Lys Trp Glu Glu Leu Leu
                85                  90                  95

Lys Lys Ile Phe Val Thr Glu Gly Leu Asn Lys Val Ile Pro Leu Leu
            100                 105                 110

Gln Lys Leu Lys Asn Ser Ala Pro Thr Thr Phe Ala Thr Tyr Leu Phe
        115                 120                 125

Thr Cys Ile Val Pro Val Leu Ile Asn Thr Leu Arg Glu
    130                 135                 140

<210> SEQ ID NO 33
<211> LENGTH: 446
<212> TYPE: PRT
<213> ORGANISM: Dirofilaria immitis

<400> SEQUENCE: 33

Met Arg Thr Ala Ser Gln Leu Thr Phe Met Leu Phe Leu Val Leu Lys
1               5                   10                  15

Lys Lys Phe Lys Asn Ile Asp Lys Leu Phe Ser Gln Ile Ser Val Asn
            20                  25                  30

Met Ser Val Met Phe Ala Asn Ser Arg Ser Gln Ala Asn Ser Gly
        35                  40                  45

Tyr Leu Val Glu Phe Lys Ala Gly Arg Ser Asn Leu Gln Ala Gly Ser
    50                  55                  60

Thr Val Asp Lys Arg Lys Val Val Ala Asp Lys Thr Lys Gly Leu Ile
65                  70                  75                  80

Phe Ile Lys Gln Ser Ser Asp Gln Leu Met His Phe Cys Trp Lys Asn
                85                  90                  95

Arg Glu Thr Gly Thr Val Val Asp Leu Ile Ile Phe Pro Gly Asp
            100                 105                 110
```

```
Thr Glu Phe Leu Arg Val Lys Glu Cys Thr Asp Gly Arg Val Tyr Met
            115                 120                 125

Leu Lys Phe Lys Ser Thr Asp Glu Lys Arg Leu Phe Trp Met Gln Asp
        130                 135                 140

Gly Lys Thr Asp Lys Asp Glu Asn Cys Lys Lys Ile Asn Glu Thr
145                 150                 155                 160

Leu Asn Asn Pro Pro Ala Pro Arg Ala Ala Arg Gly Gly Ala Asp
                165                 170                 175

Arg Ala Gly Ala Ser Ser Phe Gly Thr Leu Ala Ala Leu Gly Ser Ala
                180                 185                 190

Gly Ala Asp Ser Glu Leu Gly Ala Leu Gly Asn Leu Asp Gln Asn Gln
            195                 200                 205

Leu Met Gln Leu Leu Ser Leu Met Asn His Thr Asn Ser Ala Ser Ala
        210                 215                 220

Ser Glu Ala Ala Asn Leu Leu Pro Gln Leu Pro Leu Val Ala Asp Thr
225                 230                 235                 240

Pro Asn Pro Val Ala Ser Glu Glu Ser Gly Thr Thr Ser Thr Gln Gly
                245                 250                 255

Ala Thr Pro Ser Asn Thr Pro Ala Asn Gly Ile Ile Ala Gly Ser Ser
            260                 265                 270

Ser Asn Asn Ala Val Gln Leu Ser Gln Leu Lys Glu Ile Ile Ala Ser
        275                 280                 285

Ile Thr Pro Pro Asp Gly Ser Ile Arg Lys Pro Ser Val Asp Phe Thr
290                 295                 300

Asp Val Leu Cys Cys Ala Asp Lys Ile Asn Asp Val Leu Gly Lys Tyr
305                 310                 315                 320

Ala Glu Arg Leu Ile Pro His Leu Pro Asn Gln Glu Pro Ile Tyr Asn
                325                 330                 335

Asn Gln Glu Glu Leu Gln Gln Thr Leu Arg Thr Pro Gln Phe Arg Gln
            340                 345                 350

Ala Val Asp Ile Phe Gly His Ala Leu Gln Thr Gly Gln Leu Ala Pro
        355                 360                 365

Ile Leu Arg Gln Phe Gly Ile Asp Ser Asn Thr Ala Ile Ala Ala Gly
370                 375                 380

Asn Gly Asp Leu Ile Ala Trp Ala Thr Gln Phe Thr Ser Glu Asn
385                 390                 395                 400

Glu Lys Glu Ile Ala Val Lys Thr Glu Thr Leu Pro Phe His Pro Gly
                405                 410                 415

Met Glu Ser Asp Val Glu Asp Glu Thr Asn Glu Lys Ala Val Arg
            420                 425                 430

Glu Ser Asp Lys Asn Arg Thr Asp Asp His Met Asp Leu Asp
        435                 440                 445

<210> SEQ ID NO 34
<211> LENGTH: 114
<212> TYPE: PRT
<213> ORGANISM: Dirofilaria immitis

<400> SEQUENCE: 34

Met Leu Pro Thr Leu Tyr Ile Asn Asn Ala Val Ile Arg Pro Val Leu
1               5                   10                  15

Ser Glu Thr Lys Lys Val Lys Val Gln Asn Ile Ser Ser Pro Phe Leu
            20                  25                  30

Ile Phe Leu Leu Leu Ser Ile Thr Lys Met Leu Ser Leu Ser Val Leu
        35                  40                  45
```

Leu Leu Phe Ile Ser Met Ala Thr Met Ala Arg Pro Pro Asn Pro Asp
            50                  55                  60

Glu Ile Lys Glu Leu His Glu Gln Gln Leu Asn Asp Ser Lys Asp Asp
 65                  70                  75                  80

Tyr Asp Met Leu Pro Asp Val Gly His Ile Pro Glu Ser Phe Lys Glu
                85                  90                  95

Ser Leu Lys Lys Gln Lys Met Leu Tyr Leu Asp Met Leu Arg Gln Gln
            100                 105                 110

Ser Leu

<210> SEQ ID NO 35
<211> LENGTH: 298
<212> TYPE: PRT
<213> ORGANISM: Dirofilaria immitis

<400> SEQUENCE: 35

Met Ile Ser Ser Arg Leu Arg Ile Thr Ile Pro Glu Ser Ile Val Ile
 1               5                  10                  15

Phe Gly Ile Phe Cys Phe Phe Ile Phe Phe Cys Phe Leu Ser Phe Phe
                20                  25                  30

Phe Phe Phe Thr Leu Trp Ser His Arg Asp Thr Ile Asn Phe Gln Thr
            35                  40                  45

Asp Phe Met Thr Glu Thr Ile Lys Phe Ile Val Tyr Ala Val Val Ile
 50                  55                  60

Leu Arg Met Met Phe Phe Asp Ile Val Cys Phe Tyr Ser Phe Leu Met
 65                  70                  75                  80

Met Thr Ile Val Leu Ile Asn Thr Ser Asn Gly Leu Ser Val Pro Ala
                85                  90                  95

Gly Leu Arg Pro Ala Lys Lys Val Gly Asp Pro Arg Glu Gln Ile Val
            100                 105                 110

Pro Gly Lys Glu Gln Gln Gln Gln Arg Glu Gln Gln Gln Gln Gln Gln
            115                 120                 125

Gln Gln Leu Gln Glu Glu Glu Gln Gln Gln Gln Gln Gln His Asp Glu
            130                 135                 140

Val Ser Asn Leu Arg Pro Thr Pro Lys Val Pro Pro Asn Leu Ser Ile
145                 150                 155                 160

Arg Ser Arg Met Met Ala Ala Leu Ser Ala Ser Pro Val Glu Pro Asn
                165                 170                 175

Lys Glu Lys Asn Ser Ser Lys Val Glu Thr Asp Ser Phe Ser Lys Pro
            180                 185                 190

Pro Ile Ile Phe Ser Lys Gly Asn Lys Lys Thr Val Pro Gly Lys Ile
            195                 200                 205

Ala Pro Ser Gly Ser Lys Gly Asn Ala Arg Val Ile Val Ala Pro
            210                 215                 220

Pro Ala Asp Leu Gly Lys Asn Asn Tyr Gly Leu Asn Thr Val Leu Gln
225                 230                 235                 240

Thr Asn Leu Val Asp Ser His Gly Arg Ile Met Lys Asn Val Asn Ser
                245                 250                 255

Val Pro Ile Lys Val Pro Ser Ala Glu Met Lys Asn Ala Arg Thr
            260                 265                 270

Arg His Thr Ala Arg Gln Val Glu Ser Asp Ala Asp Lys Val Val Pro
            275                 280                 285

Ile Lys Phe Gly Ser Thr Ser Arg Arg
            290                 295

<210> SEQ ID NO 36
<211> LENGTH: 99
<212> TYPE: PRT
<213> ORGANISM: Dirofilaria immitis

<400> SEQUENCE: 36

Met Met Arg Ile Lys Trp Ile Ile Leu Leu Leu Leu Leu Leu Pro
1               5                   10                  15

Ile Ile Thr Ala Glu Phe Ser Ala Pro Val Gly Thr Asn Ser Ser Leu
            20                  25                  30

Thr Ile Phe Asp Lys Asp Lys Gln Val Leu Leu Arg Ser Asp Arg Leu
                35                  40                  45

Lys Arg Gln Cys Gly Pro Cys Gly Val Ala Pro Ser Pro Val Ile Val
50                  55                  60

Cys Cys Gly Ala Ala Gly Leu Lys Glu Ile Phe Arg Ser Trp Trp Leu
65                  70                  75                  80

His Ile Pro Leu Leu Leu Leu Pro Met Ser Thr Ser Trp Leu Lys Thr
                85                  90                  95

Met Val Cys

<210> SEQ ID NO 37
<211> LENGTH: 193
<212> TYPE: PRT
<213> ORGANISM: Dirofilaria immitis

<400> SEQUENCE: 37

Met Phe Arg Leu Leu Ile Ala Ile Gln Ile Leu Arg Phe Cys Gln Ala
1               5                   10                  15

Asn Tyr Ile Asn Asp Val Tyr Trp Lys Arg Ser Ile Ile Gly Tyr Gln
            20                  25                  30

His Ile Pro Ile Ile Leu Asn Ile Cys Tyr Leu Leu Gln Thr Glu Val
                35                  40                  45

Ser Asn Lys Gly Val Val Asp Ala Leu Phe Leu His Ser Pro Thr Tyr
50                  55                  60

His Arg Val Glu Met Ser Glu Glu Thr Asp Asn Ile Glu Ser Ile Ala
65                  70                  75                  80

Asp Lys Ser Asn Ile Thr Val Ala Asn Lys Pro Asn Leu Met Ile Tyr
                85                  90                  95

Pro Ala Asp Phe Gln Val Ser Ser Asn Glu Arg Ala Ser Ala Ser Ile
            100                 105                 110

Pro Ile Thr Ile Thr Ile Thr Ser Ser Gly Asp Thr Ile Ile Lys Ser
            115                 120                 125

Phe Lys His Lys His Gln Ser Asn Glu Ile Phe Lys Arg Arg Val Ala
        130                 135                 140

Lys Met Ala Ile Ala Pro Val Asn Ala Pro Glu Val Glu Asn Leu Ala
145                 150                 155                 160

Pro Glu Val Glu Asn Pro Ser Pro Ser Thr Ala Gly Tyr Glu Ser Lys
                165                 170                 175

Thr Glu Glu Gln Ala Pro Ser Glu Ser Gly Gln Tyr Gly Lys Arg Arg
            180                 185                 190

Lys

<210> SEQ ID NO 38
<211> LENGTH: 362
<212> TYPE: PRT

<213> ORGANISM: Dirofilaria immitis

<400> SEQUENCE: 38

Met Tyr Asn Leu Ala Lys Leu Leu Glu Asn Glu His Gly Ser Ile Glu
1               5                   10                  15

Ala Ser Phe His Val Tyr Val Glu Asn Phe Glu Gly Leu Asp Gly
            20                  25                  30

Glu Ser Trp Ser Ile Asp Gln Thr Asn Ala Gln Leu Tyr Pro Ile Ile
            35                  40                  45

Asp Glu Pro Phe Asn Asn Thr Val Arg Val Gly Arg Thr Ala Gln Phe
        50                  55                  60

Gln Cys Lys Val Lys Asn Gln Gln Pro Leu Ile Lys Trp Leu Lys
65                  70                  75                  80

Arg Ile Asp Asp Pro Asn Ala Ile Arg Gln Ala Asn Ala Asn Ala Thr
                85                  90                  95

Leu Ile His Ala Asn Asn Met His Leu Leu Leu Glu Lys Pro Glu
                100                 105                 110

Thr Ser Ala Glu Leu Ser Asp Gly Ile Ser Leu Asn Arg Leu Ile Ile
            115                 120                 125

Pro Asn Val Arg Tyr Glu His Ser Gly Thr Tyr Leu Cys Val Val Thr
        130                 135                 140

Asn Ala His Gly Asp Ile Ala Tyr Arg Ser Ala Tyr Leu His Val Ile
145                 150                 155                 160

Ala Arg Ser Asp His Gly Met Leu Ser Asn Ile Tyr Phe Tyr Gly Gly
                165                 170                 175

Ile Leu Val Leu Ile Val Val Phe Thr Leu Ile Thr Tyr Ala Val Tyr
            180                 185                 190

Phe Leu Arg Lys Asn Gln Ala Ala Lys Asn Ser Glu Ser Ala Gln Asp
        195                 200                 205

Ile Thr Asn Thr Arg Tyr Ser Phe Ser Leu Arg Pro Pro Pro Asn
210                 215                 220

Leu Pro Pro Pro Lys Ala Pro Ala Leu Pro Ser Glu Arg Gln Gln Leu
225                 230                 235                 240

Met Ser Asp Asn Gln Pro Cys Asp Arg Tyr Ala Val Asn Ser Ala Ala
                245                 250                 255

Thr Thr Tyr Tyr Pro Gln Phe Ala Thr Pro Asp Lys Lys Leu Gln Lys
            260                 265                 270

Ile Ile Thr Glu Ser Gly Gly Thr Arg Pro Thr Pro Ile Arg Arg Thr
        275                 280                 285

Asn Gly Gly Asp Thr Lys Tyr Arg Leu Lys Asp Glu Tyr Ile Asn Ser
290                 295                 300

Pro Lys Trp Val His Thr Lys Gly Asp Asn Ile Glu Val Glu Met Asp
305                 310                 315                 320

Gln Asn Leu Leu Lys Asn Arg Ser Ser His Cys Tyr Asn Pro Ile Ser
                325                 330                 335

Gly Ala Tyr Gly Arg Thr Asp Asn Ile Asp Arg Gln Gln Lys Ser
            340                 345                 350

Phe Leu Thr Ile Gly Asn Leu Gln Lys Arg
        355                 360

<210> SEQ ID NO 39
<211> LENGTH: 215
<212> TYPE: PRT
<213> ORGANISM: Dirofilaria immitis

<400> SEQUENCE: 39

Met Leu Lys Leu Ala Asn Thr Glu Ile Phe Phe Ile Ala Phe Leu Val
1               5                   10                  15

Tyr Ser Lys Glu Ile Ile Leu Asn Cys Tyr Glu Asp Tyr Lys Glu Cys
            20                  25                  30

Val Ala Thr Ser Asn Lys Thr Asn His Val Asn Met Asp Asn Val Asn
                35                  40                  45

Pro Gln Asn Leu Ile Glu Phe Cys Phe Asp His Thr Gln Asn Ile Leu
        50                  55                  60

Pro Cys Leu Val Thr Lys Leu Gly Leu Thr Lys Gly Ile Ser Val Ser
65                  70                  75                  80

Ile Phe Ser Leu Phe Leu Ser Thr Cys Glu Leu Glu Ala Gln Asn Asn
                85                  90                  95

Lys Ser Ser Thr Thr Glu Met Gln Gln Ile Leu Arg His Leu Leu
            100                 105                 110

Arg Leu Tyr Ala Tyr Phe Cys Ala Tyr Ser Asn Ile Ile Asp Leu His
        115                 120                 125

Arg Asn Arg Glu Cys Phe Arg Tyr Leu Met Lys Arg Cys Val Leu Asn
130                 135                 140

Lys Pro Asp Glu Ser Cys Met Phe Tyr His Cys Gly Lys Ile His Phe
145                 150                 155                 160

Asn Leu Ser Lys Ser Arg Lys Ile Leu Phe Thr Arg Gln His Asp
                165                 170                 175

Thr Thr Lys Ile Val Asn Leu Gly Asn Lys Met Asn Gln Leu Ala Thr
            180                 185                 190

Phe Asn Asn His Gln Val Arg Ser Ala Val Val Val Thr Leu Ile Ile
        195                 200                 205

Thr Phe Ile Asp Met Ile Gln
        210                 215

<210> SEQ ID NO 40
<211> LENGTH: 395
<212> TYPE: PRT
<213> ORGANISM: Dirofilaria immitis

<400> SEQUENCE: 40

Met Tyr Ser Gln Glu Asn Gln Asp Asp Lys Arg Arg Asn Asp Glu Arg
1               5                   10                  15

Ile Ala Leu Ser Val Pro Tyr Asn Asn Thr Asn Ile Met Asp Arg Ser
            20                  25                  30

Tyr Phe Lys Pro Ile Lys Leu Ser Tyr Pro Tyr Ser Asp Glu Cys Leu
                35                  40                  45

Glu Val Asn Lys Lys Ser Ser Asp Asp Ser Asp Gln Arg Leu Ser Gln
        50                  55                  60

Asn Ser Ser Thr Pro Gln Ser Asn Tyr Asp Gln Ser Ser Glu Arg Leu
65                  70                  75                  80

Ser Ile Asp Asp Ser Asp Leu Ile Asp Ser Thr Ser Ala Ala Gln
                85                  90                  95

Leu Ser Thr Ser Ser Pro Ile Ser Val Thr Ser Ala Ser Thr Ser Ser
            100                 105                 110

Phe Tyr Pro Thr Leu Asn Ile Gly Asn Gly Met Glu Met Asn Ala Lys
        115                 120                 125

Tyr Ala Lys Ile Glu Gln Ser Glu Gly Ile Arg Ser Asp Gln Ser Ser
130                 135                 140

```
Thr Leu Arg Ile Ser Asp Lys Tyr Lys Lys Tyr Thr Ala Ile Lys Arg
145                 150                 155                 160

Arg Leu Ser Glu Leu Cys Gly Ile Ile Glu Glu Lys Asp Lys Gln Leu
                165                 170                 175

Arg Val Arg Asn Gly Leu Asn Glu Lys Asp Leu Glu Ile Gly Lys
            180                 185                 190

Leu Cys Asp Lys Ile Arg Ala Leu Glu Tyr Asn Cys Gly Arg Leu Gln
                195                 200                 205

Ala Val Ile Glu Ser Val Gly Asp Glu Ser Asp Gln Asn Gln Ile Lys
            210                 215                 220

Leu His Glu Ile Ile Asn Glu Arg Asp Gly Leu Leu Val Arg Asn Ala
225                 230                 235                 240

Ser Leu Ser Arg Gln Ile Glu Phe Glu Lys Arg Glu Trp Ser Ile Glu
                245                 250                 255

Arg Glu Arg Leu Ser Met Asp Leu Asp Asp Val Thr Arg Glu Leu Glu
                260                 265                 270

Leu Gln Lys Met Ile Leu Asn Gly Glu Asn Ile Ser Glu Ile Val Gln
                275                 280                 285

Arg Trp Gln Thr Lys Val Phe Glu Leu Glu Gly Met Ile Ala Asp Arg
290                 295                 300

Asp Arg Ala Ile Arg Ala Gln Gln Val Arg Ile Ser Lys Leu Lys Gln
305                 310                 315                 320

Ser Leu Ala Glu Ala Asp Arg Ile Ser Cys Asp Ser Ser Glu Ser
                325                 330                 335

Gln Thr Lys Leu Asp Ser Pro Ser Phe Thr Cys Ile Lys Arg Leu Leu
                340                 345                 350

Leu Gln Tyr Leu Thr Ser Ser Asp Glu Glu Arg Ile Gln Leu Leu Arg
                355                 360                 365

Asn Val Ser Thr Met Leu His Leu Ser Asp Asp Glu Gln His Gln Val
                370                 375                 380

Leu Thr Asn Leu Lys Ser Arg Ile Gln Ile Ser
385                 390                 395

<210> SEQ ID NO 41
<211> LENGTH: 99
<212> TYPE: PRT
<213> ORGANISM: Dirofilaria immitis
<220> FEATURE:
<221> NAME/KEY: misc_feature
<222> LOCATION: (1)..(1)
<223> OTHER INFORMATION: Xaa can be any naturally occurring amino acid

<400> SEQUENCE: 41

Xaa Lys Cys Arg Asp Gln Arg Ala Glu Val Glu Tyr Val Asn Gly Ser
1               5                   10                  15

Ala Lys Asn Cys Leu Tyr Trp Pro Cys Thr Val Gly Tyr Phe Cys Glu
                20                  25                  30

Tyr Thr Glu Ser Arg Asn Gly Gly His Tyr Ile Cys Cys Gly Thr Asn
            35                  40                  45

Ala Asn Asn Ile Tyr Gly Lys Val Lys Val Tyr Pro Gly Thr Asn Lys
50                  55                  60

Pro Leu His Cys Ser Ile Met Asn Thr Cys Pro Phe Leu Asp Thr Pro
65                  70                  75                  80

Asn Cys Val Met Ser His Arg Tyr Gly Tyr Lys Val Cys Cys Ser Thr
                85                  90                  95

Met Asn Cys
```

<210> SEQ ID NO 42
<211> LENGTH: 589
<212> TYPE: PRT
<213> ORGANISM: Dirofilaria immitis

<400> SEQUENCE: 42

```
Met Leu Met Lys Gln Ser Asp Ser Cys Val Asp Tyr Phe Tyr Asp Gln
1               5                   10                  15

Tyr Lys Gly Gln Glu Tyr Val Lys Asp Asp Ala Phe Asn Thr Gln Asn
            20                  25                  30

Ile Thr Asp Asn Phe Arg Lys Ser Ser Asp Ile Ala Gln Leu Met
        35                  40                  45

Asn Ser Gln Ile Glu Leu Ile Ser Gln Pro Glu Lys Val Asn Glu Asp
50                  55                  60

Ser Ala Lys Ser Ser His Tyr Asn Asp Asp Leu Gln Lys Ser Ile Glu
65                  70                  75                  80

Asp Asp Thr Val Glu Ala Thr Gln Arg Lys Asp Glu Lys Leu Leu
                85                  90                  95

Glu Phe Leu His Ser Leu Ile Val Ser Thr Ile Pro Lys Thr Ile His
            100                 105                 110

Leu Glu Gly Asn Ser Val Asn Leu Leu Thr Leu Thr Thr Ile Thr
        115                 120                 125

Pro Ile Ala Ile Ile Thr Thr Lys Asn Thr Ser Gly Thr Ala Asn Ala
            130                 135                 140

Ile Thr Thr Arg Lys Tyr Lys Lys Tyr Lys Leu Asn Ala Phe Val Asn
145                 150                 155                 160

Ile Ser Ser Asp Thr Leu Thr Glu Leu Pro Lys Phe Leu Pro Glu Asn
                165                 170                 175

Phe Asn Ser Thr Asn Phe Ala Asn Val Glu Lys Thr Glu Lys Phe Ser
            180                 185                 190

Asn Ser Lys Gln Val Ala Thr Asp Ser Ile Phe Ser Leu Lys Glu Ser
        195                 200                 205

Ala Tyr Leu Glu Thr Pro Val Ile Arg Asp Phe Ser Ser Ala Asn Asp
    210                 215                 220

Ser Ala Lys Thr Asp Pro Leu Phe Thr Arg Asn Tyr Val Asp Lys Gln
225                 230                 235                 240

Ile Asp Met Asn Thr Thr Lys Phe Asn Lys Asn Leu Lys Lys Ser Arg
                245                 250                 255

Leu Thr Thr Ile Ser Thr Ser Asn Leu Thr Thr Val Leu Ser Gln Leu
            260                 265                 270

Gln Thr Thr Thr Ser Ile Ser Thr Thr Thr Ser Val Thr Thr Thr Ile
        275                 280                 285

Ser Thr Ser Ile Thr Ile Pro Glu Leu Thr Leu Val Ser Gln Ser His
    290                 295                 300

Arg His Leu His His Tyr His His His His Gln Tyr Glu Asn
305                 310                 315                 320

Tyr Asp His Glu Ser Pro Ile Ile Val Thr Ala Leu Phe Asp Ile Gly
                325                 330                 335

Arg Gly Lys Trp Pro Arg Tyr Thr Arg Thr Tyr Glu Gln Tyr Met Asn
            340                 345                 350

Tyr Leu Lys His Leu Leu Lys Leu Glu Asn Cys Leu Val Ile Tyr Thr
        355                 360                 365

Asp Ser Arg Gly Ala Glu Phe Val Arg Gln Thr Arg Asn Val His Asn
```

```
              370                 375                 380
Thr Gln Ile Phe Glu Ile Ser Met His Asp Leu Pro Leu Tyr Arg Tyr
385                 390                 395                 400

Arg Glu Glu Met Lys Gly Ile Ile Gln Arg Glu Gln Lys Asp Trp Gln
                405                 410                 415

Phe Ser Pro Lys Thr Arg Tyr His Pro Glu Ala Asn Ser Ala Asp Tyr
            420                 425                 430

Asn Ile Ile Val Asn Ser Lys Pro Tyr Phe Leu Tyr Asn Ala Thr Gln
                435                 440                 445

Asn Val Arg Phe Arg Thr Ser Asp Arg Met Phe Val Trp Ile Asp Ala
450                 455                 460

Gly Tyr Gly His Gly Arg Lys Gly Ile Ile Pro Asp His Cys His Trp
465                 470                 475                 480

Arg Pro Arg Leu Gln Arg Asp Arg Met Thr Ile Ile Gln Leu Thr Pro
                485                 490                 495

Lys His Asp Lys Val Ser Arg Tyr Ser Ile Thr Asp Leu Tyr Arg Val
                500                 505                 510

Asp Trp Val Val Leu Ser Gly Gly Phe Ile Ala Gly Asp Ser His Thr
            515                 520                 525

Ile Asn Arg Phe Tyr Arg Phe Tyr Gln Lys Leu Phe Met Glu Leu Leu
530                 535                 540

Asp Ser Gly Arg Ile Asp Asp Gln Thr Ile Leu Thr Leu Met Leu
545                 550                 555                 560

Lys His Tyr Thr Thr Leu Phe Asn Pro Ile Ser Ser Asn Gly Asp Trp
                565                 570                 575

Tyr Ala Leu Phe Arg Leu Phe Pro Cys His Asp Arg Gln
            580                 585

<210> SEQ ID NO 43
<211> LENGTH: 875
<212> TYPE: PRT
<213> ORGANISM: Dirofilaria immitis

<400> SEQUENCE: 43

Met Lys Gln Ala Thr Thr Trp Gly Ser Ile Cys Glu Met Cys Pro Cys
1               5                   10                  15

Ala Ala Lys Pro Ile Cys Pro Pro Val Ile Cys Pro Pro Arg Ile
                20                  25                  30

Cys Pro Pro Val Ile Cys Pro Pro Gln Ile Cys Pro Pro Cys Pro
            35                  40                  45

Pro Arg Ile Cys Pro Pro Val Ile Cys Pro Pro Gln Ile Cys Pro
    50                  55                  60

Pro Cys Pro Pro Gln Ile Cys Pro Pro Cys Pro Lys Pro Gln Pro Pro
65                  70                  75                  80

Pro Pro Pro Pro Pro Pro Val Leu Pro Ser Leu Pro Pro Thr Ser
                85                  90                  95

Phe Lys Pro Met Ile Thr Cys Cys Arg Thr Cys Ile Cys Tyr Ile Arg
                100                 105                 110

Arg Lys Arg Asp Ser Leu Asn Asp Tyr Asp Arg Ile His Asp Ile Asn
            115                 120                 125

Pro Val Cys Asn Asn Asp Gln Leu Met Met Ile Met Lys Lys Lys Ile
        130                 135                 140

Arg Thr Asn Val Thr Glu Ser Thr Ile Ala Ile Lys Lys Ala Ala Asp
145                 150                 155                 160
```

-continued

```
Ser Met Leu Gln Ala Glu Phe Asn Val Phe Cys Ala Ile Asn Asp Leu
            165                 170                 175

Thr His Val Ala His Ala Glu His Phe Cys Gln Tyr Lys Lys Asp Asn
        180                 185                 190

Ser Val Phe Asp Ser Phe Leu Phe Arg Ser Thr Leu Lys Gly Leu Ile
        195                 200                 205

Glu Glu Cys Arg Glu Gly Val Arg Trp Trp Pro Gly Ser Leu Gly Asp
    210                 215                 220

Leu Asp Phe Ser His Ile Ser Leu Tyr Arg Ala His Lys Tyr Ile Gly
225                 230                 235                 240

Asn Glu Glu Met Asn Arg Ser Thr Lys Thr Lys Ile Ser Phe Thr Arg
                245                 250                 255

Ile Asn Lys Lys Trp Arg Leu Gly His Thr Gly Lys Lys Tyr Asn Lys
            260                 265                 270

Val Arg Phe Ser Arg Asn Ile Ala Lys Lys Phe Ile Gly Val Cys Asn
        275                 280                 285

Ile Ile Arg Leu Lys Lys Ser Val Ser Arg Ser Val Arg Pro Phe Glu
        290                 295                 300

Asn Gln Lys Ser Thr Ser Phe Asn Val Phe Gln Leu Leu Val Pro Lys
305                 310                 315                 320

Glu Lys Val Glu Ile Val Val Asp Asp Thr Gln Ala Glu Glu Met Asn
                325                 330                 335

Ser Glu Thr Ala Gln Glu Val Gln Leu Phe Asn Val Arg Lys Ser Asn
            340                 345                 350

Ala Asp Ser Lys Thr Asp Gly Glu Lys Asp Thr Ala Asp Leu Asp Val
        355                 360                 365

Ile Leu Leu Thr Asn Glu Glu Cys Ser Ser Arg Gln Glu Asn Leu
        370                 375                 380

Asn Lys Asp Glu Pro Glu Ile Val Ile Leu Asp Asp Ser Ala Pro Ser
385                 390                 395                 400

Lys Ser Asp Leu Asn Thr Ser Asp Glu Ile Ile Cys Leu Gln Asp Leu
                405                 410                 415

Lys Met Val Asn Glu Val Pro Thr Phe Ser Val Thr Pro Lys Gln Lys
            420                 425                 430

Thr Val Lys Glu Leu Pro Arg Glu Thr Arg Thr Tyr Gly Thr Arg Arg
        435                 440                 445

Gly Arg Gln Ser Arg Ala Tyr Cys Glu Asp Leu Arg Lys Phe Pro Ser
    450                 455                 460

Ile Arg Asn Pro Val Ser Ser Ser Ser Ile His Ala Lys Asn
465                 470                 475                 480

Met Pro Glu Phe Val Asp Leu Leu Thr Gln Gly Thr Leu Leu Ile Cys
                485                 490                 495

Lys Lys Trp Leu Arg Arg Trp Asp Ile Val Gln Ser Gly Val Ile Gly
            500                 505                 510

Gly Asn Pro Leu Arg Ile Cys Ser Tyr Asn Val Leu Cys Gln Gln Thr
        515                 520                 525

Ala Tyr Lys Thr Pro Glu Leu Tyr Ile His Leu Thr Lys Pro Gly Arg
    530                 535                 540

Ala Tyr Glu Leu Thr Trp Glu Asn Arg Trp Arg Leu Leu Thr Arg Glu
545                 550                 555                 560

Phe Ser Met Ile Gly Ala Asp Ile Phe Cys Leu Gln Glu Val Gln Tyr
                565                 570                 575

Asp His Tyr Asp Gln Phe Arg Pro Tyr Phe Glu Ala Ala Gly Phe
```

```
                580             585             590
Phe Gly Lys Tyr Lys Arg Thr Asn Asn Leu Leu Asp Gly Cys Ala
            595             600             605
Ile Phe Tyr Lys Ser His Leu Gln Leu His Tyr Arg Tyr Ile Glu
            610             615             620
Tyr Phe Leu Asn Ile Asp Ser Val Leu Asn Arg Asp Asn Val Gly Gln
625             630             635             640
Leu Ile Arg Leu Lys Asp Met Arg Ser Gly Arg Glu Phe Cys Val Val
            645             650             655
Asn Thr His Leu Leu Phe Asn Lys Arg Arg Gly Asp Val Lys Leu Ala
            660             665             670
Gln Leu Ala Ile Leu Leu Ala Asn Ile Asp Gln Glu Cys Gly Pro Glu
            675             680             685
Ser Gly Gln Glu Cys Pro Tyr Ile Leu Cys Gly Asp Phe Asn Phe His
            690             695             700
Pro Tyr Ser Pro Ile Tyr Asn Phe Ile Met Asn Gly Glu Ile Cys Phe
705             710             715             720
Thr Asn Leu Arg Arg Gly Asp Ile Ser Gly Gln Gly Asn Ala Gly Gly
            725             730             735
Pro Phe Val Ser Val Asn Leu Leu Pro Glu Asp Val Lys Ile Ala Arg
            740             745             750
Asn Cys Arg Phe Asn Tyr Leu Lys Asn Arg Thr Met Leu Leu Pro Ser
            755             760             765
Leu Asn Cys Trp Ser His Pro Leu Cys Phe Asn Ser Val Tyr Gln Asn
            770             775             780
Met Asn Gly Glu Thr Arg Pro Met Ile Ser Thr Tyr His Ser Ile Glu
785             790             795             800
Ala Val Asn Pro Asp Phe Ile Phe Tyr Ser Val Lys Ser Lys Arg Val
            805             810             815
Gln Gln Ser Met Leu Pro His Ser Val Pro Ala Met Asn Val Ser Glu
            820             825             830
Arg Glu Ile Arg Leu Ile Arg Arg Leu Ser Leu Pro Asp Met Asn Glu
            835             840             845
Leu Ala Gly Thr Leu Gly Pro Trp Pro Asn Ser Thr Thr Pro Ser Asp
            850             855             860
His Ile Pro Leu Ile Ala Asp Phe Val Leu Gln
865             870             875

<210> SEQ ID NO 44
<211> LENGTH: 158
<212> TYPE: PRT
<213> ORGANISM: Dirofilaria immitis

<400> SEQUENCE: 44

Met Tyr Cys Lys Leu Ile Ile Ser Phe Tyr Met Leu Leu Ser Ile Ala
1               5                   10                  15
Asn Met Thr His Leu Val Gly Tyr Arg Pro Gln Ile Tyr Leu Gln Gly
                20                  25                  30
Ile Pro Gln Asn Ile Gln Ser His Asp Ile Gln Arg Leu Asp Met Gln
            35                  40                  45
Gln Gln Ser Leu Lys Leu Pro Asp Thr Glu Leu Tyr Ser Ile Pro Ser
        50                  55                  60
His Asp Asn Gln Leu Gln Gly Leu Gln Leu Tyr Asp Met Gln Phe Gln
65                  70                  75                  80
```

```
Gly Lys Gln Ser Lys Gly Ser Glu Lys Leu Cys Ser Gly Cys Lys Ile
                85                  90                  95

Ser Ile Asn Cys Ser Gly Lys Lys Cys Val Pro Met Arg Thr Arg Lys
            100                 105                 110

Pro Ile Val Thr Thr Pro Ser Pro Leu Ser Thr Gln Arg Pro Val Leu
            115                 120                 125

Thr Arg Pro Arg Leu Leu Ala Asp Cys Pro Cys Pro Cys His Val Ser
        130                 135                 140

Arg Gln Cys Arg Ile Cys Gln Pro Cys Gln Ser Phe Ile
145                 150                 155

<210> SEQ ID NO 45
<211> LENGTH: 230
<212> TYPE: PRT
<213> ORGANISM: Dirofilaria immitis

<400> SEQUENCE: 45

Met Phe Val Gly Met Arg Leu Tyr Leu Ala Ile Asp Val Leu Leu Leu
1               5                   10                  15

Leu Val Leu Arg Ile Lys Ser Asn Arg Ile Ile Leu His Arg Phe Ser
            20                  25                  30

Leu Phe Ile Gln Gln His Cys Cys Asn Asn Ile Ser Gln Ile His Arg
        35                  40                  45

Leu Asn Asp Cys Lys Tyr Ser Lys Val Arg Met Lys Ile Asp Lys Lys
    50                  55                  60

Ile Leu Ile Ile Val Ser Lys Thr Glu Trp Cys Asn Glu Ala Ile Lys
65                  70                  75                  80

Val Val Phe Gly Lys Ser Ala Glu Ala Arg Arg Asn Arg Ser Asp Ala
                85                  90                  95

Ile Ser Trp Val Thr Pro Tyr Asn Phe Thr Gly Leu Met Asn Leu His
            100                 105                 110

Ser Lys Trp Arg Tyr Asp Ala Tyr Phe Asp Asn Val Thr Arg Thr Ala
            115                 120                 125

His Gly Leu Ala Arg Ile Asp Leu Leu Cys Pro Lys Arg Arg Ser His
        130                 135                 140

Ser Gly Arg Arg Ile Leu Lys Arg Ser Ile Gln Glu Asn Lys Gln Glu
145                 150                 155                 160

Lys Ser Arg Arg Ser Phe Thr Val Asn Ile Tyr Gly Ser Lys Gly
                165                 170                 175

Ile Phe Thr Ile Thr Val Gly Val Ile Tyr Ala Ile Phe Gly Val
            180                 185                 190

Cys Phe Leu Ile Thr Asn Met Ala Tyr Leu Ser Gly Ile Tyr Thr Val
        195                 200                 205

His Asn Thr Ser Val Ile Pro Glu Asp Lys Lys Arg Lys Glu Thr Ser
    210                 215                 220

Lys Arg Lys Glu Ile Leu
225                 230

<210> SEQ ID NO 46
<211> LENGTH: 279
<212> TYPE: PRT
<213> ORGANISM: Dirofilaria immitis

<400> SEQUENCE: 46

Met Ile Ser Val Phe Leu Leu Leu Thr Val Ile Val Ser Tyr Val Glu
1               5                   10                  15
```

```
Thr Ile Gly Glu Asn Pro Met Asp Ile Asn Ala Leu Ala Gly Ile Ile
            20                  25                  30

Gly Gly Ile Ser Asn Met Met Gln Asn Val Glu Thr Ile Asp Val
        35                  40                  45

Pro Ser Ser Gln Ile Met Gly Gln Trp Tyr Gln Val Tyr Lys Ala Ala
50                      55                  60

Ile Ser Phe Asp Ala Tyr Lys Thr Asp Met Phe Cys Pro Val Ala Tyr
65                  70                  75                  80

Phe Lys Pro Asn Ser Val Met Gly Glu Asp Gly Phe Ser Ile Glu Glu
                85                  90                  95

Ala Tyr Arg Val Ile Thr Lys Asn Gly Pro Val Glu Thr Phe Lys Arg
            100                 105                 110

Asp Leu Asn Lys Val Gly Thr Gly Gln Tyr Trp Met Tyr Thr Glu Glu
        115                 120                 125

Tyr Phe Tyr Pro Arg Gln Phe Asn Ile Ile Gly Val Gly Pro Asn Tyr
    130                 135                 140

Thr Asn Ala Thr Asp Gly Arg Glu Lys Glu Asn Leu Tyr Glu Tyr Met
145                 150                 155                 160

Ile Val Thr Asp Ala Asn Arg Leu Ser Leu Ser Val Tyr Ala Arg His
                165                 170                 175

Pro Met Ile Phe Tyr Gln Lys Tyr Asn Glu Glu Val Val Lys Phe Leu
            180                 185                 190

Glu His Ala Gly Phe Gly Gly Arg Val Phe Trp Asn Ser Pro Arg Pro
        195                 200                 205

Ile Tyr Gln Gly Thr Asp Cys Glu Trp Pro Ser Glu Lys Glu Val Phe
    210                 215                 220

Ala Arg Arg Val Leu Lys Asn Gln Glu Ala Ala Arg Asn Thr Gly Leu
225                 230                 235                 240

Glu Thr Ala Thr Lys Ser Gly Leu Phe Gly Ser Ser Leu Thr Thr Asp
                245                 250                 255

Ala Tyr Asn Pro Ile Lys Glu Met Leu Gln Asn Pro Gln Leu Ala Leu
            260                 265                 270

Gln Lys Leu Val Gln Gly His
            275

<210> SEQ ID NO 47
<211> LENGTH: 200
<212> TYPE: PRT
<213> ORGANISM: Dirofilaria immitis

<400> SEQUENCE: 47

Met Thr Val Ile Lys Ser Met Leu Asn Ile Thr His Val Ile Phe Asp
1               5                   10                  15

Leu Asp Gly Leu Leu Ile Asn Thr Glu Ile Val Phe Ser Gln Val Asn
            20                  25                  30

Gln Cys Leu Leu Ser Lys Tyr Gly Lys Lys Phe Thr Ser His Leu Arg
        35                  40                  45

Gly Leu Val Thr Gly Met Pro Lys Lys Ala Ala Val Ala His Ile Leu
50                  55                  60

Glu His Glu Arg Leu Ser Glu Lys Ile Asp Val Asp Glu Tyr Cys Lys
65                  70                  75                  80

Lys Tyr Asp Glu Met Ala Glu Glu Met Leu Pro Lys Cys Ser Leu Met
                85                  90                  95

Pro Gly Val Met Lys Leu Val Arg His Leu Lys Ala His Ser Ile Pro
            100                 105                 110
```

```
Met Ala Ile Cys Thr Gly Ala Thr Lys Lys Glu Phe Glu Leu Lys Thr
            115                 120                 125

Arg Cys His Lys Glu Leu Leu Asp Leu Ile Ser Leu Arg Val Leu Ser
        130                 135                 140

Gly Asp Asp Pro Ala Val Lys Arg Gly Lys Pro Ala Pro Asp Pro Phe
145                 150                 155                 160

Leu Val Thr Met Glu Arg Phe Lys Gln Lys Pro Glu Lys Ala Glu Asn
            165                 170                 175

Val Leu Val Phe Glu Asp Ala Thr Asn Gly Val Tyr Ala Ala Ile Ala
            180                 185                 190

Ala Glu Glu Ser Lys Ile Val Lys
            195                 200

<210> SEQ ID NO 48
<211> LENGTH: 116
<212> TYPE: PRT
<213> ORGANISM: Dirofilaria immitis

<400> SEQUENCE: 48

Met Ile Leu Glu Gln Leu Glu Val Pro Pro Phe Leu Val Gly Ala Pro
1               5                   10                  15

Gln Ser Val Ile Lys Gln Phe Tyr Asp Leu Leu Lys Ala Asp Glu Thr
            20                  25                  30

Lys Thr Asp Ala Gln Thr Glu Ala Asp Val Glu Ala Phe Ile Asn Arg
        35                  40                  45

Leu Gly Gly Thr Tyr Lys Thr Arg Phe Asp Gln Phe Lys Gln Glu Ile
    50                  55                  60

Lys Gln Gly Lys Ala Ala Tyr Glu Arg Leu His Gln Gln Ala Val Ala
65                  70                  75                  80

Lys Phe Ser Lys Glu Ala Arg Glu Ala Asp Ala Lys Met Ser Ala Ile
                85                  90                  95

Ala Asp Ser Pro Ser Leu Thr Thr Gln Gln Lys Thr Gln Gln Ile Gln
            100                 105                 110

Ala Ile Met Asp
        115

<210> SEQ ID NO 49
<211> LENGTH: 158
<212> TYPE: PRT
<213> ORGANISM: Dirofilaria immitis

<400> SEQUENCE: 49

Met Leu Lys Tyr Gly Ile Leu Leu Ile Leu Ile Thr Val Gly Ala Tyr
1               5                   10                  15

Cys Asp Leu Leu Ser Glu Ala Gly Asp Phe Phe Ser Lys His Phe Thr
            20                  25                  30

Asp Phe Lys Ser Leu Phe Ala Ser Asp Glu Lys Gln Leu Gln Gln Asn
        35                  40                  45

Met Asp Arg Val Lys Asp Leu Leu Ala Thr Ile Gln Asp Lys Met Thr
    50                  55                  60

Ile Leu Lys Gln Leu Ala Asp Asn Ser Gln Lys Ser Thr Leu Glu Lys
65                  70                  75                  80

Ile Thr Asp Ile Ile Ser Gln Val Asn Asp Phe Arg Glu Asn Val Phe
                85                  90                  95

Asn Ser Asn Val Asp Phe Asn Gln Lys Lys Thr Lys Trp Glu Glu Val
            100                 105                 110
```

Val Thr Lys Ile Phe Val Thr Asp Gly Leu Asn Lys Val Ile Pro Leu
            115                 120                 125

Leu Gln Lys Ala Lys Asn Ser Ala Pro Ala Thr Phe Ile Thr Tyr Leu
        130                 135                 140

Leu Thr Cys Ile Val Pro Leu Leu Ile Asn Ala Leu Arg Glu
145                 150                 155

<210> SEQ ID NO 50
<211> LENGTH: 20
<212> TYPE: PRT
<213> ORGANISM: Artificial Sequence
<220> FEATURE:
<223> OTHER INFORMATION: Flexible linker

<400> SEQUENCE: 50

Lys Gly Pro Asp Val Pro Glu Thr Asn Gln Gln Cys Pro Ser Asn Thr
1               5                   10                  15

Gly Met Thr Asp
            20

<210> SEQ ID NO 51
<211> LENGTH: 114
<212> TYPE: PRT
<213> ORGANISM: Onchocerca volvulus

<400> SEQUENCE: 51

Met Ala Arg Ile Asn Arg Leu Asn Phe Leu Leu Cys Ile Val His Ala
1 5 10 15

Asn Ile Thr Ser Ala Pro Asn Pro Lys Asp Ser Asn Asp Glu Leu Phe
20 25 30

Ala Asp Ala Glu Ser Ala Leu Gly Ser Glu Tyr Ala Gln Phe Val Glu
35 40 45

Gln Ser Lys Gln His Lys Pro Val Tyr Phe Ser Asp Asn Gln Asn Thr
50 55 60

Leu Glu Thr Ile Lys Leu Glu Ser Ile Pro Asn Pro Glu Thr Glu Thr
65 70 75 80

Ala Tyr Pro Met Phe Ile Cys Gly Phe Leu Gly Cys Met Lys Lys Met
85 90 95

Asn Ser Val Glu Glu Tyr Leu Glu His Phe Lys Met His Glu Lys Gln
100 105 110

Gly Tyr

<210> SEQ ID NO 52
<211> LENGTH: 20
<212> TYPE: PRT
<213> ORGANISM: Onchocerca volvulus

<400> SEQUENCE: 52

Cys Pro Ser Leu Ser Ser Tyr Cys Glu Asp Trp Asp Pro Glu Asp Phe
1 5 10 15

Pro Ser Phe Val
20

<210> SEQ ID NO 53
<211> LENGTH: 29
<212> TYPE: PRT
<213> ORGANISM: Onchocerca volvulus

<400> SEQUENCE: 53

-continued

```
Leu Pro Ile Asp Lys Gln Asn Glu Ala Thr Leu Leu Trp Asn Ser Leu
1               5                   10                  15

Tyr Pro Asp Asp Ile Tyr Asn Glu Cys Gly Pro Arg Phe
            20                  25

<210> SEQ ID NO 54
<211> LENGTH: 25
<212> TYPE: PRT
<213> ORGANISM: Onchocerca volvulus

<400> SEQUENCE: 54

Ala Phe Ala Pro Asn Pro Lys Asp Ser Asn Asn Glu Leu Phe Ala Asp
1               5                   10                  15

Ala Glu Ser Ala Leu Gly Ser Glu Tyr
            20                  25

<210> SEQ ID NO 55
<211> LENGTH: 24
<212> TYPE: PRT
<213> ORGANISM: Onchocerca volvulus

<400> SEQUENCE: 55

Gly Cys Met Lys Lys Met Asn Ser Val Glu Glu Tyr Leu Glu His Phe
1               5                   10                  15

Lys Met His Glu Lys Gln Gly Tyr
            20

<210> SEQ ID NO 56
<211> LENGTH: 36
<212> TYPE: PRT
<213> ORGANISM: Onchocerca volvulus

<400> SEQUENCE: 56

Ile Asn Lys Phe Tyr Asp Met Leu Arg Lys Trp Ala Glu Lys Tyr Ser
1               5                   10                  15

Val Gln Ala Glu Thr Asn Arg Phe Ile Ala Glu Glu Met Asn Tyr Asp
            20                  25                  30

Lys Met Gln Ser
        35

<210> SEQ ID NO 57
<211> LENGTH: 35
<212> TYPE: PRT
<213> ORGANISM: Onchocerca volvulus

<400> SEQUENCE: 57

Ala Pro Pro Asn Arg Asp Thr Ala Asp Asp Leu Gln Asn Ala Asp Met
1               5                   10                  15

Gln Arg Gln Trp Glu Gln Glu Gln Arg Gln Arg Glu Glu Val Gln Lys
            20                  25                  30

Glu Glu Ile
        35

<210> SEQ ID NO 58
<211> LENGTH: 66
<212> TYPE: PRT
<213> ORGANISM: Onchocerca volvulus

<400> SEQUENCE: 58

Thr Asp Met Asp Glu Leu Glu Glu Gln Arg Lys Gln Asp Phe Lys Gln
1               5                   10                  15
```

-continued

```
Tyr Glu Met Lys Lys Ala Glu Glu Asp His Lys Met Gln Ala Ile
             20                  25                  30

Gln Thr Glu Arg Glu Tyr Ile Arg Gln Met Glu Gln Arg Arg
         35                  40                  45

Arg His Asn Lys His Glu Pro Leu Lys His Pro Gly Ser Arg Asn Gln
     50                  55                  60

Leu Arg
65

<210> SEQ ID NO 59
<211> LENGTH: 28
<212> TYPE: PRT
<213> ORGANISM: Onchocerca volvulus

<400> SEQUENCE: 59

Asp Arg Glu Ala Gln Glu Glu Lys Pro Asp Gln Gly Trp Glu Asp Ile
1               5                  10                  15

Gly Asp Lys Asp Gln Tyr Thr Lys Glu Glu Leu Glu
            20                  25

<210> SEQ ID NO 60
<211> LENGTH: 30
<212> TYPE: PRT
<213> ORGANISM: Onchocerca volvulus

<400> SEQUENCE: 60

Thr Pro Ala Pro Thr Pro Asp Pro Ser Arg Met Ile Gln Pro Asp Gln
1               5                  10                  15

Ala Pro Met Gln Arg Leu Asp Ala Pro Ser Asp Gln Val Gly
            20                  25                  30

<210> SEQ ID NO 61
<211> LENGTH: 21
<212> TYPE: PRT
<213> ORGANISM: Onchocerca volvulus

<400> SEQUENCE: 61

Val Ser Glu Ile Leu Thr Val Cys Leu Lys Glu Gly Phe Lys Lys Pro
1               5                  10                  15

Ser Asn Leu Gly Ile
            20

<210> SEQ ID NO 62
<211> LENGTH: 130
<212> TYPE: PRT
<213> ORGANISM: Onchocerca volvulus

<400> SEQUENCE: 62

Lys Asn Pro Ser Lys Met Glu Ser Lys Thr Gly Glu Asn Gln Asp Arg
1               5                  10                  15

Pro Val Leu Leu Gly Gly Trp Glu Asp Arg Asp Pro Lys Asp Glu Glu
            20                  25                  30

Ile Leu Glu Leu Leu Pro Ser Ile Leu Met Lys Val Asn Glu Gln Ser
         35                  40                  45

Lys Asp Glu Tyr His Leu Met Pro Ile Lys Leu Leu Val Ser Ser
     50                  55                  60

Gln Val Val Ala Gly Val Lys Tyr Lys Met Asp Val Gln Val Ala Arg
65                  70                  75                  80

Ser Gln Cys Lys Lys Ser Ser Asn Glu Lys Val Asp Leu Thr Lys Cys
                85                  90                  95
```

```
Lys Lys Leu Glu Gly His Pro Glu Lys Val Met Thr Leu Glu Val Trp
            100                 105                 110

Glu Lys Pro Trp Glu Asn Phe Met Arg Val Glu Ile Leu Gly Thr Lys
        115                 120                 125

Glu Val
    130

<210> SEQ ID NO 63
<211> LENGTH: 181
<212> TYPE: PRT
<213> ORGANISM: Onchocerca volvulus

<400> SEQUENCE: 63

Lys Ile Ser Ala Glu Asn Ala Asn Cys Lys Lys Cys Thr Pro Met Leu
1               5                   10                  15

Val Asp Ser Ala Phe Lys Glu His Gly Ile Val Pro Asp Val Val Ser
            20                  25                  30

Thr Ala Pro Thr Lys Leu Val Asn Val Ser Tyr Asn Asn Leu Thr Val
        35                  40                  45

Asn Leu Gly Asn Glu Leu Thr Pro Thr Gln Val Lys Asn Gln Pro Thr
50                  55                  60

Lys Val Ser Trp Asp Ala Glu Pro Gly Ala Leu Tyr Thr Leu Val Met
65                  70                  75                  80

Thr Asp Pro Asp Ala Pro Ser Arg Lys Asn Pro Val Phe Arg Glu Trp
                85                  90                  95

His His Trp Leu Ile Ile Asn Ile Ser Gly Gln Asn Val Ser Ser Gly
            100                 105                 110

Thr Val Leu Ser Asp Tyr Ile Gly Ser Gly Pro Arg Lys Gly Thr Gly
        115                 120                 125

Leu His Arg Tyr Val Phe Leu Val Tyr Lys Gln Pro Gly Ser Ile Thr
130                 135                 140

Asp Thr Gln His Gly Gly Asn Arg Arg Asn Phe Lys Val Met Asp Phe
145                 150                 155                 160

Ala Asn Lys His His Leu Gly Asn Pro Val Ala Gly Asn Phe Phe Gln
                165                 170                 175

Ala Lys His Glu Asp
            180

<210> SEQ ID NO 64
<211> LENGTH: 436
<212> TYPE: PRT
<213> ORGANISM: Artificial Sequence
<220> FEATURE:
<223> OTHER INFORMATION: Ov-103-RAL2-CPI2M fusion protein

<400> SEQUENCE: 64

Asp Leu Leu Ser Glu Ala Gly Asp Phe Phe Thr Lys His Phe Thr Asp
1               5                   10                  15

Ile Lys Ser Leu Phe Ala Lys Asp Glu Lys Gln Leu Gln Gln Ser Val
            20                  25                  30

Asp Arg Val Lys Asp Leu Leu Ala Thr Ile Gln Asp Lys Met Ser Met
        35                  40                  45

Leu Gln Pro Leu Ala Asn Asp Met Gln Lys Thr Thr Leu Gly Lys Ile
    50                  55                  60

Gly Asp Leu Ile Ser Gln Val Asn Ser Phe Arg Glu Thr Met Ser Asn
65                  70                  75                  80
```

```
Pro Lys Met Asp Phe Thr Asn Lys Glu Asn Lys Trp Glu Glu Leu Leu
                85                  90                  95
Lys Lys Ile Phe Val Thr Glu Gly Leu Asn Lys Val Ile Pro Leu Leu
            100                 105                 110
Gln Lys Leu Lys Asn Ser Ala Lys Gly Pro Asp Val Pro Glu Thr Asn
        115                 120                 125
Gln Gln Cys Pro Ser Asn Thr Gly Met Thr Asp Pro Gln Arg Arg Gln
    130                 135                 140
Gln Gln Gln Gln Gln Gln Gln Gln Arg Asp Glu Arg Glu Ile
145                 150                 155                 160
Pro Pro Phe Leu Glu Gly Ala Pro Pro Ser Val Ile Asp Glu Phe Tyr
                165                 170                 175
Asn Leu Leu Lys Thr Asp Glu Asn Lys Thr Asp Gln Gln Thr Glu Ala
            180                 185                 190
Asp Val Glu Ala Phe Ile Asn Arg Leu Gly Gly Ser Tyr Lys Val Arg
        195                 200                 205
Phe Thr Gln Phe Met Glu Glu Val Lys Lys Ala Arg Ala Asp Tyr Glu
    210                 215                 220
Arg Ile His Gln Gln Ala Val Ala Arg Phe Ser Pro Ala Ala Lys Asp
225                 230                 235                 240
Ala Asp Ala Arg Met Ser Ala Ile Ala Asp Ser Pro His Leu Thr Thr
                245                 250                 255
Arg Gln Lys Ser Gln Gln Ile Gln Ala Ile Met Asp Ser Leu Ser Glu
            260                 265                 270
Ser Val Arg Arg Glu Ile Ile Asn Ala Leu Ser Pro Gln Glu Lys Gly
        275                 280                 285
Pro Asp Val Pro Glu Thr Asn Gln Gln Cys Pro Ser Asn Thr Gly Met
    290                 295                 300
Thr Asp Lys Asn Pro Ser Lys Met Glu Ser Lys Thr Gly Glu Asn Gln
305                 310                 315                 320
Asp Arg Pro Val Leu Leu Gly Gly Trp Glu Arg Asp Pro Lys Asp
                325                 330                 335
Glu Glu Ile Leu Glu Leu Leu Pro Ser Ile Leu Met Lys Val Asn Glu
            340                 345                 350
Gln Ser Lys Asp Glu Tyr His Leu Met Pro Ile Lys Leu Leu Lys Val
        355                 360                 365
Ser Ser Gln Val Val Ala Gly Val Lys Tyr Lys Met Asp Val Gln Val
    370                 375                 380
Ala Arg Ser Gln Cys Lys Lys Ser Ser Asn Glu Lys Val Asp Leu Thr
385                 390                 395                 400
Lys Cys Lys Lys Leu Glu Gly His Pro Glu Lys Val Met Thr Leu Glu
                405                 410                 415
Val Trp Glu Lys Pro Trp Glu Asn Phe Met Arg Val Glu Ile Leu Gly
            420                 425                 430
Thr Lys Glu Val
        435

<210> SEQ ID NO 65
<211> LENGTH: 286
<212> TYPE: PRT
<213> ORGANISM: Artificial Sequence
<220> FEATURE:
<223> OTHER INFORMATION: Ov103-RAL2 fusion protein

<400> SEQUENCE: 65
```

```
Asp Leu Leu Ser Glu Ala Gly Asp Phe Phe Thr Lys His Phe Thr Asp
1               5                   10                  15

Ile Lys Ser Leu Phe Ala Lys Asp Glu Lys Gln Leu Gln Gln Ser Val
            20                  25                  30

Asp Arg Val Lys Asp Leu Leu Ala Thr Ile Gln Asp Lys Met Ser Met
        35                  40                  45

Leu Gln Pro Leu Ala Asn Asp Met Gln Lys Thr Thr Leu Gly Lys Ile
    50                  55                  60

Gly Asp Leu Ile Ser Gln Val Asn Ser Phe Arg Glu Thr Met Ser Asn
65                  70                  75                  80

Pro Lys Met Asp Phe Thr Asn Lys Glu Asn Lys Trp Glu Glu Leu Leu
                85                  90                  95

Lys Lys Ile Phe Val Thr Glu Gly Leu Asn Lys Val Ile Pro Leu Leu
            100                 105                 110

Gln Lys Leu Lys Asn Ser Ala Lys Gly Pro Asp Val Pro Glu Thr Asn
        115                 120                 125

Gln Gln Cys Pro Ser Asn Thr Gly Met Thr Asp Pro Gln Arg Arg Gln
    130                 135                 140

Gln Gln Gln Gln Gln Gln Gln Gln Gln Arg Asp Glu Arg Glu Ile
145                 150                 155                 160

Pro Pro Phe Leu Glu Gly Ala Pro Pro Ser Val Ile Asp Glu Phe Tyr
                165                 170                 175

Asn Leu Leu Lys Thr Asp Glu Asn Lys Thr Asp Gln Gln Thr Glu Ala
            180                 185                 190

Asp Val Glu Ala Phe Ile Asn Arg Leu Gly Gly Ser Tyr Lys Val Arg
        195                 200                 205

Phe Thr Gln Phe Met Glu Glu Val Lys Lys Ala Arg Ala Asp Tyr Glu
    210                 215                 220

Arg Ile His Gln Gln Ala Val Ala Arg Phe Ser Pro Ala Ala Lys Asp
225                 230                 235                 240

Ala Asp Ala Arg Met Ser Ala Ile Ala Asp Ser Pro His Leu Thr Thr
                245                 250                 255

Arg Gln Lys Ser Gln Gln Ile Gln Ala Ile Met Asp Ser Leu Ser Glu
            260                 265                 270

Ser Val Arg Arg Glu Ile Ile Asn Ala Leu Ser Pro Gln Glu
        275                 280                 285

<210> SEQ ID NO 66
<211> LENGTH: 297
<212> TYPE: PRT
<213> ORGANISM: Artificial Sequence
<220> FEATURE:
<223> OTHER INFORMATION: OvRAL2-CPI2M fusion protein

<400> SEQUENCE: 66

Pro Gln Arg Arg Gln Gln Gln Gln Gln Gln Gln Gln Gln Gln Gln Arg
1               5                   10                  15

Asp Glu Arg Glu Ile Pro Pro Phe Leu Glu Gly Ala Pro Pro Ser Val
            20                  25                  30

Ile Asp Glu Phe Tyr Asn Leu Leu Lys Thr Asp Glu Asn Lys Thr Asp
        35                  40                  45

Gln Gln Thr Glu Ala Asp Val Glu Ala Phe Ile Asn Arg Leu Gly Gly
    50                  55                  60

Ser Tyr Lys Val Arg Phe Thr Gln Phe Met Glu Glu Val Lys Lys Ala
65                  70                  75                  80
```

```
Arg Ala Asp Tyr Glu Arg Ile His Gln Gln Ala Val Ala Arg Phe Ser
                85              90                  95

Pro Ala Ala Lys Asp Ala Asp Ala Arg Met Ser Ala Ile Ala Asp Ser
            100             105                 110

Pro His Leu Thr Thr Arg Gln Lys Ser Gln Gln Ile Gln Ala Ile Met
        115                 120             125

Asp Ser Leu Ser Glu Ser Val Arg Arg Glu Ile Ile Asn Ala Leu Ser
    130             135                 140

Pro Gln Glu Lys Gly Pro Asp Val Pro Glu Thr Asn Gln Gln Cys Pro
145             150             155                 160

Ser Asn Thr Gly Met Thr Asp Lys Asn Pro Ser Lys Met Glu Ser Lys
                165             170                 175

Thr Gly Glu Asn Gln Asp Arg Pro Val Leu Leu Gly Gly Trp Glu Asp
            180             185             190

Arg Asp Pro Lys Asp Glu Glu Ile Leu Glu Leu Leu Pro Ser Ile Leu
        195             200             205

Met Lys Val Asn Glu Gln Ser Lys Asp Glu Tyr His Leu Met Pro Ile
    210             215             220

Lys Leu Leu Lys Val Ser Ser Gln Val Val Ala Gly Val Lys Tyr Lys
225             230             235                 240

Met Asp Val Gln Val Ala Arg Ser Gln Cys Lys Lys Ser Ser Asn Glu
            245             250             255

Lys Val Asp Leu Thr Lys Cys Lys Lys Leu Glu Gly His Pro Glu Lys
            260             265             270

Val Met Thr Leu Glu Val Trp Glu Lys Pro Trp Glu Asn Phe Met Arg
        275             280             285

Val Glu Ile Leu Gly Thr Lys Glu Val
    290             295
```